(12) United States Patent
Stevenson et al.

(10) Patent No.: US 8,996,126 B2
(45) Date of Patent: Mar. 31, 2015

(54) COMPOSITE RF CURRENT ATTENUATOR FOR A MEDICAL LEAD

(75) Inventors: Robert A. Stevenson, Canyon Country, CA (US); Robert Shawn Johnson, North Tonawanda, NY (US); Kishore Kumar Kondabatni, Williamsville, NY (US); Joseph Spaulding, Williamsville, NY (US); Dominick J. Frustaci, Williamsville, NY (US); Warren S. Dabney, Orchard Park, NY (US); Holly Noelle Moschiano, Lancaster, NY (US)

(73) Assignee: Greatbatch Ltd., Clarence, NY (US)

( * ) Notice: Subject to any disclaimer, the term of this patent is extended or adjusted under 35 U.S.C. 154(b) by 340 days.

(21) Appl. No.: 13/401,608

(22) Filed: Feb. 21, 2012

(65) Prior Publication Data

US 2012/0253340 A1 Oct. 4, 2012

Related U.S. Application Data

(63) Continuation-in-part of application No. 12/751,711, filed on Mar. 31, 2010, now Pat. No. 8,219,208, which is a continuation-in-part of application No. 12/489,921, filed on Jun. 23, 2009, now Pat. No.

(Continued)

(51) Int. Cl.
*A61N 1/36* (2006.01)
*A61N 1/05* (2006.01)
(Continued)

(52) U.S. Cl.
CPC . *A61N 1/05* (2013.01); *A61B 5/042* (2013.01); *A61B 5/055* (2013.01); *A61B 18/1492* (2013.01); *A61B 2018/00839* (2013.01); *A61B 2019/5236* (2013.01); *A61B 2562/182* (2013.01); *A61B 2562/222* (2013.01); *A61B 2562/227* (2013.01);
(Continued)

(58) Field of Classification Search
CPC ......... A61N 1/08; A61N 1/3718; A61N 1/05; A61N 1/056; A61N 1/086
USPC ............................................. 607/63, 115, 119
See application file for complete search history.

(56) References Cited

U.S. PATENT DOCUMENTS 5,209,233 A 5/1993 Holland et al.
6,529,000 B2 3/2003 Lou
(Continued)

OTHER PUBLICATIONS

European Search Report dated Jul. 22, 2013 for Application 13156198.7.
(Continued)

*Primary Examiner* — Christopher D Koharski
*Assistant Examiner* — Michael Carey
(74) *Attorney, Agent, or Firm* — Michael F. Scalise

(57) ABSTRACT

A composite RF current attenuator for a medical lead includes a conductor having a distal electrode contactable to biological cells, a bandstop filter in series with the lead conductor for attenuating RF currents flow through the lead conductor at a selected center frequency or across a range of frequencies about the center frequency, and a lowpass filter in series with the bandstop filter and forming a portion of the lead conductor. The bandstop filter has a capacitance in parallel with a first inductance. In a preferred form, the lowpass filter includes a second inductance in series with the bandstop filter, wherein the values of capacitance and inductances for the composite RF current attenuator are selected such that it attenuates MRI-induced RF current flow in an MRI environment.

61 Claims, 50 Drawing Sheets

Related U.S. Application Data 7,751,903, application No. 13/401,608, which is a continuation-in-part of application No. 13/299,278, filed on Nov. 17, 2011, now abandoned, and a continuation-in-part of application No. 12/891,292, filed on Sep. 27, 2010, now Pat. No. 8,437,865, and a continuation-in-part of application No. 12/686,137, filed on Jan. 12, 2010, and a continuation-in-part of application No. 12/607,234, filed on Oct. 28, 2009, now Pat. No. 8,175,700, and a continuation-in-part of application No. 12/407,402, filed on Mar. 19, 2009, now Pat. No. 8,195,295.

(60) Provisional application No. 61/149,833, filed on Feb. 4, 2009.

(51) Int. Cl.
| | |
|---|---|
| A61B 5/042 | (2006.01) |
| A61B 5/055 | (2006.01) |
| A61B 18/14 | (2006.01) |
| A61B 18/00 | (2006.01) |
| A61B 19/00 | (2006.01) |
| A61N 1/37 | (2006.01) |
| A61N 1/08 | (2006.01) |
| H03H 1/00 | (2006.01) |
| H03H 7/01 | (2006.01) |

(52) U.S. Cl.
CPC .......... *A61N 1/3718* (2013.01); *A61N 2001/086* (2013.01); *H03H 1/0007* (2013.01); *H03H 2001/0021* (2013.01); *H03H 2007/013* (2013.01)
USPC .............................. 607/63; 607/115; 607/119

(56) References Cited

U.S. PATENT DOCUMENTS

| | | |
|---|---|---|
| 7,155,271 B2 | 12/2006 | Halperin et al. |
| 7,363,090 B2 | 4/2008 | Halperin et al. |
| 7,689,288 B2 | 3/2010 | Stevenson et al. |
| 7,702,387 B2 | 4/2010 | Stevenson |
| 7,853,325 B2 | 12/2010 | Dabney |
| 7,920,910 B2 | 4/2011 | Calderon et al. |
| 2007/0112398 A1 | 5/2007 | Stevenson et al. |
| 2007/0288058 A1* | 12/2007 | Halperin et al. .................. 607/2 |
| 2008/0049376 A1 | 2/2008 | Stevenson et al. |
| 2008/0071313 A1 | 3/2008 | Stevenson et al. |
| 2008/0116997 A1 | 5/2008 | Dabney et al. |
| 2008/0132987 A1 | 6/2008 | Westlund et al. |
| 2008/0161886 A1 | 7/2008 | Stevenson et al. |
| 2008/0195180 A1 | 8/2008 | Stevenson |
| 2008/0269591 A1 | 10/2008 | Halperin |
| 2009/0099440 A1* | 4/2009 | Viohl ............................ 600/373 |
| 2009/0163981 A1 | 6/2009 | Stevenson et al. |
| 2010/0100164 A1 | 4/2010 | Johnson et al. |
| 2010/0191236 A1 | 7/2010 | Johnson et al. |
| 2010/0198312 A1 | 8/2010 | Stevenson |
| 2010/0217262 A1 | 8/2010 | Stevenson et al. |
| 2010/0280584 A1 | 11/2010 | Johnson |
| 2010/0324640 A1 | 12/2010 | Bauer |
| 2011/0046707 A1 | 2/2011 | Lloyd et al. |
| 2011/0196461 A1 | 8/2011 | Weiss et al. |
| 2012/0029342 A1 | 2/2012 | Kondabatni et al. |

OTHER PUBLICATIONS

European Search Report for EP Application 12 15 8261 dated Dec. 13, 2012.

\* cited by examiner

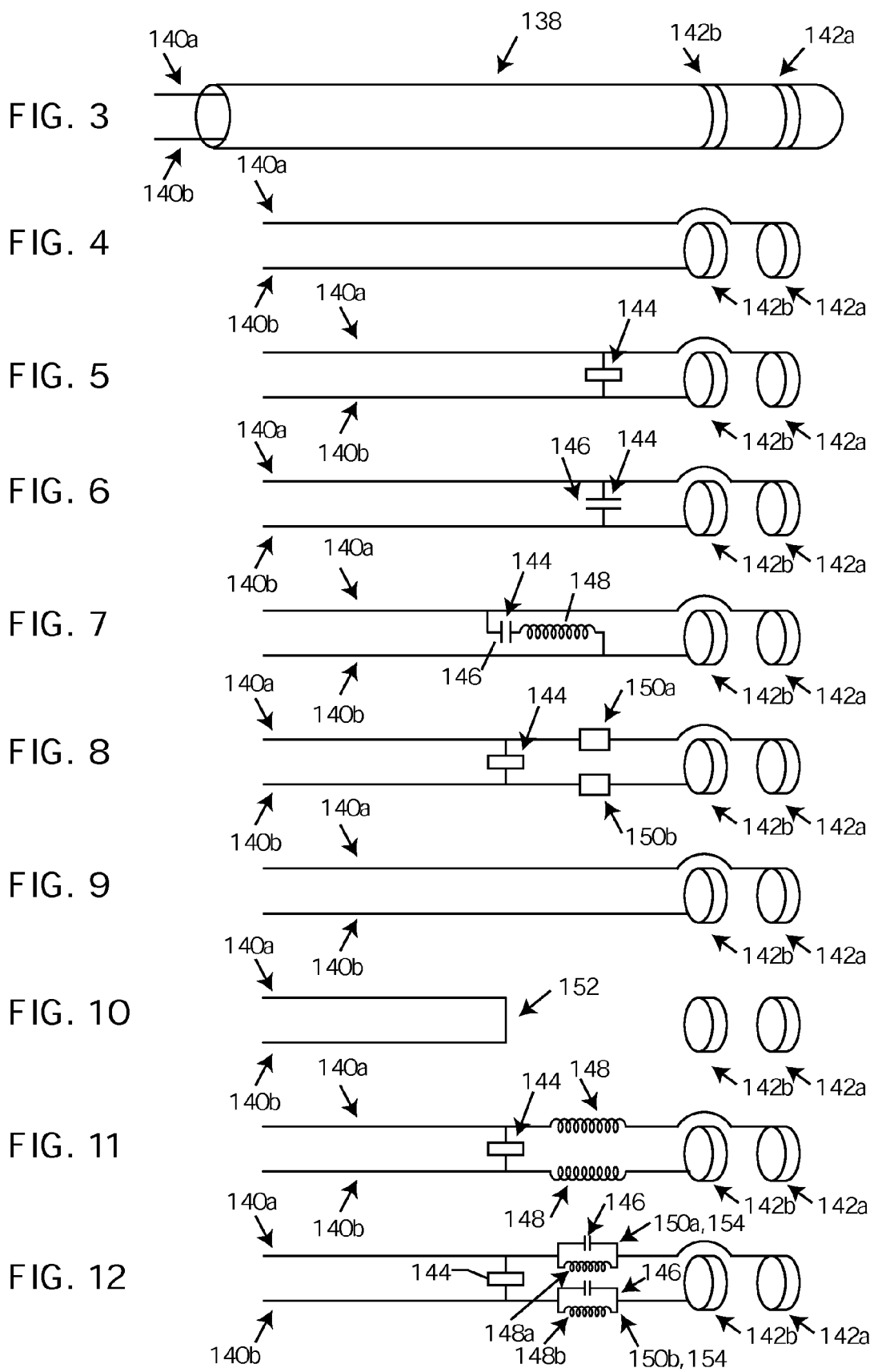

$$fr = \frac{1}{2\pi\sqrt{LC}}$$

Where: $fr$ = resonant frequency
$L$ = inductance in henries
$C$ = capacitance in farads Solving for C:

$$C = \frac{1}{(fr)^2 (2\pi)^2 L}$$

Solving for L:

$$L = \frac{1}{(fr)^2 (2\pi)^2 C}$$

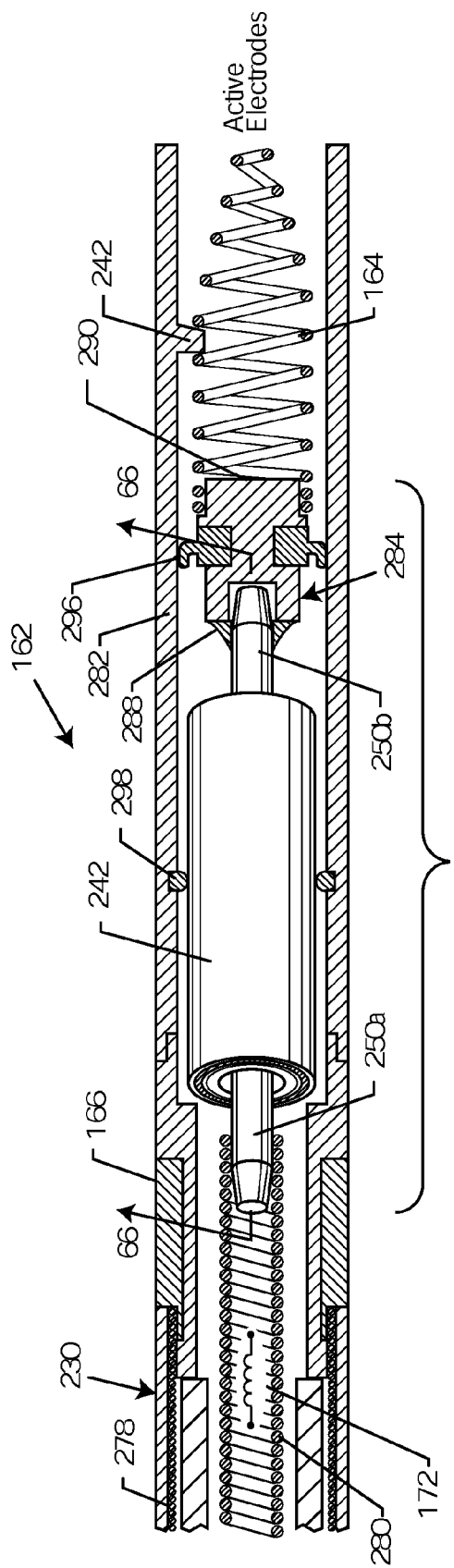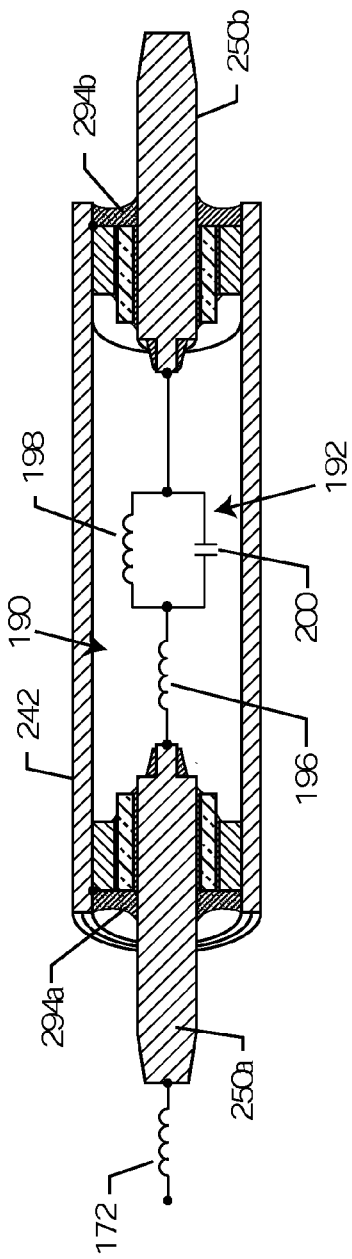
FIG. 65
FIG. 66

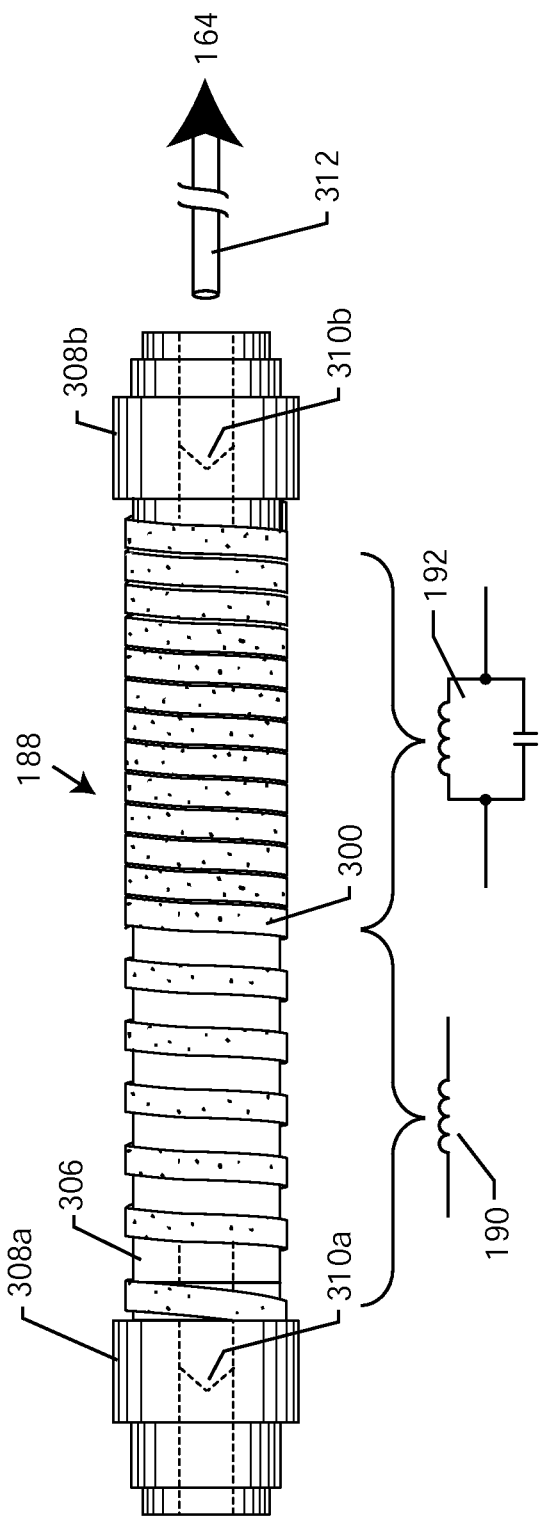
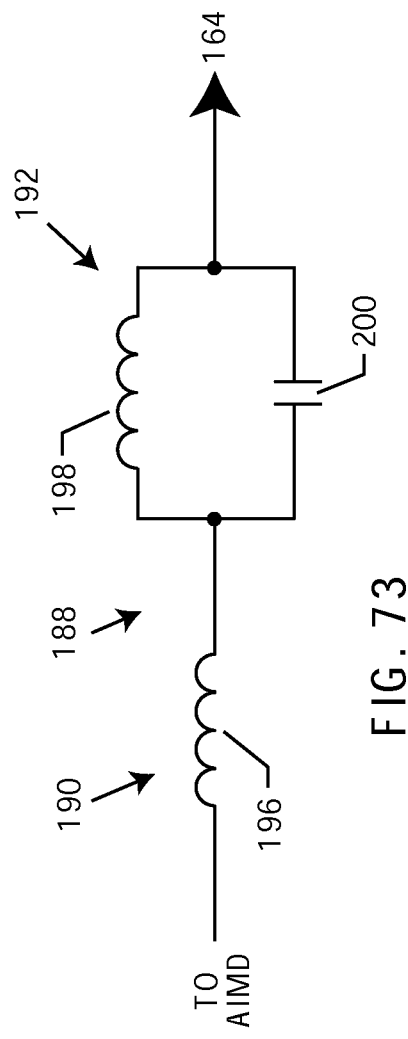
FIG. 72
FIG. 73

| French Guage | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |
| 13 | 4.3 | 0.170 |
| 14 | 4.7 | 0.184 |
| 15 | 5 | 0.197 |
| 16 | 5.3 | 0.210 |
| 17 | 5.7 | 0.223 |
| 18 | 6 | 0.236 |
| 19 | 6.3 | 0.249 |
| 20 | 6.7 | 0.263 |
| 22 | 7.3 | 0.288 |
| 24 | 8 | 0.315 |
| 26 | 8.7 | 0.341 |
| 28 | 9.3 | 0.367 |
| 30 | 10 | 0.393 |
| 32 | 10.7 | 0.419 |
| 34 | 11.3 | 0.455 |

FIG. 95

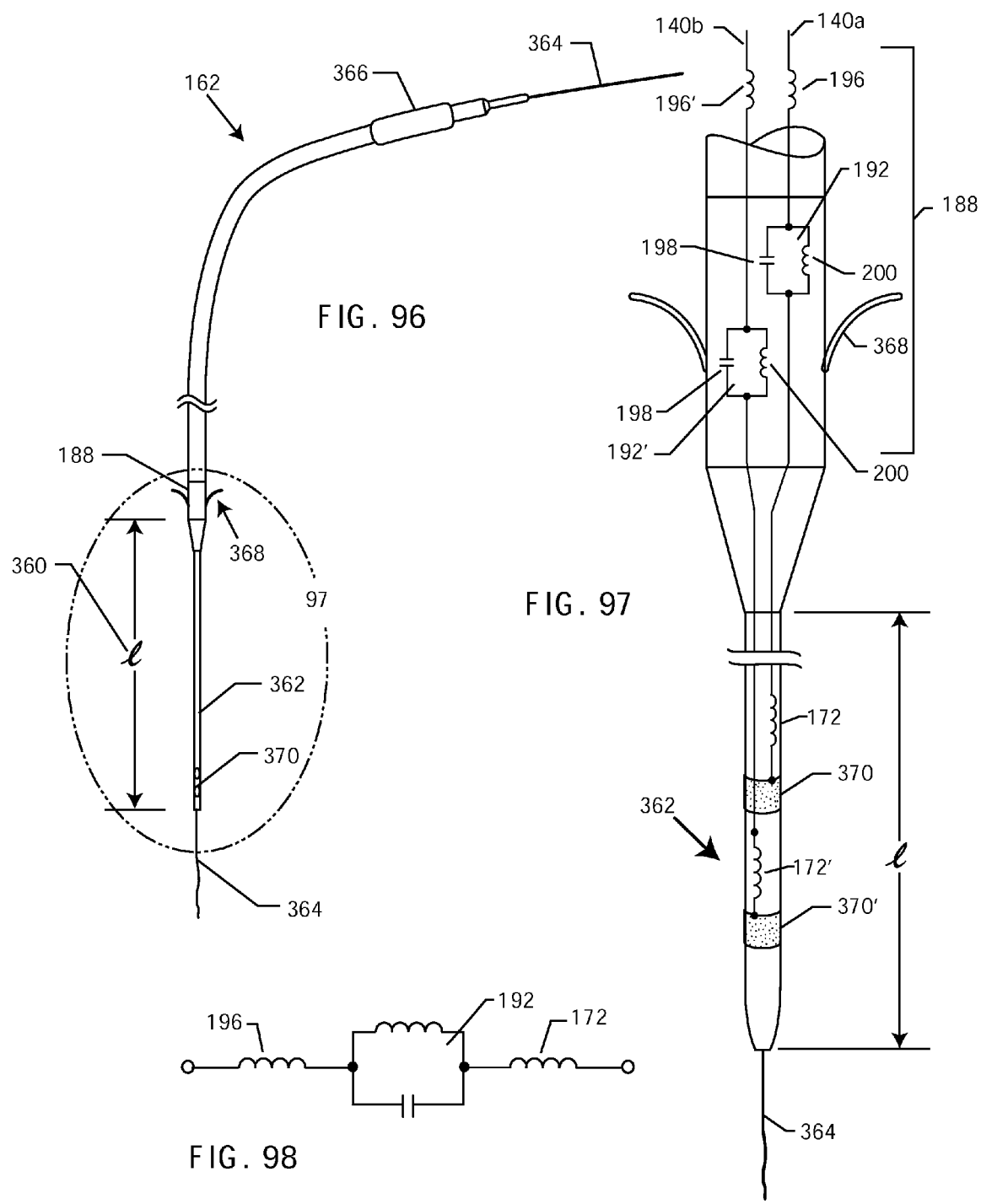

ns, Wiley, 1989;

COMPOSITE RF CURRENT ATTENUATOR FOR A MEDICAL LEAD

CROSS REFERENCE TO RELATED APPLICATIONS

This application claims priority to: continuation-in-part application of Ser. No. 12/751,711 filed on Mar. 31, 2010 now U.S. Pat. No. 8,219,208 which was itself a continuation-in-part application of Ser. No. 12/489,921 filed on Jun. 23, 2009 and issued as U.S. Pat. No. 7,751,903 on Jul. 6, 2010 and which claimed priority to provisional application 61/149,833 filed on Feb. 4, 2009; continuation-in-part of Ser. No. 12/686,137 filed on Jan. 12, 2010; continuation-in-part application of Ser. No. 13/299,278 filed on Nov. 17, 2011 now abandoned; continuation-in-part application of Ser. No. 12/407,402 filed on Mar. 19, 2009 now U.S. Pat. No. 8,195,295; continuation-in-part application of Ser. No. 12/607,234 filed on Oct. 28, 2009 now U.S. Pat. No. 8,175,700; and continuation-in-part application of Ser. No. 12/891,292 filed on Sep. 27, 2010 now U.S. Pat. No. 8,437,865; the contents of which all applications are fully incorporated herein with this reference and that of the application data sheet.

FIELD OF THE INVENTION

This invention relates generally to novel composite RF current attenuators for a medical lead comprising series lowpass and bandstop broadband filter assemblies, particularly of the type used in the implantable leads of active medical devices (AMDs) such as cardiac pacemakers, cardioverter defibrillators, neurostimulators, externally worn Holter monitors and the like. The bandstop filter portion of the composite RF current attenuator provides a very high impedance at the selected MRI RF center frequency and/or a range of frequencies about the center frequency. This works in concert with the composite lowpass filter which provides high impedance at higher MRI RF frequencies.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:

(1) "Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "I. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, U.S. Pub. No. 2003/0050557, now U.S. Pat. No. 7,844,319 to Susil et al.;
(7) Multifunctional Interventional Devices for MRI: A Combined Electrophysiology/MRI Catheter, by, Robert C. Susil, Henry R. Halperin, Christopher. Yeung, Albert C. Lardo and Ergin Atalar, MRI in Medicine, 2002; and
(8) Multifunctional Interventional Devices for Use in MRI, U.S. patent application Ser. No. 60/283,725, filed Apr. 13, 2001.
(9) Characterization of the Relationship Between MR-Induced Distal Tip Heating in Cardiac Pacing Leads and the Electrical Performance of Novel Filtered Tip Assemblies, by Robert S. Johnson, Holly Moschiano, Robert Stevenson, Scott Brainard, Sam Ye, Joseph E. Spaulding, Warren Dabney, $17^{th}$ Scientific Meeting & Exhibition of the International Society for Magnetic Resonance in Medicine, Honolulu, Hi., 18-24 Apr. 2009, Page No. 307.
(10) Comparative Analyses of MRI-Induced Distal Heating and Novel Filtered Cardiac Pacing Leads Using Two Geometric Configurations, by F. G. Shellock, Holly Moschiano, Robert Johnson, Robert Stevenson, Scott Brainard, Sam Ye and Warren Dabney, $17^{th}$ Scientific Meeting & Exhibition of the International Society for Magnetic Resonance in Medicine, Honolulu, Hawaii, 18-24 Apr. 2009, Page No. 3104.

The contents of the foregoing are all incorporated herein by reference.

However, an extensive review of the literature indicates that MRI is indeed often used with pacemaker, neurostimulator and other active medical device (AMD) patients. The safety and feasibility of MRI for patients with cardiac pacemakers is an issue of gaining significance. The effects of MRI on patients' pacemaker systems have only been analyzed retrospectively in some case reports. MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and perform MRI on a patient with an implanted pulse generator (IPG). The literature indicates a number of precautions that physicians should take in this case, including limiting the power of the MRI RF Pulsed field (Specific Absorption Rate—SAR level), programming the IPG to fixed or asynchronous pacing mode, and then careful reprogramming and evaluation of the device and patient after the procedure is complete. There have been reports of latent problems with cardiac pacemakers or other AMDs after an MRI procedure, sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. At the International Society for Magnetic Resonance in Medicine (ISMRM), which was held on 5 and 6 Nov. 2005, it was reported that field strengths of certain research MRI systems are increasing to levels as high as 11.7 Tesla. This is over 100,000 times the magnetic field strength of the earth. A static magnetic field can induce powerful mechanical forces and torque on any magnetic materials implanted within the patient. This would include certain components within an implanted device such as the cardiac pacemaker itself and or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to as much as 500 MHz, depending upon the static magnetic field strength. The frequency of the RF pulse varies with the field strength of the main static field where, for a hydrogen MRI scanner: RF PULSED FREQUENCY in MHz=(42.56)×(STATIC FIELD STRENGTH IN TESLA).

The third type of electromagnetic field is the time-varying magnetic gradient fields designated $G_x$, $G_y$, $G_z$, which are used for spatial localization. These change their strength along different orientations and operating frequencies on the order of 2-5 kHz. The vectors of the magnetic field gradients in the x, y and z directions are produced by three sets of orthogonally positioned coils and are switched on only during the measurements. In some cases, the gradient field has been shown to elevate natural heart rhythms (heart beat). This is not completely understood, but it is a repeatable phenomenon.

It is instructive to note how voltages and EMI are induced into an implanted lead wire system. At very low frequency (VLF), voltages are induced at the input to the cardiac pacemaker as currents circulate throughout the patient's body and create voltage drops. Because of the vector displacement between the pacemaker housing and, for example, the Tip electrode, voltage drop across the resistance of body tissues may be sensed due to Ohms Law and the circulating current of the RF signal. At higher frequencies, the implanted lead wire systems actually act as antennas where currents are induced along their length. These antennas are not very efficient due to the damping effects of body tissue; however, this can often be offset by extremely high power fields (such as MRI RF pulsed fields) and/or body resonances.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of the tissue, and the configuration of the anatomical region imaged. There are also a number of other variables that depend on the placement in the human body of the Active Implantable Medical Device (AIMD) and its associated lead wire(s). For example, the routing of the lead (right pectoral vs left pectoral, abdominal) and the lead length are also very critical as to the amount of induced current and heating that would occur. Also, distal Tip electrode design is very important as the distal Tip electrode itself can act as its own antenna wherein eddy currents can create heating. The cause of heating in an MRI environment is twofold: (a) RF field coupling to the lead can occur which induces significant local heating; and (b) currents induced between the distal Tip electrode and tissue during MRI RF pulse transmission sequences can cause local Ohms Law heating in tissue next to the distal Tip electrode of the implanted lead. The RF field of an MRI scanner can produce enough energy to induce lead wire currents sufficient to destroy some of the adjacent myocardial tissue. Tissue ablation has also been observed. The effects of this heating are not readily detectable by monitoring during the MRI. Indications that heating has occurred would include an increase in pacing threshold or loss of capture, venous ablation, Larynx or esophageal ablation, myocardial perforation and lead penetration, or even arrhythmias caused by scar tissue. Such long term heating effects of MRI have not been well studied yet for all types of AIMD lead wire geometries. There can also be localized heating problems associated with various types of electrodes in addition to Tip electrodes. This includes Ring electrodes or Pad electrodes. Ring electrodes are commonly used with a wide variety of implanted devices including cardiac pacemakers, neurostimulators, probes, catheters and the like. Pad electrodes are very common in neurostimulator applications. For example, spinal cord stimulators or deep brain stimulators can include a plurality of Pad electrodes to make contact with nerve tissue. A good example of this also occurs in a cochlear implant. In a typical cochlear implant there would be approximately 20 Ring electrodes that the physician places by pushing the electrode into the cochlea. Several of these Ring electrodes make contact with auditory nerves.

There are additional problems possible with implantable cardioverter defibrillators (ICDs). The programmable sensitivity in ICD biological sense circuits is normally much higher (more sensitive) than it is for pacemakers; therefore, ICDs may falsely detect a ventricular tachyarrhythmia and inappropriately deliver therapy. In this case, therapy might include anti-tachycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. Finally, in the presence of the main static field of the MRI the ferromagnetic core of this transformer tends to saturate thereby preventing the high voltage capacitor from fully charging up. This makes it highly unlikely that an ICD patient undergoing an MRI would receive an inappropriate high voltage shock therapy. While ICDs cannot charge during MRI due to the saturation of their ferro-magnetic transformers, the battery will be effectively shorted and lose life. This is a highly undesirable condition.

In summary, there are a number of studies that have shown that MRI patients with active medical devices, such as cardiac pacemakers, can be at risk for potential hazardous effects. However, there are a number of reports in the literature that MRI can be safe for imaging of pacemaker patients when a number of precautions are taken (only when an MRI is thought to be an absolute diagnostic necessity). These anecdotal reports are of interest, however, they are certainly not scientifically convincing that all MRI can be safe. As previously mentioned, just variations in the pacemaker lead wire length can significantly affect how much heat is generated. From the layman's point of view, this can be easily explained by observing the typical length of the antenna on a cellular telephone compared to the vertical rod antenna more common on older automobiles. The relatively short antenna on the cell phone is designed to efficiently couple with the very high frequency wavelengths (approximately 950 MHz) of cellular telephone signals. In a typical AM and FM radio in an automobile, these wavelength signals would not efficiently couple to the relatively short antenna of a cell phone. This is why the antenna on the automobile is relatively longer. An analogous situation exists with an AMD patient in an MRI system. If one assumes, for example, a 3.0 Tesla MRI system, which would have an RF pulsed frequency of 128 MHz, there are certain implanted lead lengths that would couple efficiently as fractions of the 128 MHz wavelength. It is typical that a hospital will maintain an inventory of various leads and that the implanting physician will make a selection depending on the size of the patient, implant location and other factors. Accordingly, the implanted or effective lead wire length can vary considerably. There are certain implanted lead wire lengths that do not couple efficiently with the MRI frequency and there are others that would couple very efficiently and thereby produce the worst case for heating.

The effect of an MRI system on the function of pacemakers, ICDs and neurostimulators depends on various factors, including the strength of the static magnetic field, the pulse sequence (gradient and RF field used), the anatomic region being imaged, lead length and trajectory, and many other factors. Further complicating this is the fact that each patient's condition and physiology are different and each manufacturer's IPGs behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, the physician with patient informed consent may make the decision to perform MRI in spite of all of the previously described attendant risks to the pacemaker system.

It is clear that MRI will continue to be used in patients with both external and active implantable medical devices. There are a number of other hospital procedures, including electrocautery surgery, lithotripsy, etc., to which a pacemaker patient may also be exposed. Accordingly, there is a need for AMD system and/or circuit protection devices which will improve the immunity of active medical device systems to diagnostic procedures such as MRI.

As one can see, many of the undesirable effects in an implanted lead system from MRI and other medical diagnostic procedures are related to undesirable induced currents in the conductor(s) of the lead system and/or its distal Ring electrode (or Ring). This can lead to overheating either in the lead or at the body tissue at the distal Ring electrode. For a pacemaker application, these currents can also directly stimulate the heart into sometimes dangerous arrhythmias.

MRI scanners that are commercially used in the market have evolved generally from 0.5 T to 1.5 T and higher. The most common systems in use today are 1.5 T and 3 T which have pulsed RF frequencies of 64 MHz and 128 MHz respectively. There are also a number of research machines that are evolving at 5 T, 7 T, 11 T and even higher. These would, of course, have higher RF pulse frequencies in accordance with the Lamour equation. For hydrogen scanners, the Lamour frequency which is equal to the MRI RF pulsed frequency is equal to 42.56 times the MRI scanner static magnetic field strength. For example for a 1.5 Tesla scanner, the RF field strength is 63.84 MHz. There are other types of scanners such as phosphorous scanners which would have different Lamour frequencies. There are a number of reasons why an active medical device patient may require MRI. These can range from neurologic disorders to cardiac disorders or to any type of soft tissue injury. 1.5 Tesla systems are fine for certain types of imaging, however, 3 T and higher can provide significantly improved imaging to diagnose a certain class of disorders. Accordingly, it is difficult to predict to what static magnetic field strength scanner an AIMD patient may eventually be exposed. In fact, over a patient's lifetime they may even have a need at one time to be scanned at 1.5 T and a later need to be scanned at 3 T.

There is a need for a composite RF current attenuator which can be placed at one or more locations along the active implantable medical device lead system, which presents a high impedance that prevents RF currents from circulating at selected frequencies of the MRI system. Preferably, such novel broadband MRI filters would be designed to provide a high impedance at 64 MHz (1.5 T), 128 MHz (3 T) and also at higher frequencies. The present invention fulfills these needs and provides other related advantages.

SUMMARY OF THE INVENTION

The present invention is directed to a medical lead comprising, generally, a conductor having a distal electrode contactable to biological cells, and a composite RF current attenuator which comprises at least a portion of the lead conductor. The composite RF current attenuator includes (1) a bandstop filter comprising at least a portion of the lead conductor for attenuating RF current flow through the lead conductor at a selected center frequency or across a range of frequencies, wherein the bandstop filter comprises a capacitance in parallel with a first inductance, said parallel capacitance and inductance placed in series with the lead conductor, wherein values of capacitance and inductance are selected such that the bandstop filter attenuates RF current flow at the selected center frequency or across the range of frequencies, and (2) a second inductance in series with the bandstop filter and comprising at least a portion of the lead conductor.

The lowpass filter preferably comprises a second inductance in series with the bandstop filter, which second inductance forms at least a portion of the lead conductor. The lowpass filter may further comprise an L filter, a T filter, a Pi filter, an LL filter, or an "n" element filter in series with the bandstop filter. The second inductance is preferably non-varying or stable and is equal to or greater than 16 nanohenries. In other embodiments, the second inductance is greater than or equal to 100 nanohenries, and in another embodiment is equal to or greater than 300 nanohenries. The second inductance may further comprise a plurality of second inductances of differing values along the length of the conductor.

The capacitance of the bandstop filter has an associated series resistance $R_C$, and the first inductance has an associated series resistance $R_L$.

In various embodiments, the capacitance may be formed by a discrete passive capacitor component, and the first and/or second inductance may be formed by a discrete passive inductor, including an inductor chip, an inductor winding, an inductor meander or an inductor trace. More particularly, the bandstop filter may be formed as at least a part of a coiled or spiraled inductor portion of the lead conductor, and the capacitance may be the parasitic capacitance formed between adjacent turns of said inductor portion. In this case, at least the coiled or spiraled inductor portion of the conductor is mechanically stable and insulated with a dielectric material having a dielectric constant greater than 1 and up to 100. The dielectric material may comprise polyimide, aromatic polyimide, liquid crystal polymer, PTFE, PEEK, ETFE, Parylene, tantalum oxides, iridium oxides, niobium oxides, hafnium oxides, ruthenium oxides, $SiO_2$, $Si_3N_4$, $Al_2O_3$, $Y_2O_3$, $La_2O_3$, $Ta_2O_5$, $TiO_2$, $HfO_2$, $ZrO_2$, any nano-dielectric coating, PFA, FEP, Polyurethane, polyurethane with self-bonding overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polyolefin class: {LDPE, HDPE, TPO, TPR, polyolefin alloys}, LDPE, HDPE, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, a crosslinked polyalkene, or any combinations thereof.

The range of selected frequencies may include a plurality of MRI RF-pulsed frequencies. Further, the composite RF current attenuator may be disposed at, adjacent to, or within the distal electrode, integrated into a Tip electrode, a Ring electrode, or at least partially housed within a heat dissipating shield or conductively coupled to an energy dissipating surface. In this latter case, a thermally conductive material is typically disposed between the composite EMI filter and the heat dissipating shield or the energy dissipating surface. The lowpass filter may include a capacitance connected to the heat dissipating shield or the energy dissipating surface. The heat dissipating shield or the energy dissipating surface may comprise a lead body, lead insulation, or a metallic energy dissipating surface in contact with body fluid or tissue.

The composite RF current attenuator may comprise any number of bandstop filters in combination with any number of lowpass filters in series with one another and comprising at least a portion of the lead conductor, in any order.

The composite RF current attenuator has a minimum impedance of 500 ohms at a first selected center frequency, and a minimum impedance of 500 ohms at a second selected center frequency. Preferably, the first selected center frequency is a first MRI RF pulsed frequency, and the second selected center frequency is a second MRI RF pulsed frequency. The second MRI RF pulsed frequency is resultant from a higher static magnetic field strength than the source for the first MRI RF pulsed frequency.

The medical lead may comprise an epicardial lead, a split-cylinder, a cuff electrode, a self-sizing nerve cuff, a multiple-cuff nerve electrode, a multiple bandstop filter array, a deep brain electrode, a paddle electrode, a Pad electrode, a deep brain stimulating array, a Ring electrode, an active fixation Tip electrode, a passive fixation Tip electrode, a lead extension electrode, a probe, a catheter or an ablation probe. Electrical insulation may be provided for preventing or inhibiting stray RF currents in the body fluids and tissues from degrading the impedance of the bandstop filter and/or the lowpass filter at resonance In the case where the bandstop filter is formed as at least a part of a coiled or spiral inductor portion of the lead conductor, and the capacitance is the parasitic capacitance formed between adjacent turns of said inductor portion, electrical insulation may be provided for preventing RF currents and body fluids or tissues from degrading the impedance of the lowpass filter or the bandstop filter at resonance. The electrical insulation typically comprises an insulative sleeve disposed about the coiled or spiral inductor portion of the conductor. The coiled or spiral inductor portion of the lead conductor may have separate distinct segments having different inductance and parallel capacitance values to form a plurality of bandstop filters which resonate at multiple different selected center frequencies. More specifically, the coiled or spiral inductor portion of the lead conductor may include distinct segments having different numbers of turns to form distinct bandstop filters which resonate at different selected center frequencies or across different ranges of frequencies.

The bandstop filter may include a central lumen to facilitate transvenous guide wire insertion. Similarly, the lowpass filter may include a central lumen to also facilitate transvenous guide wire insertion. The first and/or second inductances may be inherently derived from the lead's material of construction or structure. Similarly, the capacitance may be inherently derived from the lead's material of construction or structure.

The medical lead may comprise a proximal section and a distal reduced-diameter lead extension. In this case, the composite RF current attenuator is typically disposed at or near the proximal end of the lead extension. The composite RF current attenuator may include fixation tines, and the physical length of the lead extension will be less than ½ of the electrical wave length of the selected MRI RF center frequency, and more preferably, less than ⅛ of the electrical wave length of the selected MRI RF center frequency.

In another embodiment, the medical lead may comprise (1) a lead body adapted for in-vivo implantation in a living subject which comprises a proximal end configured for electrical and mechanical connection to a therapy delivering or monitoring device, and (2) a collar disposed at the distal end of the lead body, (3) a casing disposed within the collar and translatable along a longitudinal axis of the collar, (4) at least one electrical conductor extending substantially the length of the lead body, (5) at least one electronic component disposed within the casing and conductively coupled to the electrical conductor, (6) an electrode mechanically conducted to the casing and conductively coupled to the electronic component, and (7) a seal disposed between the casing and the collar for preventing passage of ionic fluid from the living subject into the lead body through its distal end. In this case, an insulative conformal coating comprised of a dielectric ceramic coating may be disposed about at least a portion of the casing. The composite RF current attenuator is disposed within the casing.

In yet another embodiment of the invention, the bandstop filter may comprise (1) an inductor having first and second conductive terminals in spaced non-conductive relation and (2) a capacitor having first and second conductive terminals in spaced non-conductive relation, wherein the inductor and the capacitor are physically disposed in series relative to one another, and wherein the inductor and the capacitor are electrically connected to one another in parallel. The lowpass filter is physically disposed in series with the inductor and the capacitor of the bandstop filter. One of the first or second conductive terminals of the inductor is typically disposed generally adjacent to one of the first or second conductive terminals of the capacitor. A capacitor and the inductor of the bandstop filter and the lowpass filter are aligned along a common axis such that the adjacent conductive terminals of the conductor and the capacitor abut one another. An electrical insulator is typically disposed between the adjacent conductive terminals of the inductor and the capacitor. The inductor may comprise a chip inductor, and the capacitor may comprise a chip capacitor. The second conductive terminal of the inductor may be conductively coupled to the first conductive terminal of the capacitor, and the first conductive terminal of the inductor may be conductively coupled to the second conductive terminal of the capacitor. In the preferred embodiment, the parallel capacitor and inductor are disposed in series with the conductor.

In yet another embodiment of the invention, the bandstop filter is formed as a multilayer helical wave filter and includes (1) a first helically wound segment having at least one planar surface, a first end and a second end, the first helically wound segment forming a first inductive component, (2) a second helically wound segment having at least one planar surface, a first end and a second end, the second helically wound segment forming a second inductive component, the first and second helically wound segments being wound in the same longitudinal direction and sharing a common longitudinal axis, wherein the at least one planar surface of the first helically wound segment faces the at least one planar surface of the second helically wound segment, (3) a return connecting segment extending substantially the length of the first and second helically wound segments to connect the second end of the first helically wound segment to the first end of the second helically wound segment, wherein the return connecting segment provides that current paths in the first and second helically wound segments will be in the same direction, and (4) a dielectric material disposed between the facing planar surfaces of the first and second helically wound segments, and between adjacent coils of the first and second helically wound segments, thereby forming a capacitance, wherein the wave filter has a primary resonance at the selected MRI pulsed frequency or frequency range. The elongated conductor may be coated with a dielectric material over all surfaces or sides. Further, the inductance created by the inductive components of the helical wave filter may be electrically disposed in parallel with the capacitance between the first and second helically wound segments.

The first inductance and/or the second inductance of the basic medical lead of the present invention may be formed from non-ferromagnetic materials. A third inductance may be provided in series with the bandstop filter and comprise at least a portion of the lead conductor.

Moreover, the basic medical lead of the present invention may include a second bandstop filter comprising at least a portion of the lead conductor, for attenuating RF current flow through the lead conductor at a second selective center frequency or across a second range of frequencies about the center frequency. In this case, the second bandstop filter comprises a second capacitance in parallel with a third inductance, said parallel capacitance and inductance placed in series with the lead conductor, wherein values of capacitance and inductance are selected such that the second bandstop filter attenuates RF current flow at the selected center frequency or across the second range of frequencies about the center frequency.

The bandstop filter may have an overall circuit Q wherein the resultant 3 dB bandwidth is at least 10 kHz, 100 kHz or 0.5 MHz or more. Moreover, the resultant 10 dB bandwidth may be at least 25 kHz, 200 kHz, 0.5 MHz, 10 MHz or more.

The $Q_I$ of the inductor portion may be inversely proportioned to the $Q_C$ of the capacitance to select the overall Q of the bandstop filter. The $Q_I$ of the inductor portion is increased by reducing resistive loss in the inductor portion and the $Q_I$ of the conductor portion is decreased by increasing resistive loss in the inductor. The $Q_C$ of the capacitance is reduced by raising the equivalence series resistance of the capacitance, and the $Q_C$ of the capacitance is increased by lowering the equivalent series resistance of the capacitance.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is a diagrammatic view of a typical probe or catheter;

FIG. 4 is an electrical diagrammatic view of the interior of the probe or catheter of FIG. 3;

FIG. 5 is an electrical diagrammatic view of the structure shown in FIG. 4, with a general impedance element connected between leads;

FIG. 6 is an electrical diagrammatic view similar to FIG. 5, illustrating a capacitor representing a frequency dependent reactive element between the leads;

FIG. 7 is a view similar to FIG. 6, wherein the general reactance element has been replaced by a capacitor in series with an inductor;

FIG. 8 is a view similar to FIGS. 5-7, showing the addition of series frequency selective reactances;

FIG. 9 is similar to FIG. 4, showing a low frequency model of the probe or catheter and associated leads shown in FIG. 3;

FIG. 10 is a view similar to FIGS. 4-9, illustrating how the distal rings may be electrically isolated at a high frequency;

FIG. 11 is a view similar to FIGS. 4-10, showing the addition of series inductor components added to the frequency selective elements;

FIG. 12 is similar to FIGS. 4-11, illustrating frequency selective elements which incorporate parallel resonant inductor and capacitor bandstop filters;

FIG. 65 is a sectional view of an exemplary medical electrical lead electrode assembly embodying the present invention;

FIG. 66 is an enlarged partially schematic sectional view taken along line 66-66 in FIG. 65;

FIG. 72 is an elevational view of a broadband inductor-parasitic capacitance bandstop filter disposed in series with an implanted lead conductor;

FIG. 73 is the electrical schematic of the broadband filter shown in FIG. 72;

FIG. 95 is a table showing the relationship between French sizes and millimeters and inches;

FIG. 96 is an enlarged perspective view of the lead system of FIG. 94;

FIG. 97 is an enlarged view of the distal lead taken generally of the area indicated by the line 97 in FIG. 96;

FIG. 98 is an electrical schematic of the inductor-bandstop filter-inductor composite RF current attenuator illustrated in FIG. 97;

DETAILED DESCRIPTION OF THE PREFERRED EMBODIMENTS

The present invention is directed to medical lead systems comprising an implantable lead having a proximal end and an electrode contactable to biological cells at a distal end. At least one broadband lowpass filter, such as an inductor is disposed in series with a bandstop filter and is associated with a lead conductor forming a composite RF current attenuator for attenuating current flow through the lead over a range of RF frequencies. In general, the broadband lowpass filter can consist of an inductor, L, LL, Pi, T-filter or multi-element filter or the like. The bandstop filter, which is in series with the lowpass filter, has an overall circuit Q wherein the resultant 3 dB bandwidth is at least 10 kHz and where the bandstop filter comprises a capacitance in parallel with an inductance, wherein values of capacitance and inductance are selected such that the bandstop filter is resonant at a selected center frequency. The selected center frequency is an MRI RF pulsed frequency.

As used herein, the term "bandwidth" refers to an attenuation or insertion loss plot measured (or calculated) in a balanced 50-ohm system (50-ohm source and load impedance). The best method is by swept measurements in a 50-ohm spectrum or network analyzer system with proper attention to "thru" and "short" calibrations. The most accurate measurements are of the bandstop filter portion of the lead which shows the performance of the bandstop filter versus frequency. It is best to measure bandstop filter bandwidth before the bandstop filter is installed into the implantable lead. Alternatively, the bandstop filter could be carefully removed (dissected) from the rest of the lead in order to perform the swept measurement. At its resonant center frequency, the bandstop filter has an attenuation peak. The bandwidth is the difference in frequency, either computed or measured, 3 dB or 10 dB down from the peak.

Throughout this detailed description, functionally equivalent elements may be referred to using the same or similar part numbers.

Figure 1:
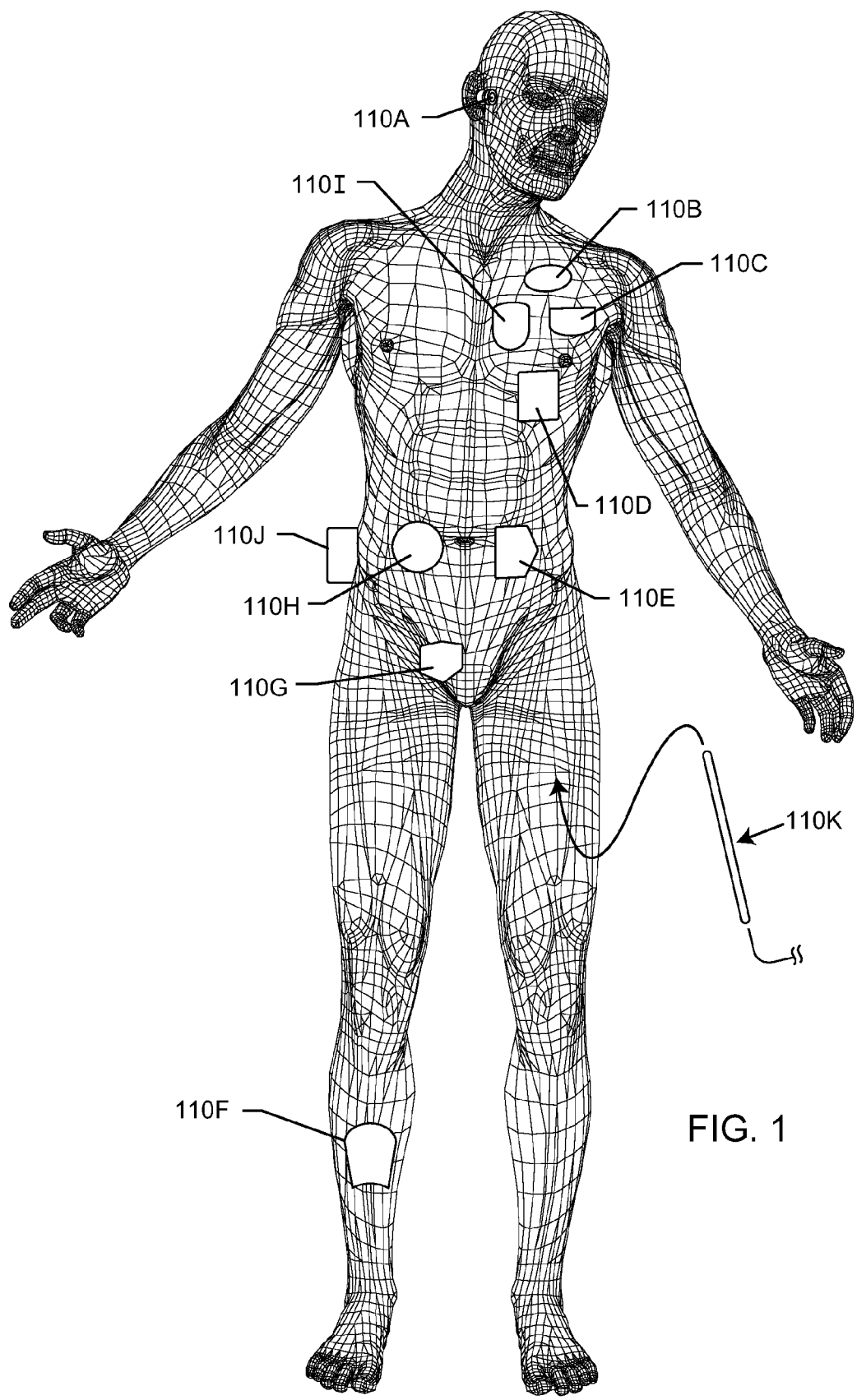
FIG. 1 is a wire-formed diagram of a generic human body showing a number of active medical devices (AMDs)

FIG. 1 illustrates various types of active implantable and external medical devices 110 that are currently in use. FIG. 1 is a wire formed diagram of a generic human body showing a number of implanted medical devices. 110A is a family of external and implantable hearing devices which can include the group of hearing aids, cochlear implants, piezoelectric sound bridge transducers and the like. 110B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. The lead wires that come from a deep brain stimulator are often placed using real time imaging. Most commonly such lead wires are placed during real time MRI. 110C shows a cardiac pacemaker which is well-known in the art. 110D includes the family of left ventricular assist devices (LVADs), and artificial hearts, including the recently introduced artificial heart known as the Abiocor. 110E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 110F includes a variety of external or implantable bone growth stimulators for rapid healing of fractures. 110G includes urinary incontinence devices. 110H includes the family of pain relief spinal cord stimulators and anti-tremor stimulators. 110H also includes an entire family of other types of neurostimulators used to block pain. 110I includes a family of implantable cardioverter defibrillator (ICD) devices and also includes the family of congestive heart failure devices (CHF). This is also known in the art as cardio resynchronization therapy devices, otherwise known as CRT devices. 110J illustrates an externally worn pack. This pack could be an external insulin pump, an external drug pump, an external neurostimulator, a Holter monitor with skin electrodes, a pulse oxygen monitor, or even a ventricular assist device power pack. 110K illustrates the insertion of an external probe or catheter. These probes can be inserted into the femoral artery, for example, or in any other number of locations in the human body.

Figure 2:
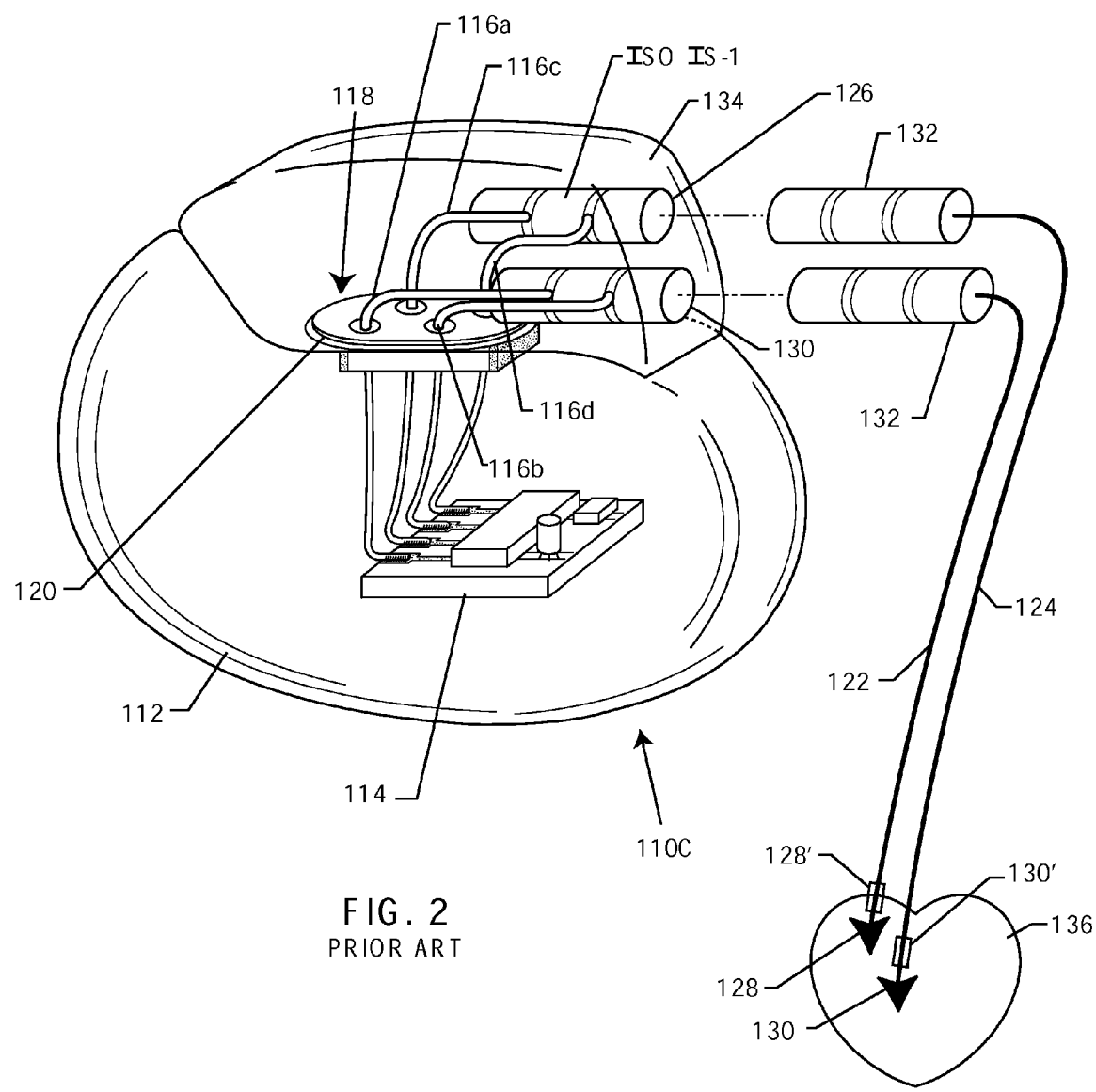
FIG. 2 is a perspective and somewhat schematic view of a prior art active implantable medical device (AIMD) including a lead directed to the heart of a patient.

In FIG. 2 a prior art active implantable medical device (AIMD) 110C is illustrated. In general, the AIMD 110C could, for example, be a cardiac pacemaker which is enclosed by a titanium or stainless steel conductive housing 112. The conductive housing 112 is hermetically sealed and contains a battery and electronic circuits 114; however, there is a point where conductors such as the illustrative conductors 116a, 116b, 116c, and 116d must ingress and egress in non-conductive relationship relative to the housing 112. This is accomplished by providing a hermetic terminal assembly 118. Hermetic terminal assemblies 118 are well known and generally consist of a ferrule 120 that is laser welded to the titanium housing 112 of the AIMD 110C. In FIG. 2, four conductive leadwires 116a-116d are shown for connection to a corresponding number of leads, such as the illustrative bipolar leads 122 and 124 shown for coupling to the connector receptacles 126 and 130. In this configuration, the two dual conductor leads are coupled respectively to the conductors 116a-116d to comprise a typical dual chamber bipolar cardiac pacemaker. It should be noted that each of the bipolar leads 122 and 124 have a pair of conductors associated with them. These are known as bipolar electrodes wherein one conductor is routed to a distal Tip electrode 128 and a second lead conductor is routed to a distal Ring electrode 128'. In a similar fashion, the other lead has a conductor that is routed to Tip electrode 130 and a second conductor that is routed to Ring electrode 130'.

Connectors 132 are commonly known as IS-1 connectors and are designed to plug into mating receptacles 126 on a header block 134 mounted on the pacemaker housing 112. These are low voltage (pacemaker) lead connectors covered by an International Standards Organization (ISO) standard IS-1. Higher voltage device connectors, such as implantable cardioverter defibrillators, are covered by a standard known as the ISO DF-1. A newer standard had been published that integrates both high voltage and low voltage connectors into a new miniature quadpolar connector series known as the ISO IS4 or DF4 standard. Leads plugged into these connectors are typically routed in a pacemaker or ICD application down into the right ventricle and right atrium of the heart 136. There are also new generation devices that have been introduced to the market that couple leads to the outside of the left ventricle. These are known as biventricular devices and are very effective in cardiac resynchronization therapy (CRT) and treating congestive heart failure (CHF).

It should be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as a probe, catheter or femoral artery ICD. Ventricular assist devices also can fall into this type of category. This list is not meant to be limiting, but is only example of the applications of the novel technology currently described herein. In the following description, functionally equivalent elements shown in various embodiments will often be referred to utilizing the same reference number.

FIG. 3 is a diagrammatic view of a typical prior art device 138 such as a probe or catheter or AIMD lead distal electrode. There are two conductors 140a and 140b which thread through the center of the illustrative probe or catheter and terminate respectively in a corresponding pair of distal conductive electrode rings 142a and 142b. Conductors 140a and 140b are electrically insulated from each other and are also electrically insulated from any metallic structures located within the catheter or lead body. The overall catheter or implanted lead body is generally flexible and is made of biocompatible materials, which also have specific thermal properties. In addition to flexibility, probes and catheters are typically steerable. It is well known that a push-pull wire (not shown in FIG. 3) can be run down the center of the catheter or probe in a lumen and then be attached to a catheter handle or pistol grip or other device so that the physician can carefully steer or thread the probe or catheter through the torturous path of the venous system, even into the ventricles of the heart. Such probes and catheters, for example, can be used for electrical mapping inside of a heart chamber, or for application of RF energy for ablation, which is used to treat certain cardiac arrhythmias. Probes and catheters have wide application to a variety of other medical applications. There are also combined catheters that can do electrical mapping and can also perform RF ablation. When the physician finds the area of arrhythmic electrical activity and wishes to ablate, he activates a switch which applies RF energy to the tip of the catheter (see, e.g., FIG. 48, which will be discussed herein in more detail). This would involve a third electrode right at the catheter tip of FIG. 3 (not shown). It would be extremely valuable if the catheter could be guided during real-time MRI imaging. This is important because of MRI's incredible ability to image soft tissue. In addition, when one is doing deliberate ablation, for example, around a pulmonary vein, it is important that a full circle of scar tissue be formed, for example, to stop atrial fibrillation. MRI has the ability to image the scar as it is being formed (for example, see U.S. Pat. No. 7,155,271). However, it would be highly undesirable if the MRI RF energy that is coupled to the conductors caused the distal ablation tip or the electrode rings to overheat at an improper time, which could burn or ablate healthy tissues.

FIG. 4 shows the interior taken from FIG. 3 showing conductors 140a and 140b which are routed to the two distal electrodes 142a and 142b as previously described in FIG. 3.

FIG. 5 shows the electrical circuit of FIG. 4 with a general frequency selective reactive diverting element 144 connected between conductors 140a and 140b. In the present invention, the diverting element 144 can consist of a number of frequency selective elements as will be further described. In general, the first conductor 140a is electrically coupled to the first electrode 142a, the second conductor 140b is electrically coupled to the second electrode 142b, and the frequency dependent reactive diverting element 144 electrically couples the first and second conductors 140a and 140b such that high frequency energy is conducted or diverted between the first conductor 140a and the second conductor 140b.

Referring once again to FIG. 5, the frequency selective reactive diverting element 144 tends to be electrically invisible (i.e., a very high impedance) at selected low frequencies. The reactive element is desirably selective such that it would not attenuate, for example, low frequency biological signals or RF ablation pulses. However, for high frequency MRI RF pulsed frequencies (such as 64 MHz), this frequency reactive diverting element 144 would look more like a short circuit. This would have the effect of sending the energy induced into the conductors 140a and 140b by the MRI RF field back into the catheter body and energy dissipating surface into which the conductors are embedded. In other words, there are desirably both RF energy and thermal conductivity to the probe or catheter body or sheath or shield which becomes an energy dissipating surface all along the lengths of conductors 140a and 140b such that MRI induced energy that is present in these conductors is diverted and converted to heat into the interior and along the catheter body itself. This prevents the heat build up at the extremely sensitive locations right at the ring electrodes 142a and 142b which are in intimate and direct contact with body tissue. In addition, the amount of temperature rise is very small (just a few degrees) because of the energy being dissipated over such a relatively high surface area. As previously mentioned, the high frequency RF pulsed energy from an MRI system can couple to the conductors of implanted leads. This creates electromagnetic forces (EMFs) which can result in current flowing through the interface between electrodes that are in contact with body tissue. If this current reaches sufficient amplitude, body tissue could be damaged by excessive RF current flow or heat build-up. This can create scar tissue formation, tissue damage or even tissue necrosis to the point where the AIMD can no longer deliver appropriate therapy. In certain situations, this can be life threatening for the patient.

FIG. 6 shows a capacitor 146 which represents one form of the frequency selective diverting reactive element 144 previously described in connection with FIG. 5. In this case, the reactive element comprises a simple capacitor 146 connected between the first conductor 140a and the second conductor 140b and will have a variable impedance vs. frequency. The following formula for capacitive reactance is well known in the art: $X_C=1/(2\pi fc)$. Referring to the foregoing equation, one can see that since frequency (f) is in the denominator, as the frequency increases, the capacitive reactance in ohms decreases. With a large number in the denominator, such as the RF pulsed frequency of a 1.5 Tesla MRI system, which is 64 MHz, the capacitive reactance drops to a very low number (essentially a short circuit). By shorting the conductors 140a and 140b together at this one frequency, this diverts and prevents the RF energy from reaching the distal ring electrodes 142a and 142b and being undesirably dissipated as heat into body tissue. Referring once again to FIG. 5, one can see that the frequency selective diverting element 144 thereby diverts the high frequency RF energy back into the catheter or AIMD lead conductors 140a and 140b. By spreading this energy along the length of conductors 140a and 140b, it is converted to heat, which is dissipated into the main body of the probe, catheter or energy dissipating sheath. In this way, the relatively large thermal mass of the probe or catheter becomes an energy dissipating surface and any temperature rise is just a few degrees C. In general, a few degrees of temperature rise is not harmful to body tissue. In order to cause permanent damage to body tissue, such as an ablation scar, it generally requires temperatures above 20° C. In summary, the frequency selective reactive element 144, which may comprise a capacitor 146 as shown in FIG. 5, forms a diversion circuit such that high frequency energy is diverted away from the distal electrodes 142a and 142b along the conductors 140a and 140b to a surface that is distant from the electrodes 142a and 142b, at which point the energy is converted to heat.

FIG. 7 shows a different way of diverting high frequency energy away from the electrodes 142a, 142b and accomplishing the same objective. The general diverting reactance element 144 described in FIG. 5 is shown in FIG. 7 to comprise a capacitor 146 in series with an inductor 148 to form an L-C trap circuit. For the L-C trap, there is a particular frequency ($f_r$) at which the capacitive reactance $X_C$ and the inductive reactance $X_L$ are vectorally equal and opposite and tend to cancel each other out. If there are no losses in such a system, this results in a perfect short circuit between the conductors 140a and 140b at the resonant frequency. The frequency of resonance of the trap filter is given by the equation $$f_r = \frac{1}{2\pi\sqrt{LC}},$$

wherein $f_r$ is the frequency of resonance in Hertz, L is the inductance in henries, and C is the capacitance in farads.

FIG. 8 illustrates any of the aforementioned frequency dependent diverting impedance elements 144 with the addition of series frequency selective impeding reactances 150a and 150b. The addition of series impedance further impedes or blocks the flow of high frequency MRI induced currents to the ring electrodes 142a and 142b as will be more fully described in the following drawings.

FIG. 9 is the low frequency model of FIG. 5, 6 or 7. In this regard, FIG. 9 is identical to FIG. 4 in that, once again, it shows the electrical leads 140a and 140b connected to the distal ring electrodes 142a and 142b of the probe or catheter 138. In the low frequency model, the frequency reactive diverting impedance elements 144 disappear because at low frequency their impedances approach infinity. Of course, elongated conductors in a probe or catheter are electrically and functionally equivalent to leads used for cardiac pacemakers, implantable cardioverter defibrillators, neurostimulators and the like. For example, reference is made to U.S. Pat. No. 7,363,090, the contents of which are incorporated herein. Accordingly, any discussion herein related to probes or catheters apply equally to leads and lead conductors for all active implantable medical devices as shown in FIG. 1, and vice versa. Referring once again to FIG. 9, at low frequency, the frequency selective or reactive diverting component 144 tends to look like a very high or infinite impedance. At low frequency, the series reactive or frequency variable impeding elements 150a and 150b tend to look like a very low impedance or short circuit. Accordingly, they all tend to disappear as shown in FIG. 9.

FIG. 10 is a high frequency model that illustrates how the distal electrodes or rings 142a and 142b are electrically isolated at high frequency by shorting conductors 140a and 140b at location 152. As previously mentioned, such shorting or current diverting could be accomplished by a direct short, a capacitor, a capacitive lowpass filter or a series resonant L-C trap circuit. FIG. 10 also shows the electrodes 142a and 142b as cut or disconnected and electrically isolated from the rest of the circuit. This is because at very high frequency, series impeding elements 150a and 150b tend to look like a very high impedance or an open circuit. In summary, by reactive elements 144, 150a and 150b acting cooperatively, reactive element 144 diverts the high frequency energy back into energy dissipating surfaces in the probe or the catheter or the device lead while at the same time reactive elements 150a and 150b impede the high frequency RF energy. Accordingly in the ideal case, at high frequencies, the equivalent circuit of FIG. 10 is achieved. Accordingly, excessive high frequency MRI RF energy cannot reach the distal ring electrodes 142a, 142b and cause undesirable heating at that critical tissue interface location.

FIG. 11 shows any of the previously described diverting frequency selective impedance elements 144 in combination with series reactance components 148a and 148b shown in the form of a pair of inductors. It is well known to electrical engineers that the inductive reactance in ohms is given by the equation $X_L=2\pi fL$. In this case the frequency term (f) is in the numerator. Accordingly, as the frequency increases, the reactance (ohms) of the inductors also increases. When the frequency is very high (such as 64 MHz) then the reactance in ohms becomes extremely high (ideally approaches infinity and cuts off the electrodes). By having a short circuit or very low impedance between the conductors 140a and 140b, and the probe/catheter body and then, at the same time, having a very high impedance in series with the electrodes from inductors 148a and 148b, this provides a very high degree of attenuation to MRI RF pulsed frequencies thereby preventing such energy from reaching the distal ring electrodes 142a and 142b. In FIG. 11, the line-to-line selective impedance element 144 diverts high frequency energy back into conductors 140a and 140b while at the same time the series inductors 148a and 148b impede (or cut-off) high frequency energy. When the line-to-line element 144 is a capacitor 146 as shown in FIG. 6, then this forms what is known in the prior art as an L section lowpass filter, wherein the capacitor 146 electrically cooperates with the inductors 148a and 148b (FIG. 11) to form a 2-element lowpass filter. By definition, a lowpass filter allows low frequencies such as biological signals to pass to and from the distal electrodes freely with insignificant attenuation while at the same time provides a high degree of attenuation to undesirable high frequency RF energy. It will be apparent to those skilled in the art that FIG. 6 shows a single element (capacitor) lowpass filter, and that FIG. 11 describes a 2-element or L-section lowpass filter. Moreover, any number of inductor and capacitor combinations can be used for lowpass filters, including 3-element Pi or T circuits, LL, 5-element or even "n" element filters.

FIG. 12 offers an even greater performance improvement over that previously shown and described in connection with FIG. 11. In FIG. 12, modified frequency selective impeding elements 150a and 150b each incorporate a parallel resonant inductor 148 and capacitor 146 which is also known in the industry as a bandstop filter. The L-C components for each of the reactive elements 146 and 148 are carefully chosen such that each of the bandstop filters 150a and 150b is resonant, for example, at the pulsed resonant frequency of an MRI scanner. For common hydrogen scanners, the pulsed resonant frequency of an MR scanner is given by the Lamour equation wherein the RF pulsed frequency in megahertz is equal to 42.56 times the static field strength. For example, for a popular 1.5 Tesla scanner, the RF pulsed frequency is approximately 64 MHz. Common MR scanners that are either in use or in development today along with their RF pulsed frequencies include: 0.5 Tesla-21 MHz; 1.5 Tesla-64 MHz; 3 Tesla-128 MHz; 4 Tesla-170 MHz; 5 Tesla-213 MHz; 7 Tesla-300 MHz; 8 Tesla-340 MHz; and 9.4 Tesla-400 MHz. When the bandstop filters, shown as impeding elements 150a and 150b, are resonant at any one of these RF pulsed frequencies, then these elements tend to look like an open circuit which impedes the flow of RF current to distal electrodes. When compatibility with different types of MR scanners is required, for example, 1.5, 3 and 5 Tesla, then three separate bandstop filter elements in series may comprise the reactive element 150a (FIG. 8), and three separate bandstop filter elements in series may comprise the impeding element 150b (FIG. 8). Each of these would have their L and C components carefully selected so that they would be resonant at different frequencies. For example, in the case of MR scanners operating at 1.5, 3 and 5 Tesla, the three bandstop filters comprising the impeding element as well as the three bandstop filters comprising the reactive element would be resonant respectively at 64 MHz, at 128 MHz, and at 170 MHz. The resonant frequencies of the bandstop filter elements 154 could also be selected such that they are resonant at the operating frequency of other emitters that the patient may encounter such as diathermy and the like. The use of bandstop filters is more thoroughly described in U.S. Pat. No. 7,363,090 and Patent Publication Nos. US 2007/0112398 A1; US 2007/0288058; US 2008/0071313 A1; US 2008/0049376 A1; US 2008/0161886 A1; US 2008/0132987 A1 and US 2008/0116997 A1, the contents of which are incorporated herein.

Figure 13:
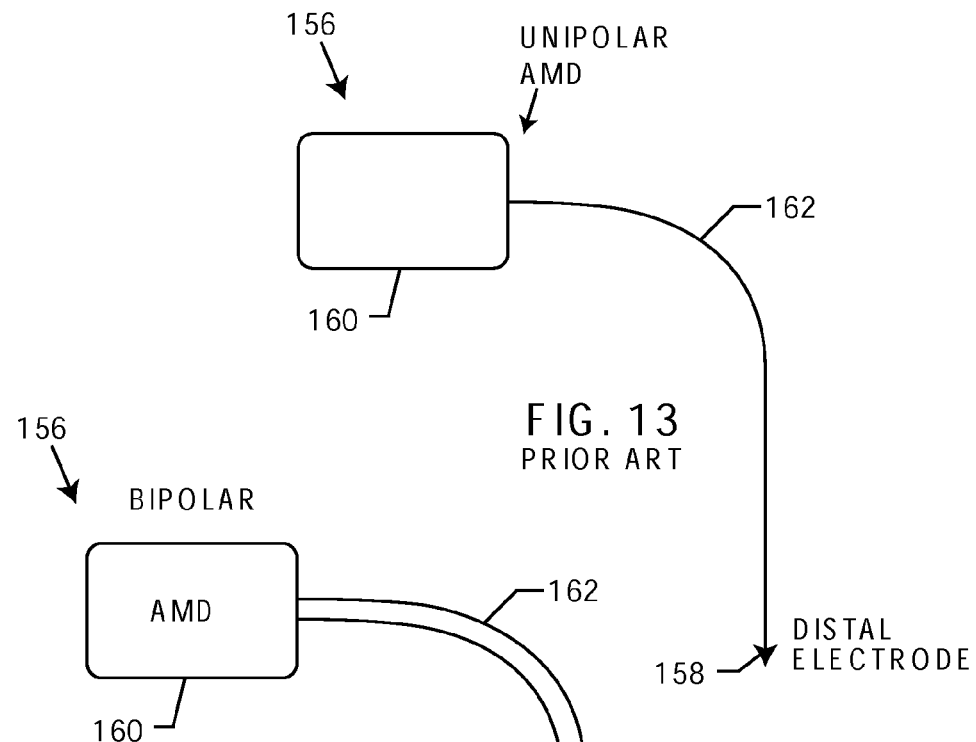
FIG. 13 is a schematic diagram of a unipolar active medical device.

FIG. 13 is a general diagram of a unipolar active medical device (AIMD) system 156. FIG. 13 could also be representative of an externally worn medical device such as a Holter monitor 110j. In the case of a Holter monitor 110j, the distal electrode 158 would typically be a scan or patch electrode. The housing 160 of the active medical device 156 is typically titanium, ceramic, stainless steel or the like. Inside of the device housing 160 are the AMD electronic circuits. Usually AMDs (particularly the type of AMD known as an active "implantable" medical device (AIMD)) include a battery, but that is not always the case. For example, for a Bion, it can receive its energy from an external pulsing magnetic field. A unipolar lead with a single conductor 162 is routed from the AMD 156 to a point 158 where it is embedded in or affixed to body tissue. In the case of a spinal cord stimulator 110H, the distal electrode 158 could be in the spinal cord. In the case of a deep brain stimulator 110B, the distal electrode 158 would be placed deep into the brain, etc. In the case of a cardiac pacemaker 110C, the distal electrode 158 would typically be placed in the cardiac right ventricle.

Figure 14:
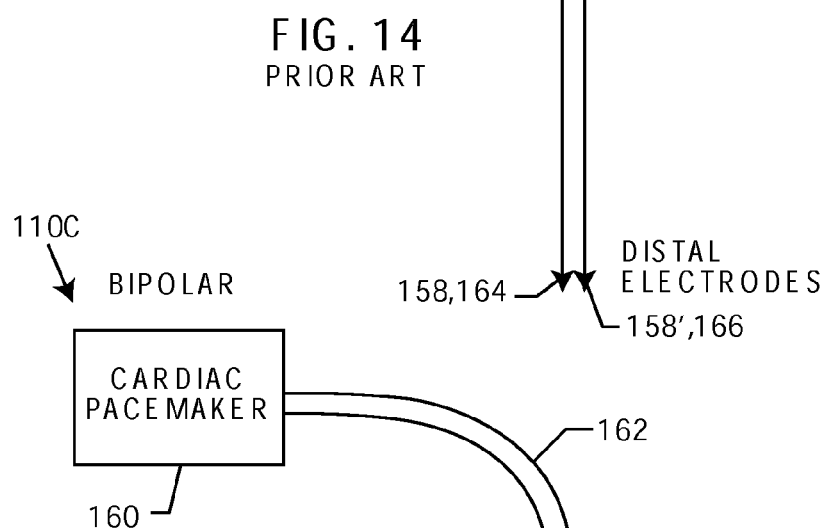
FIG. 14 is a diagram similar to FIG. 13, illustrating a bipolar AMD system.

FIG. 14 is very similar to FIG. 13 except that it is a bipolar system. In this case, the electric circuit return path is between the two distal electrodes 158 and 158'. In the case of a cardiac pacemaker 110C, this would be known as a bipolar lead system with one of the electrodes known as the distal Tip electrode 164 and the other electrode which would float in the blood pool known as the Ring electrode 166 (see FIG. 10). In contrast, the electrical return path in FIG. 13 is between the distal electrode 158 through body tissue to the conductive housing 160 of the active medical device 156.

Figure 15:
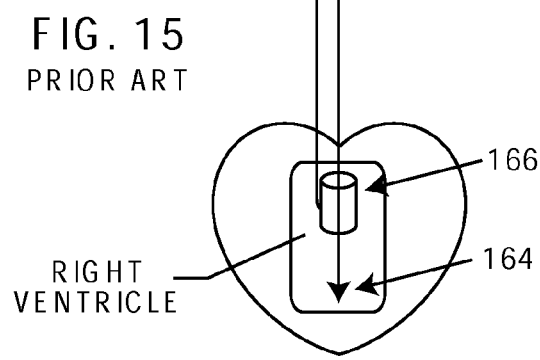
FIG. 15 is a diagram similar to FIGS. 13 and 14, illustrating a bipolar lead wire system with distal Tip and Ring electrodes, typically used in a cardiac pacemaker.

FIG. 15 illustrates a bipolar lead system with a distal Tip electrode 164 and a Ring electrode 166 typically as used in a cardiac pacemaker 110C. In all of these applications, the patient could be exposed to the fields of an MRI scanner or other powerful emitter used during a medical diagnostic procedure. Currents that are directly induced in the lead system 162 can cause heating by $I^2R$ losses in the lead system or by heating caused by current flowing in body tissue. If these currents become excessive, the associated heating can cause damage or even destructive ablation to body tissue.

The distal Tip electrode 164 is designed to be implanted into or affixed to the myocardial tissue of the heart. The Ring electrode 166 is designed to float in the blood pool. Because the blood is flowing and is thermally conductive, the Ring electrode 166 structure is substantially cooled. However, if the lead curves, the Ring electrode 166 could also touch and become encapsulated by body tissue. The distal Tip electrode 164, on the other hand, is always thermally insulated by surrounding body tissue and can readily heat up due to the RF pulse currents of an MRI field.

Figures 16, 17:
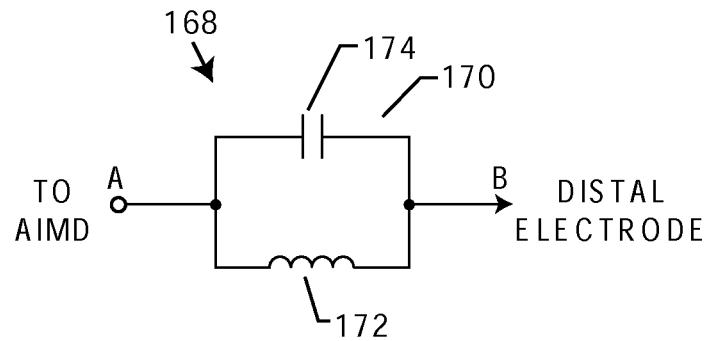
FIG. 16 is an electrical schematic illustration for a bandstop filter.
FIG. 17 is a formula for calculating frequency of resonance for the parallel bandstop filter circuit of FIG. 16.

FIG. 16 is a schematic diagram of a prior art parallel inductor-capacitor bandstop filter 168 comprising a bandstop circuit 170 having an inductor 172 and a capacitor 174 arranged in parallel. Bandstop filters for implantable leads of AIMDs are more thoroughly described in U.S. Pat. No. 7,363,090, the contents of which are incorporated herein by reference. Bandstop filters provide a very high impedance over a range of frequencies that are centered on a resonant center frequency. In this regard, they are very useful for providing attenuation to induced RF currents from a particular type of MRI scanner. For example, a 1.5 Tesla MR scanner has an RF pulsed frequency, which is determined by the Lamour Equation, which is 42.56× the static magnetic field strength. For a 1.5 Tesla scanner, the RF frequency is therefore approximately 64 MHz. When one designs that bandstop filter circuit of FIG. 16 to be resonant around a 64 MHz center frequency, the bandstop filter can provide a very high impedance (>1000 ohms). This high impedance inhibits the flow of RF current into an implanted lead conductor and/or distal electrode, which can be damaging to sensitive body tissues.

FIG. 17 gives the frequency of resonance equation $f_r$ for the parallel bandstop circuit 170 of FIG. 16: where $f_r$ is the frequency of resonance in hertz, L is the inductance 172 in henries and C is the capacitance 174 in farads.

It is a principle of the present invention that the bandstop filter can be realized by coils of wire and parasitic capacitance or by placing discrete inductors in parallel with discrete capacitors. One example would be to place a wire wound chip inductor in parallel with a monolithic ceramic capacitor. On the other hand, bandstop filters can also be realized in the present invention by carefully controlling the turns, pitch and dielectric insulation of a coiled or helical lead conductor such that its parasitic inductance is resonant with its parasitic capacitance at a selected MRI RF frequency.

The relationship between the parallel inductance 172 and capacitance 174 is very important. One could use a very large value of inductance 172 which would result in a very small value of capacitance 174 to be resonant, for example, at the MRI frequency of 64 MHz. However, using a very high value of inductance 172 results in a high number of turns (coils) of very small wire. Using a high number of turns of very small diameter wire has to be done carefully for two reasons. The first reason is that the long length of relatively small diameter wire results in a very high resistance for the inductor. This resistance has to be limited because low frequency pacing or neurostimulator pulses would lose energy passing through the relatively high series resistance. Too much resistance is undesirable where the AMD is sensing biologic signals. For example, in the case of a pacemaker or deep brain stimulator, continuous sensing of low frequency biological signals is required. Too much series resistance in a lead conductor will attenuate such signals thereby making the AMD less efficient. In one embodiment, an inductance 172 on the order of 200 nanohenries is used in parallel with a capacitance 174 of 15 to 20 picofarads to create a broadband filter at 64 MHz. At resonance, RF currents circulate back and forth between the inductance 172 and the capacitance 174 of the bandstop circuit 170 at the MRI RF pulsed frequency. In other words, for a 1.5 Tesla MRI scanner, at 64 million times per second, the capacitor 174 discharges into the inductive field of the inductor 172 and then reverses wherein the inductive field of the inductor 172 collapses into the electric field of the capacitor 174. This current passes back and forth in the bandstop circuit 170 through the resistance of the inductor 172 and the high frequency equivalent series resistance (ESR) of the capacitor 174. Because of these resistances, this circulating current in the bandstop circuit 170 can cause it to heat up. Accordingly, in a preferred embodiment, the bandstop filter 168 is shielded wherein the shield can dissipate heat generated in the bandstop filter 168 into surrounding body fluids or tissues over a relatively large surface area.

It should be also noted that below resonance, particularly at very low frequencies, the implantable lead pacing pulses or biological signals pass through the inductor element 172 of the parallel L-C bandstop filter 168. Accordingly, it is important that the parasitic resistance of the inductor 172 not be excessive. Conversely, at very low frequencies, no current passes through the capacitor element 174. At very high frequencies (greater than 1000 MHz), the reactance of the capacitor element 174 drops to a very low value. However, as there is no case where it is actually desirable to have high frequencies pass through the bandstop filter 168, the parasitic resistive loss of the capacitor 174 is not particularly important. This is also known as the capacitor's 174 equivalent series resistance (ESR). A component of capacitor ESR is the dissipation factor (dielectric loss tangent) of the capacitor 174. Off of resonance, it is not particularly important how high the capacitor's dissipation factor or overall ESR is when used as a component of a parallel bandstop circuit 170 as described herein. Accordingly, an air core wound solenoid-type inductor (which can be coils of the lead conductor) is the ideal choice because it is not affected by MRI signals or fields. As used herein, "air wound" means that there is no ferromagnetic core for the inductor such as a ferrite toroid, slug or cylinder. Because of the space limitations, however, the air wound coil inductor will not be very volumetrically efficient. For this reason, and due to size limitations, it is preferable to keep the inductance value relatively low (typically in the range of 1 to 500 nanohenries).

Figures 18, 19:
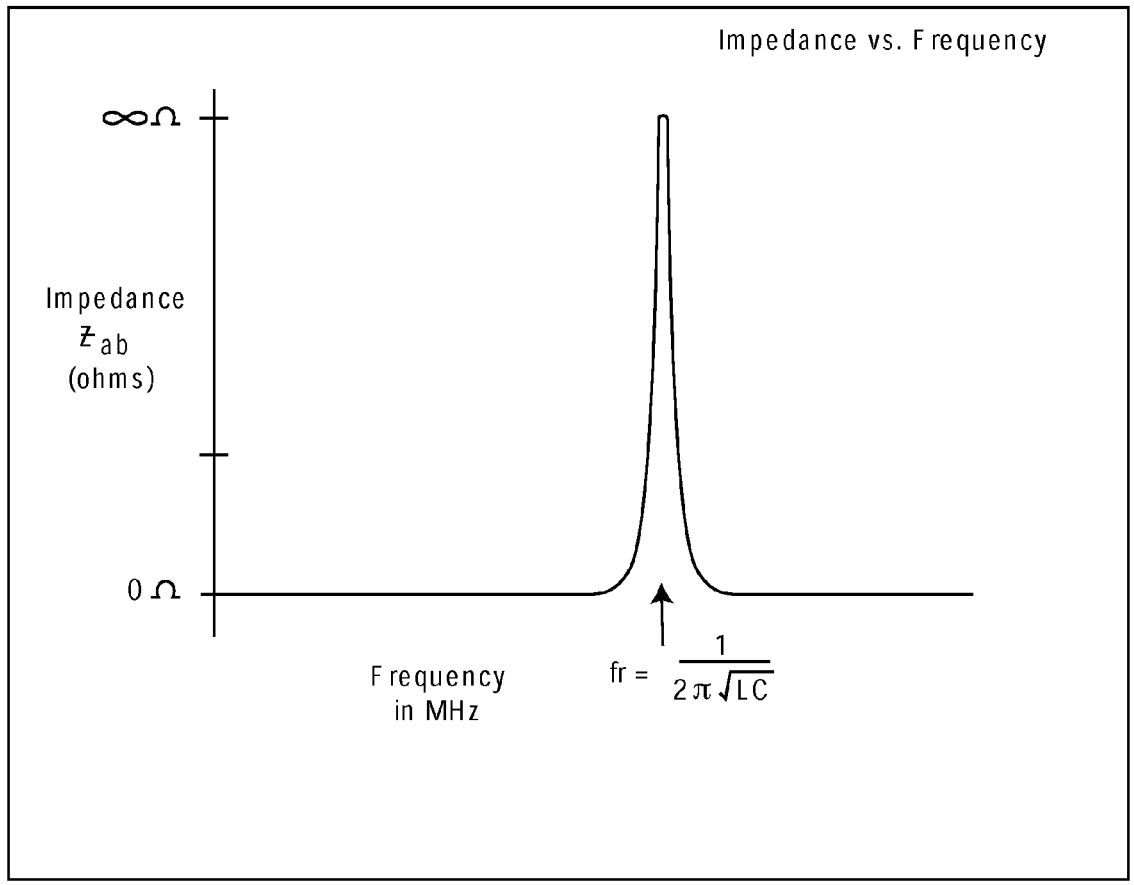
FIG. 18 is a graph showing impedance versus frequency for the bandstop filter circuit of FIG. 16.
FIG. 19 is a chart illustrating an equation for the impedance of an inductor in parallel with a capacitor and reactance equations for the inductor and the capacitor of the bandstop filter circuit of FIG. 16.

FIG. 18 is a graph showing impedance versus frequency for the parallel tank or bandstop filter circuit 170 of FIG. 16. As one can see, using ideal (zero resistance) circuit components, the impedance measured between points A and B for the parallel bandstop filter 168 shown in FIG. 16 is very low (zero) until one approaches the resonant frequency $f_r$. At the frequency of resonance, these ideal components combine together to look like a very high or, ideally, an infinite impedance. The reason for this comes from the denominator of the equation $Z_{ab}$ for the impedance for the inductor 172 in parallel with the capacitor 174 shown as FIG. 19. When the inductive reactance is equal to the capacitive reactance, the two imaginary vectors cancel each other and go to zero. Referring to the equations in FIG. 19, one can see in the impedance equation for $Z_{ab}$, that a zero will appear in the denominator when $X_L = X_C$. This has the effect of making the impedance approach infinity as the denominator approaches zero. As a practical matter, one does not really achieve an infinite impedance. However, tests have shown that several hundred or even thousands of ohms can be realized which offers a great deal of attenuation and protection to RF pulsed currents from MRI. What this means is that at one particular unique frequency, the impedance between points A and B in FIG. 16 will appear very high (analogous to opening a switch). Accordingly, it would be possible, for example, in the case of a cardiac pacemaker to design the cardiac pacemaker for compatibility with one single popular MRI system. For example, in the AMD patient literature and physician manual it could be noted that the pacemaker lead system has been designed to be compatible with 3 Tesla MRI systems. Accordingly, with this particular device, a distal Tip bandstop filter 168 would be incorporated where the L and the C values have been carefully selected to be resonant at a center frequency of 128 MHz, presenting a high impedance at the MRI RF pulse frequency.

Figure 20:
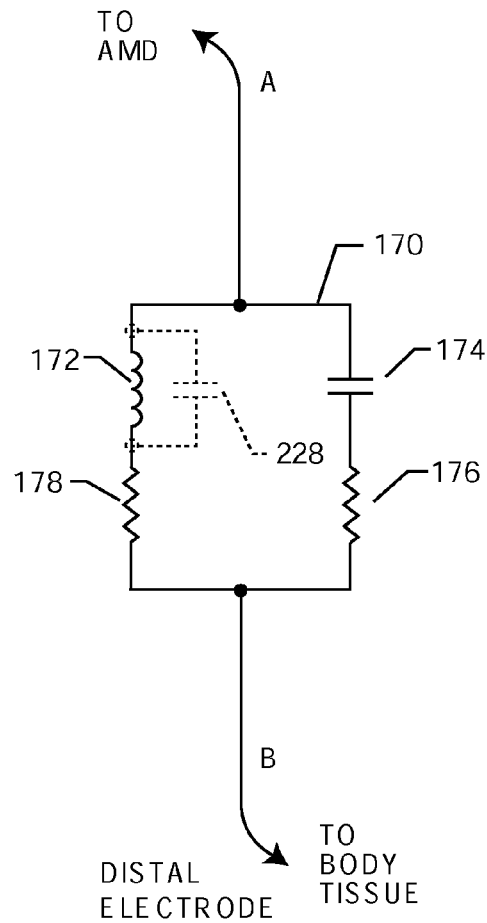
FIG. 20 is a schematic diagram illustrating the bandstop filter circuit of FIG. 16, except in this case the inductor and the capacitor have series resistive elements.

FIG. 20 is a schematic drawing of the parallel bandstop circuit 170 of FIG. 16, except in this case the inductor 172 and the capacitor 174 are not ideal. That is, the capacitor 174 has its own internal resistance $R_C$ 176, which is otherwise known in the industry as equivalent series resistance (ESR). The inductor 172 also has a resistance $R_L$ 178. For those that are experienced in passive components, one would realize that the inductor 172 also has parallel capacitance. This parasitic capacitance 228 comes from the stray capacitance associated with adjacent inductor turns. Accordingly, the circuit shown in FIG. 20 is a very good approximation model for the novel parallel bandstop circuits 170 as described herein. A careful designer can make the parasitic capacitance 228 very significant which would create a resonant bandstop filter in inductor coils. However, as shown in FIG. 20, the parasitic capacitance could be kept quite low so it is insignificant compared to the performance of the overall bandstop circuit illustrated in FIG. 20.

This is best understood by considering the FIG. 20 bandstop filter circuit 170 at the frequency extremes. The inductive reactance equation is $X_L = 2\pi f L$ (reference FIG. 19). When the frequency f is close to zero (DC), this means that the inductor 172 looks like a short circuit. It is generally the case that biologic signals are low frequency, typically between 1 Hz and 2000 Hz. For example, in a cardiac pacemaker 110C, the frequencies of interest appear between 10 Hz and 1000 Hz. At these low frequencies, the inductive reactance $X_L$ will be very close to zero ohms. Over this range, on the other hand, the capacitive reactance $X_C$ which has the equation $X_C = 1/(2\pi f c)$ will look like an infinite or open circuit (reference FIG. 19). As such, at low frequencies, the impedance between points A and B in FIG. 20 will equal to the value of resistor 178 in ohms. Accordingly, the inductor resistance 172 ($R_L$) should be kept small enough to minimize attenuation of biologic signals or attenuation of stimulation pulses to body tissues. This will allow biologic signals to pass through the bandstop filter 168 freely. It also indicates that the amount of capacitive ESR loss 176 is not particularly important. As a matter of fact, it would be desirable if that loss were fairly high so as not to freely pass very high frequency signals (such as undesirable EMI from cellular phones). It is also desirable to have the Q of the circuit shown in FIG. 16 relatively low so that the bandstop filter 3 dB frequency bandwidth can be a little wider. In other words, in a preferred embodiment, it would be possible to have a bandstop filter resonance curve wide enough at the 3 dB and 10 dB down points to attenuate the RF pulsed frequencies over a range of 1.5 Tesla scanners. As previously mentioned, the RF pulsed frequency variation of commercial scanners can be as much as 0.5 MHz to 1 MHz (this variation is MR machine to MR machine and also from manufacturer to manufacturer).

Figure 21:
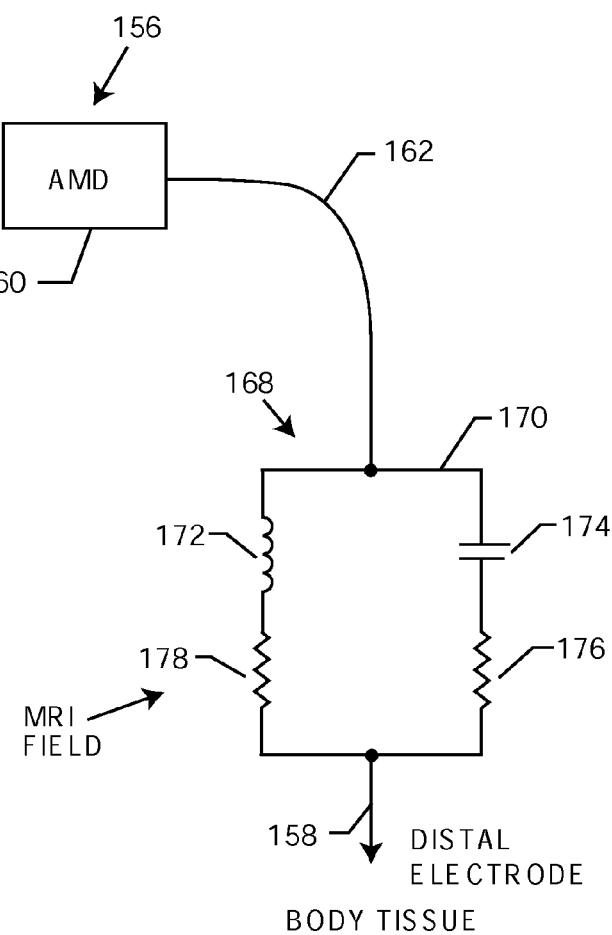
FIG. 21 is a diagram similar to FIG. 13, illustrating the bandstop filter of FIG. 20 added near the distal electrode.

FIG. 21 is a drawing of the unipolar AMD lead system, shown in FIG. 13, with the bandstop filter 168 in series with the lead conductor disposed at or near the distal electrode 158. As previously described, the presence of the bandstop circuit 170 will present a very high impedance at a selected resonant center frequency as well as across a selected range of MRI RF pulse frequencies about the center frequency. This will prevent currents from circulating through the distal electrode 158 into body tissue at this selected frequency(s). This will provide a very high degree of important protection to the patient so that overheating does not cause tissue damage.

Figure 22:
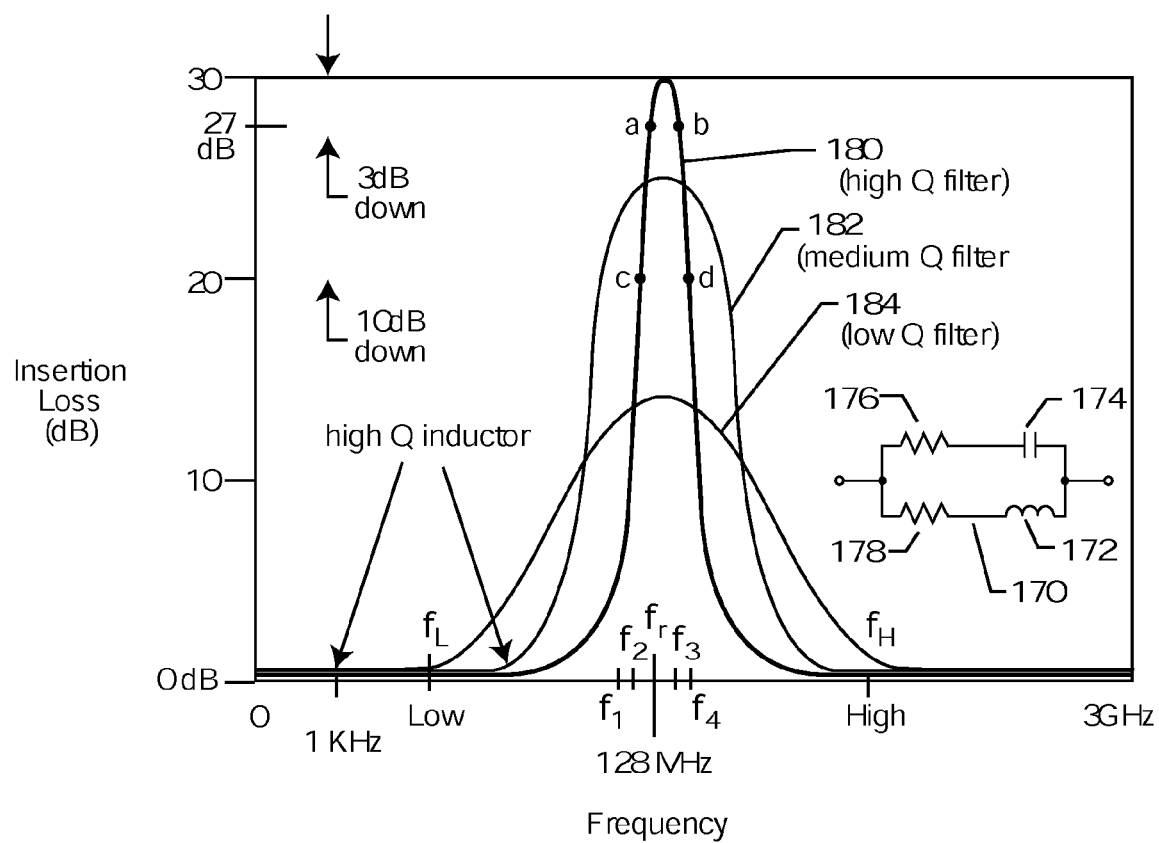
FIG. 22 is a graph of insertion loss versus frequency for bandstop filters having differing quality "Q" factors.

Referring now to FIG. 22, the efficiency of the bandstop filter 168 is also measured in terms of a quality factor, Q. The bandstop filter circuit Q is typically expressed using the following equation:

$$Q = \frac{f_r}{\Delta f_{3dB}}$$

where $f_r$ is the resonance frequency, and $\Delta f_{3dB}$ shown as points a and b in FIG. 22 is the 3 dB bandwidth of the bandstop filter. The 3 dB bandwidth is determined from an insertion loss sweep in a balanced 50-ohm system. It is recognized that an implanted lead source impedance and an AMD input (load) impedance are variable with frequency, lead trajectory and other factors. In other words, it is highly unlikely that an implanted lead source and device load impedance will be 50-ohms. However, to simplify matters and for comparison purposes, the insertion loss curves and resulting 3 dB and 10 dB bandwidths will be calculated and/or measured in a balanced 50-ohm in-vitro (bench top) measurement system. The 3 dB bandwidth is defined as the difference in frequency between the insertion loss upper 3 dB down frequency "b" and the lower 3 dB down frequency "a". The upper and lower 3 dB frequencies are generally centered around the resonant frequency of the bandstop filter. These measurements are best conducted using a 50-ohm swept spectrum analyzer or 50-ohm network analyzer of the bandstop filter portion(s) of the implantable lead. Accordingly, the 3 dB bandwidth is $f_3-f_2$ and the 10 dB bandwidth is $f_4-f_1$.

The 10 dB down points are shown as points "c" and "d" in FIG. 22 and correspond with frequencies $f_1$ and $f_4$. Accordingly, the 10 dB bandwidth is $f_4-f_1$ measured either in kHz or MHz. In general, the insertion loss curve can also be equated to an attenuation curve wherein the source and load impedances would be 50 ohms. In practice, the source impedance would be the source impedance of the lead and body tissue and the load impedance would be the input impedance of the AMD itself. Those experienced in the art will realize that the balanced 50-ohm approach defines a repeatable and design comparison test method. For the medium Q filter 182 and the low Q filter 184, there are also corresponding 3 dB down points and 10 dB down points (not shown for clarity).

Referring once again to FIG. 22, one can see the schematic for the bandstop circuit 170 including resistors 176 and 178. Resistor 176 represents the equivalent series resistance of the capacitor 174, or a discrete series resistor added in series with the capacitor. Resistor 178 represents the equivalent series resistance of the inductor 172, which is commonly due to the resistance of the coiled wire turns or wire circuit traces of the inductor. Resistor 178 could also include a separate discrete chip resistor or other type of resistor added in series with the inductor portion of the bandstop circuit 170. Controlling the values of these resistances controls the 3 dB and 10 dB bandwidths and hence the quality factor Q of the bandstop filter.

Both the 3 dB bandwidth and the 10 dB bandwidth can be varied in accordance with the application. For example, if the application is for a very specific situation, such as a dedicated MRI guided catheter lab, then only one MRI scanner is involved. For example, if it is known that only a Siemens 1.5 Tesla MRI scanner of a particular model and known magnet is to be used, then we can be confident of a very specific MRI RF pulsed frequency. The bandstop filter 168 could be designed with relatively narrow 3 dB and 10 dB bandwidths. In this case, the 10 dB bandwidth could be as narrow as 10 kHz. In this regard it should be borne in mind that the gradient field of the MRI scanner grades the main static field. A way to visualize this is with a patient lying in the supine position on the MRI scanner table. As the gradient field varies, the static magnetic field strength varies from head-to-toe of the patient. This means that the resonant frequency of the protons vary accordingly. In this way, the RF frequency varies thereby obtaining the image slice from the patient. About the narrowest variation is on the order of 10 kHz. On the other hand, if one were to design a bandstop filter 168 for implanted lead applications where multiple MRI scanners (from different manufacturers) needed to be compatible, then a 10 dB bandwidth of 100 kHz minimum would be desirable. In general, in a particularly preferred embodiment, the 10 dB bandwidth would be on the order of megahertz, or a minimum of 500 kHz. By having a 10 dB bandwidth on the order of MHz (0.5 MHz) minimum, one can then be sure that the bandstop filter 168 would be effective over the range of commercially available or labeled 1.5 Tesla MRI scanners. Similar principles apply to 3 Tesla, 5 Tesla and other scanners that have a different static magnetic field strength. In these cases, the RF pulsed frequencies are much higher in frequency and their variation between different manufacturers and also their variation because of the gradient field can be even greater as measured in kHz. In summary, depending upon the application, the 3 dB bandwidth can vary anywhere from 10 kHz to 100 kHz to 0.5 MHz or even to tens of MHz. Similarly, allowing for a "safety margin", the 10 dB bandwidth can vary anywhere from 10 kHz to 200 kHz to 0.5 MHz or even to tens of MHz.

Referring once again to FIG. 22, one can see that at very low frequencies, such as shown by $f_L$, it is important that the bandstop circuit 170 represent a very low impedance. This is because the bandstop filter 168 must pass low frequency pacing and biologic sensing signals with very little attenuation. The same is not true of very high frequencies as shown by $f_H$. In this case it would not matter if the bandstop filter offered additional attenuation since there are no biological signals in this range (just high frequency EMI).

Accordingly, the "Q" or quality factor of the bandstop circuit 170 is very important. In a preferred embodiment, the resistance 178 of the inductor is carefully controlled to control the Q of the overall bandstop filter in accordance with the curves illustrated in FIG. 22.

In the present invention, the overall Q of the bandstop filter 168 is selected to balance impedance at a selected (resonant center) frequency versus frequency bandwidth characteristics. What this means is that the Q of the bandstop filter 168 be sufficiently low so that the 3 dB bandwidth of the bandstop filter 168 is sufficiently wide to attenuate the range of MRI RF pulsed frequencies of interest. On the other hand, the Q of the bandstop filter 168 is balanced or traded off against the impedance of the bandstop filter 168 at resonance. For example, (1) a very high Q 180 bandstop filter 168 will have a very high amount of attenuation (greater than 40 dB) at both its resonance center frequency and also at its 3 dB bandwidth points, however, (2) the 3 dB bandwidth will be so narrow in frequency (less than 10 kHz) that the high Q 180 bandstop filter 168 will not provide adequate attenuation across a broad enough range of MR RF frequencies (such range of frequencies can result due to variations among scanner static magnetic strengths and/or variations in RF frequency due to "grading" by the MRI gradient field(s)). On the other hand, (1) a very low Q 184 bandstop filter 168 will offer only a very small amount of attenuation (less than 10 dB) at both its resonant center frequency and at its 3 dB bandwidth points, but (2) it will have a relatively wide 3 dB bandwidth which is generally greater than several megahertz. For example, for implanted leads that may be exposed to one particular 1.5 Tesla MRI scanner, a bandstop filter 168 is necessary wherein the overall Q of the bandstop filter 168 is selected to balance impedance at a selected frequency versus frequency bandwidth characteristics such that the bandstop filter 168 offers a minimum of 10 dB of attenuation at its resonant center frequency and also that it have a 3 dB bandwidth of at least 10 kHz. For MRI compatibility, other implanted lead applications may require a bandstop filter 168 attenuation of greater than 20 dB at the resonant frequency and a 3 dB bandwidth of greater than 0.5 MHz. The attenuation of the bandstop filter 168 at its resonant center frequency is a function of the bandstop filter 3 dB bandwidth and its L/C ratio. In general, higher inductance gives higher attenuation at resonance. However, for a given lead geometry, there is a practical limit to the amount of inductance available to the designer. In summary, for a particular implantable lead system, the overall Q of the bandstop filter 168 is selected to balance impedance at a selected (resonant) frequency versus frequency bandwidth characteristics.

As mentioned, it is desirable to have a very low loss circuit 170 at low frequencies such that the biological signals not be undesirably attenuated. The quality factor Q not only determines the loss of the filter 168, but also affects its 3 dB and 10 dB bandwidths. If one does a plot of the filter response curve (Bode plot), the 3 dB and 10 dB bandwidths determine the attenuation curve, shape and how sharply the filter response will rise and fall. With reference to the high Q curve 180 of FIG. 22, for a bandstop filter 168 that is resonant at 128 MHz, an ideal response would be one that had infinite attenuation at 64 MHz, but had zero attenuation at low frequencies below 1 kHz. Obviously, this is not possible given the space limitations and the realities of the parasitic losses within components. In other words, it is not possible (other than at cryogenic temperatures) to build an inductor that has zero internal resistance. Accordingly, the practical realization of a circuit to accomplish the stated purposes is a challenging one. This is particularly true when one also considers that the bandstop circuit 170 must also be miniature, highly reliable, and completely biocompatible.

The performance of the circuit is directly related to the efficiency of both the inductance 172 and the capacitance 174; the less efficient each component is, the more heat loss that results, and this can be expressed by the addition of resistor elements, 176 and 178 to the ideal circuit diagram. On the other hand, the effect of lower Q in the bandstop circuit 170 is to broaden the resonance peak about the resonance frequency. By deliberately using a low Q capacitor and/or inductor, one can broaden the resonance such that a moderately high impedance (attenuation) is presented at multiple MRI RF frequencies. As one can see, there are a number of design tradeoffs. Controlling the amount of resistance 178 in the inductor 172 is particularly important for an implantable defibrillator lead. The reason for this is the lead has to conduct a very large pulse current when a patient is defibrillated. This current must flow through the bandstop filter 168 as well as the lead 162. In a particularly preferred embodiment, diodes are used to divert the current around the bandstop filter 168. A more thorough description of transient voltage protected bandstop filters 168 is described in US 2010/0023095 the contents of which are incorporated herein by reference.

Referring again to FIG. 22, one can control both the 3 dB bandwidth and the 10 dB bandwidth by controlling the amount of resistance 176 and 178 in the bandstop filter circuit 168. One must be careful not to let the resistance 178 in series with the inductor 172 be too large or biological frequencies will be attenuated. The reason for this is that at very low frequencies (below 1 kHz), the inductive reactance tends to be very low (approximate zero). At the same time, at very low frequencies the capacitive reactance tends to look infinite. Accordingly, for proper operation of delivering pacing pulses or sensing biological activity, the resistor value 176 really does not matter much. Accordingly, a good way to control the Q of the bandstop filter 168 is to establish resistance 178 that is consistent with the parasitic resistances of inductor 172 windings or turns and also carefully controls the capacitor ESR. However, one must also control the resistive loss 178 of the inductor 172 because if the inductor's resistance 178 gets too high, excessive heating of the bandstop filter 168 could occur. This is because there is a high frequency current that oscillates at the MRI pulsed frequency between the capacitor's 174 electric field and the inductor's 172 magnetic field. This circulating current can create heating about the bandstop filter 168 in one of two ways: 1) by $I^2R$ heating in either resistance 176 or 178 (or both), or, 2) by eddy current losses in the hermetic or shield housing that surrounds the bandstop filter 168. Accordingly, a careful balance between component design and bandstop filter Q must be achieved.

The Lamour equation tells us that the frequency of the pulsed RF field is equal to the MRI constant times the static magnetic field strength of the clinical scanner in Teslas. In any particular MRI scanner, the RF-pulsed frequency does vary as the gradient field grades the static magnetic field. In addition, not all marketing-labeled 1.5-Tesla scanners are the same. There is considerable variation in the static magnetic field strength from different manufacturers. This results in several hundreds of kilohertz or even a half megahertz of difference between the RF pulsed frequency between the various scanner manufacturers. For MRI scanners with stronger magnets, such as 3 Tesla, the RF frequency is higher and the variation of RF frequency between various manufacturers is greater. In this case, the 10 dB bandwidth of the bandstop filter would have to be on the order of tens of MHz (as much as 10 MHz). Accordingly, the bandstop filter 168 is designed to be resonant at a center frequency, $f_r$, representing the center of a range of RF pulsed frequencies. As shown in FIG. 22, a resistance element 176, 178 or both, is added or controlled in order to increase the 3 dB and 10 dB bandwidth of the bandstop filter 168. One can see the attenuation curve for a high Q filter 180, a medium Q filter 182, and a low Q filter 184. The medium Q filter 182 would work for many applications, but the attenuation of the low Q filter 184 generally would not be adequate to be sure that excessive heating at a distal electrode 158 would not occur. In the present invention, the desired curve shapes are 180 or 182. To put this in perspective, for an ideal bandstop filter 168 (meaning that resistances 176 and 178 are both zero), the filter response curve would look like a straight up and down line (not shown) centered above $f_r$. This would, of course, be so narrow that it would be both impractical (other than at cryogenic temperatures) to build and useless over a range of MRI scanners and RF pulsed frequencies. This resistance element can be a discrete resistor or it can be formed from the leads or circuit traces as a parasitic element that forms the inductance 172 itself. For simplicity, this resistance element is not shown in some drawings. However, it will be understood that the bandstop filter 168 is designed to attenuate over a range of MRI RF pulsed frequencies on the order of tens of kilohertz, hundreds of kilohertz, or even tens of megahertz.

Figure 23:
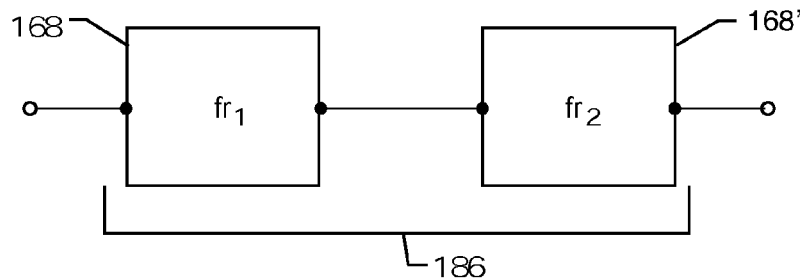
FIG. 23 is an alternate schematic diagram of the bandstop filter of FIGS. 16 and 20, illustrating that the bandstop filter may have multiple resonances at $f_{r1}$ and $f_{r2}$.

FIG. 23 is an alternate schematic diagram of the bandstop filters of FIGS. 16, 20 and 21 showing that two or more bandstop filters 168, 168' can be placed in series in an implanted lead conductor. This means that the resulting composite bandstop filter 186 may have multiple resonances at $fr_1$ and $fr_2$ or any number of additional resonances fn. For example, the inductive coil—parasitic capacitance bandstop filter 186 can be designed to be resonant at both 64 MHz (1.5-Tesla MRI) and 128 MHz (3-Tesla MRI). Accordingly, this would provide a very high impedance in the implanted lead during patient exposure to either one of these commonly available MRI scanners.

Figure 24:
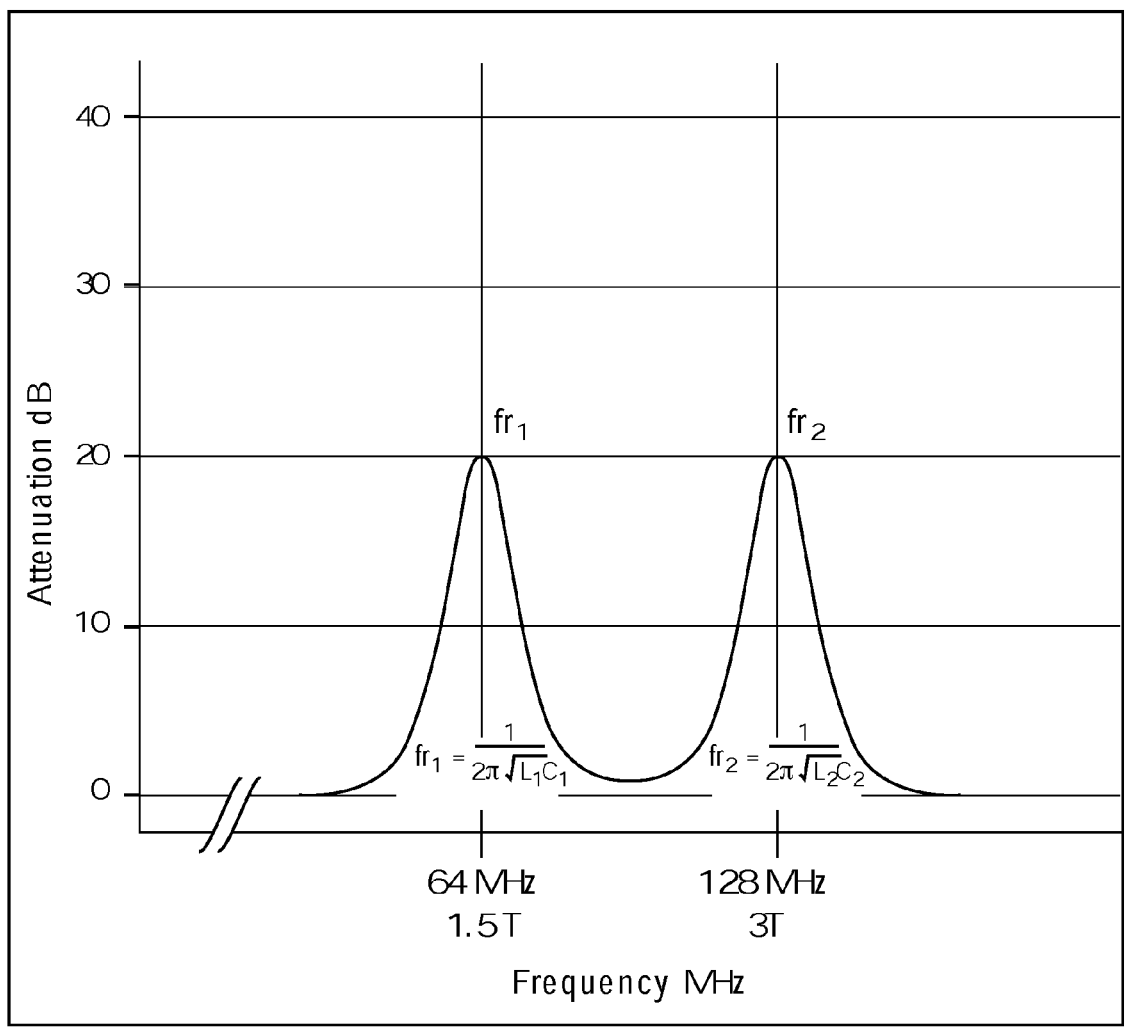
FIG. 24 is a graph of attenuation of the series lowpass and bandstop broadband filter of FIG. 23 versus frequency.

FIG. 24 is a graph of attenuation of the inductive coil—parasitic capacitance bandstop filter 186 of FIG. 23 versus frequency in MHz. As one can see, there is a resonant peak at both $fr_1$ and $fr_2$ corresponding to 64 MHz and 128 MHz. In both cases, the impedance of the inductive coil—parasitic capacitance bandstop filter 186 is quite high which results in an attenuation value exceeding 10 dB. Through careful design, any number of resonant frequency peaks can be created.

Figure 25:
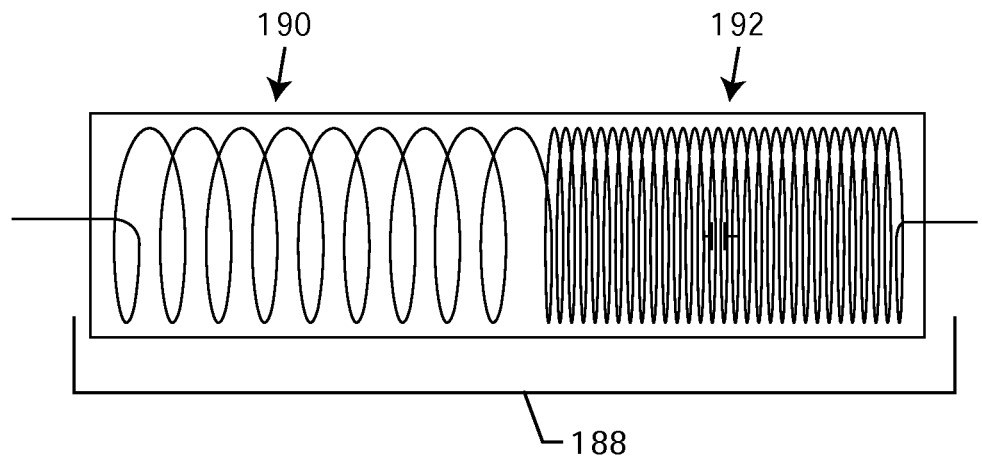
FIG. 25 illustrates a medical lead having an inductor portion in series with a bandstop filter portion all in accordance with the present invention.

FIG. 25 illustrates a composite RF current attenuator 188 of the present invention. FIG. 25 illustrates a lowpass filter inductor portion 190 in series with a bandstop filter portion 192. The bandstop filter 192 is created by parasitic capacitance between the adjacent inductor coil turns. In general, the coils of wire in the bandstop filter portion 192 would have a dielectric coating to increase the parasitic capacitance which would be tightly spaced. On the other hand, the coils of wire in the inductor portion 190 would be spaced more widely apart and preferably not have a dielectric coating such that parasitic capacitance is eliminated or minimized. This results in a composite RF current attenuator 188 consisting of the inductor portion 190 in series with a resonant bandstop filter portion 192. In addition to further spacing or a change in dielectric coating, one could adjust the shape of the wire to minimize surface and therefore stray capacitance. Further one could adjust (i) the number of layers or (ii) the positioning of the layers with respect to previous and additional layers to control the spacing between adjacent wires to minimize stray capacitance.

Figure 26:
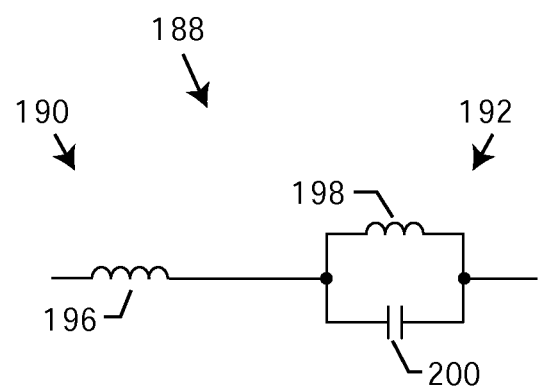
FIG. 26 is an electrical schematic diagram for the structure shown in FIG. 25.

FIG. 26 illustrates the schematic diagram of the composite RF current attenuator 188 illustrated in FIG. 25. The composite RF current attenuator 188 preferably comprises a lowpass filter 190 and a bandstop filter 192 arranged in series. In this embodiment, the lowpass filter 190 comprises an inductor 196. The bandstop filter 192 has an inductor 198 and a capacitor 200 arranged in parallel.

Figure 27:
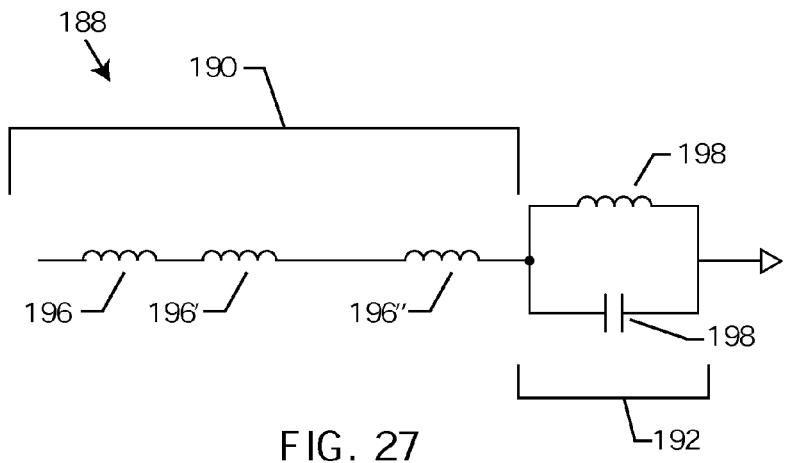
FIG. 27 is an electrical schematic diagram similar to FIG. 26 illustrating that the AMD lead conductor portion may include a number of discrete inductors in series.

FIG. 27 schematically illustrates that the inductance 196 as illustrated in FIG. 25, can be either a single inductor 196 or a series of inductors 196', 196", etc. as shown in FIG. 27. There can be one, two or even "n" inductors 196 along the length of the implanted lead conductor in series with the bandstop filter 192.

Figure 28:
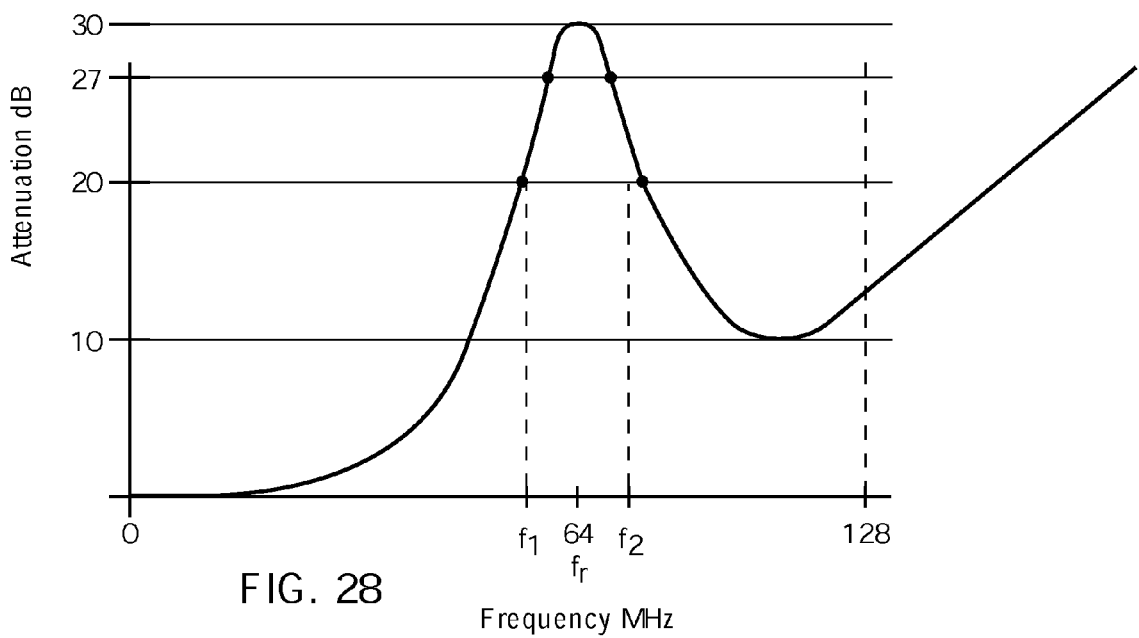
FIG. 28 is an attenuation versus frequency curve for the composite RF current attenuator of FIG. 26 or 27.

FIG. 28 is an attenuation versus frequency curve for the composite RF current attenuator 188 illustrated in FIGS. 25 and 27. As one can see, for illustrative purposes, there is a resonant peak $f_r$ at 64 MHz corresponding to the resonance of the bandstop filter portion 192. Importantly, above this resonant peak $f_r$, the attenuation continues to climb up above 10 dB as the inductive reactance portion 190 of the composite RF current attenuator 188 inductance increases in reactance. The result is a composite RF current attenuator 188 that offers a high degree of attenuation for popular 1.5 Tesla scanners and also offers significant attenuation at 128 MHz and above, which corresponds to 3 Tesla scanners and higher. Another advantage is that the attenuation, due to the inductor portion 190 continues to increase with frequency. Accordingly, for 5 Tesla, 7 Tesla and higher static magnetic field strength scanners, the attenuation will continue to increase. Accordingly, the composite RF current attenuator 188 of FIG. 25 and FIG. 27 provides significant attenuation over a broad range of commonly used MR scanners.

Figure 29:
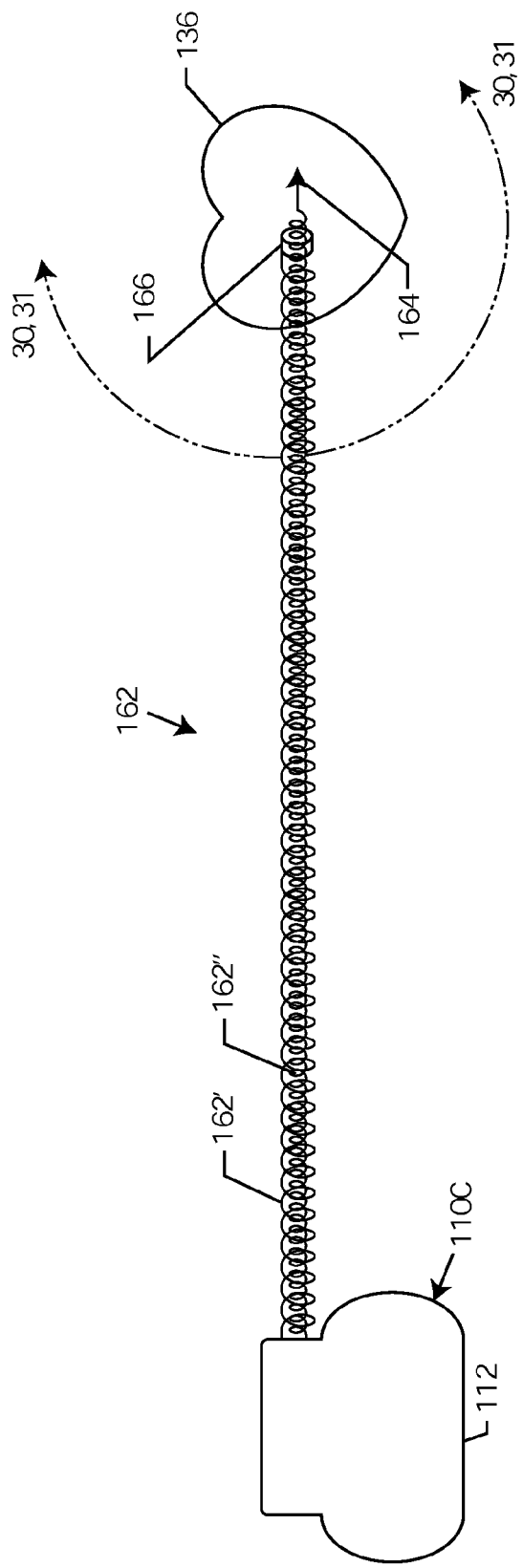
FIG. 29 illustrates a bipolar cardiac pacemaker lead wire showing the distal Tip and the Ring electrodes.

FIG. 29 illustrates a single chamber bipolar cardiac pacemaker 110C and lead 162 showing the distal Tip 164 and the distal Ring 166 electrodes. The lead has two conductors 162' and 162". This is a spiral wound system where the Ring coil 162' is wrapped around the Tip coil 162". There are other types of pacemaker lead systems in which these two lead conductors lay parallel to one another (known as a bifilar lead system).

Here one can see that both the Tip electrode conductor 162" and the Ring electrode conductor 162' are coiled. Because of this they will have some amount of inductance. The inventors have made measurements on pacemaker leads and measured them end-to-end and also made electrical measurements by cutting the leads into sections. What was found was that there is about 5 nanohenries per centimeter to 20 nanohenries per centimeter of parasitic inductance along a typical prior art lead. However, these inductance numbers for prior art leads are not reliable. This is because prior art lead conductors are generally not insulated. In other words, the reason for the coiling is to provide mechanical flexibility and reliability as the leads oscillate mechanically with every beat of the heart. Because these lead conductors are generally not insulated there are many turn-to-turn shorts particularly when going around torturous paths like bends in the Venous system. At biological frequencies (below 2 kHz) these turn-to-turn shorts have no effect on the performance of the lead conductors. This is because inductive reactance is a high frequency phenomenon. Accordingly, in prior art leads it is not possible to rely on their inherent inductance for use in the composite RF current attenuator 188 of the present invention. Referring to FIG. 25, one can see that the inductor 190 is formed by mechanically static coil turns in the implanted lead conductor. These adjacent lead coils are insulated from each other such that they will provide a stable value of inductance for use in lowpass filtering. In a particularly preferred embodiment of the present invention, the lowpass filter portion 190 of the composite RF current attenuator 188 is a section of lead conductor wherein the adjacent inductor coils are insulated from each other and are also held in a mechanically stable state. There are two ways to accomplish this: one could space the coils apart from each other and hold them mechanically stable so that they cannot short out to each other; or insulate all of the adjacent coils wherein the adjacent coils are also adhesively attached to each other, wound on a common mandrel or otherwise held in a mechanically stable condition. In one particularly preferred embodiment for an implantable medical lead, the minimum inductance value of the inductor 190 in series with the bandstop filter 192 is 16 nanohenries. In a second preferred embodiment, the minimum value of inductance is 100 nanohenries. In a third embodiment, the minimum inductance is 300 nanohenries.

Figure 30:
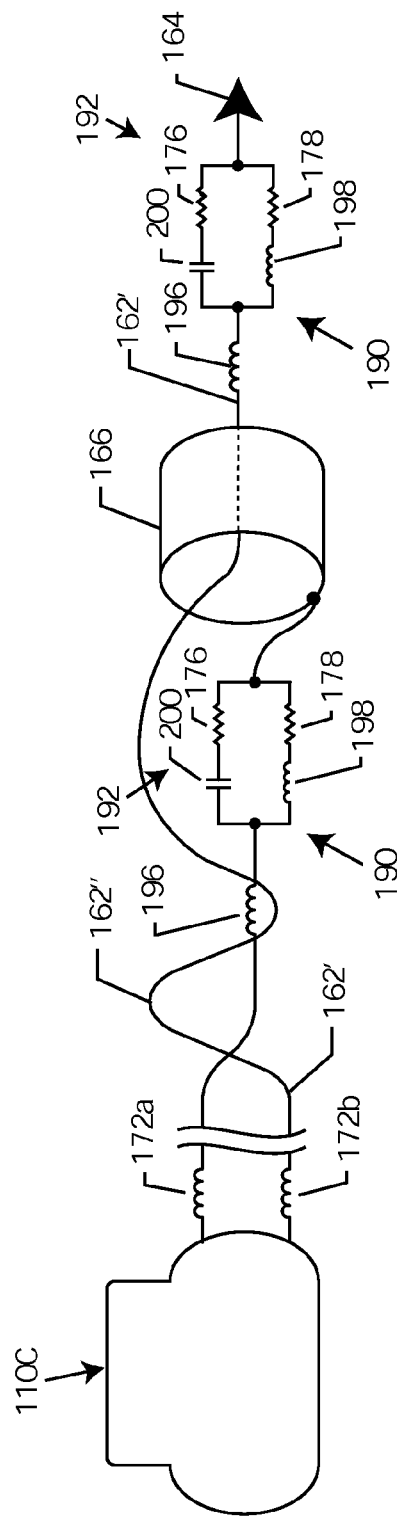
FIG. 30 is an enlarged, fragmented schematic illustration of the area illustrated by the line 30-30 in FIG. 29.

FIG. 30 is a schematic illustration of the area 30-30 in FIG. 29. In the area of the distal Tip 164 and Ring 166 electrodes, broadband lowpass filter inductors 190 have been placed in series with bandstop filters 192 in turn, in series with each of the respective Tip 164 and Ring 166 electrode circuits in each of the lead conductors 162' and 162". Accordingly, at MRI RF-pulsed frequencies, a high impedance will be presented thereby attenuating the flow of undesirable RF current.

Figure 31:
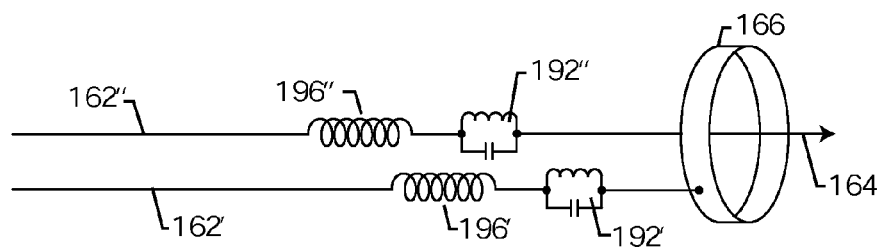
FIG. 31 is similar to FIG. 30 and illustrates inductors located in close proximity to the bandstop filters and the distal electrodes in accordance with the present invention.

FIG. 31 is generally taken from section 31-31 from FIG. 29 and illustrates inductors 196' and 196" placed in series with bandstop filters 192' and 192". For the purposes of simplification, the bandstop filters are shown without their resistive elements 176 and 178, although one skilled in the art will realize that those resistance elements are critical to control the Q of the bandstop filters 192' and 192" as previously described. The inductors 196' and 196" can be formed from coil-wired turns or from chip inductors, solenoid inductors, toroidal inductors or the like.

Figure 32:
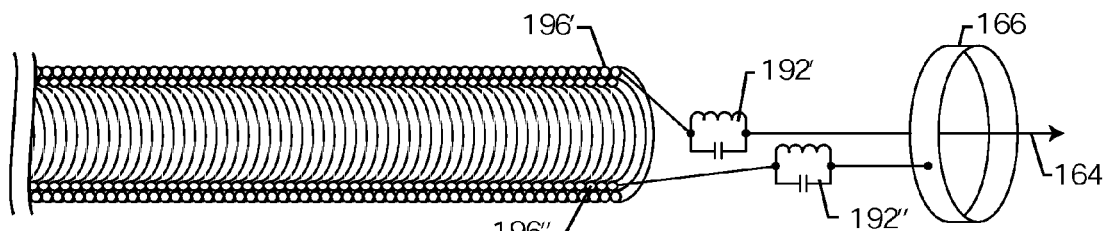
FIG. 32 shows that the inductances of FIG. 31 may be formed from coaxial windings of the lead conductors.

FIG. 32 illustrates that the inductors 196' and 196" of FIG. 31 can be formed by coaxial windings along the length of the lead conductor(s). In this case, this is a bipolar cardiac pacemaker lead where the outer winding 196' connects to the tip electrode 164 and the inner winding 196" relates to the ring electrode 166. The inductance of the windings is controlled by the wire diameter, wire spacing, wire pitch, and number of turns. Therefore an inductor $L_1$ and $L_2$ is formed in series with each of the bandstop filters as shown.

Figure 33:
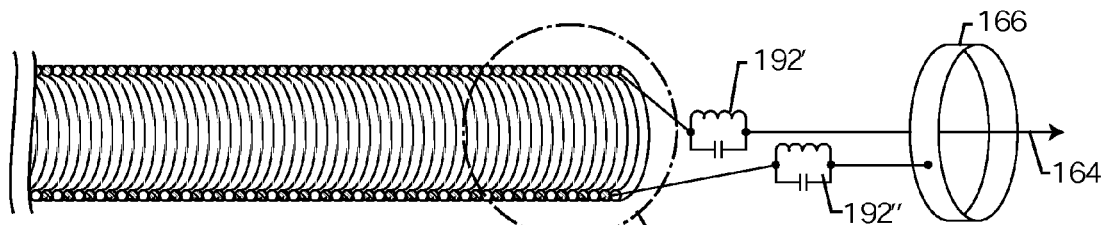
FIG. 33 is similar to FIG. 32 and shows that the lead conductors may be co-radial.

FIG. 33 is very similar to FIG. 32 and illustrates that the coaxial turns may be co-radial. Again, inductors $L_1$ and $L_2$ are formed by each of the co-radial windings. One can see in the exploded section that each of the conductors has an insulation 202. In general, prior art lead conductors do not have such insulation. The reason for this is that prior art biomedical leads are for detection of biologic signals (sensing) and/or providing therapy of biological frequencies. Accordingly, one would like to have the impedance of the lead as low as possible. In other words, it does not matter for prior art biomedical lead applications that adjacent lead coils would be uninsulated and therefore short out to each other. In fact, it is very common for sections of an implanted lead coil to be shorted out particularly when the transvenous lead is inserted around torturous bends. However, it is the feature of the present invention, in order to provide high frequency inductive stability, that these adjacent coils 196' and 196" either be insulated 202 as shown in FIG. 33 such that they cannot short out to one another, or spaced apart as shown in section 190 of FIG. 25 such that they are mechanically separated and can't touch each other. Referring once again to FIGS. 31, 32 and 33, in order to provide a stable value of inductance 192' and 192", the adjacent coils should not only be insulated, but they should be held mechanically in fixed or stable relationship to one another. This can be accomplished by dipping the leads in an insulation material that also adds an adhesive thereby bonding the adjoining coil sections together. Undesirably, bonding of the lead coils together adds mechanical rigidity to the lead. Mechanical rigidity is undesirable for two reasons. The first one is that it makes the lead more difficult to insert either through tunneling or through transvenous insertion through torturous paths. Another reason is that oftentimes leads are subjected to millions of oscillations, such as in a cardiac application. The prior art lead coils were used to provide mechanical flexibility and reliability against such consistent cardiac movement. Therefore, in the present invention the inductor or lowpass filter portion 190 of the composite RF current attenuator 188 where the lead body coils are held in a mechanical stable or rigid relationship is kept relatively short. In a particularly preferred embodiment, each inductive section would be no longer than two centimeters. Similar design constraints apply to certain neurostimulators. For example, for a spinal cord stimulator, a nerve paddle is placed up against the spinal nerve root. As the patient goes through his or her daily life and the spine flexes, it is important that the implanted lead conductors also be able to flex. However, this is not nearly as challenging an application for the cardiac application. In general for spinal stimulators, a rigid inductive portion 190 of the lead should exceed no more than about five centimeters.

Figure 34:
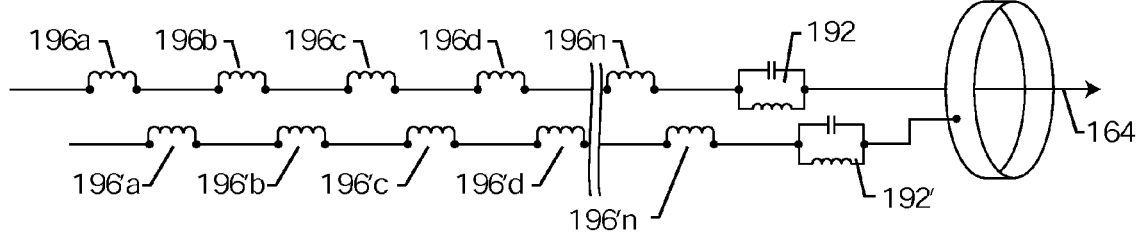
FIG. 34 illustrates that the inductors can be distributed along the entire length of the lead conductors.

FIG. 34 illustrates that these inductances 196 and 196' may be distributed along the entire length of the implanted lead conductor summing up to form a total inductance in series 190, 196 with each of the bandstop filters 192 and 192'.

Figure 35:
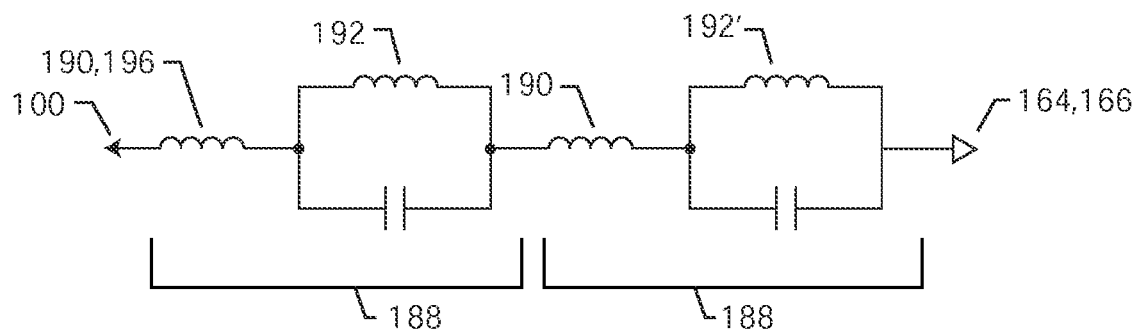
FIG. 35 illustrates that any number of inductor lowpass filters and bandstop filters can be placed in series along the length of an implanted lead conductor.

FIG. 35 is a schematic diagram illustrating that the composite RF current attenuator 188 illustrated in FIG. 31 can consist of multiple inductor 190 and bandstop filter 192 segments placed in series. In other words, there can be one, two or even n number of EMI composite RF current attenuators 188 placed along the length of an implanted lead conductor 162.

Figure 36:
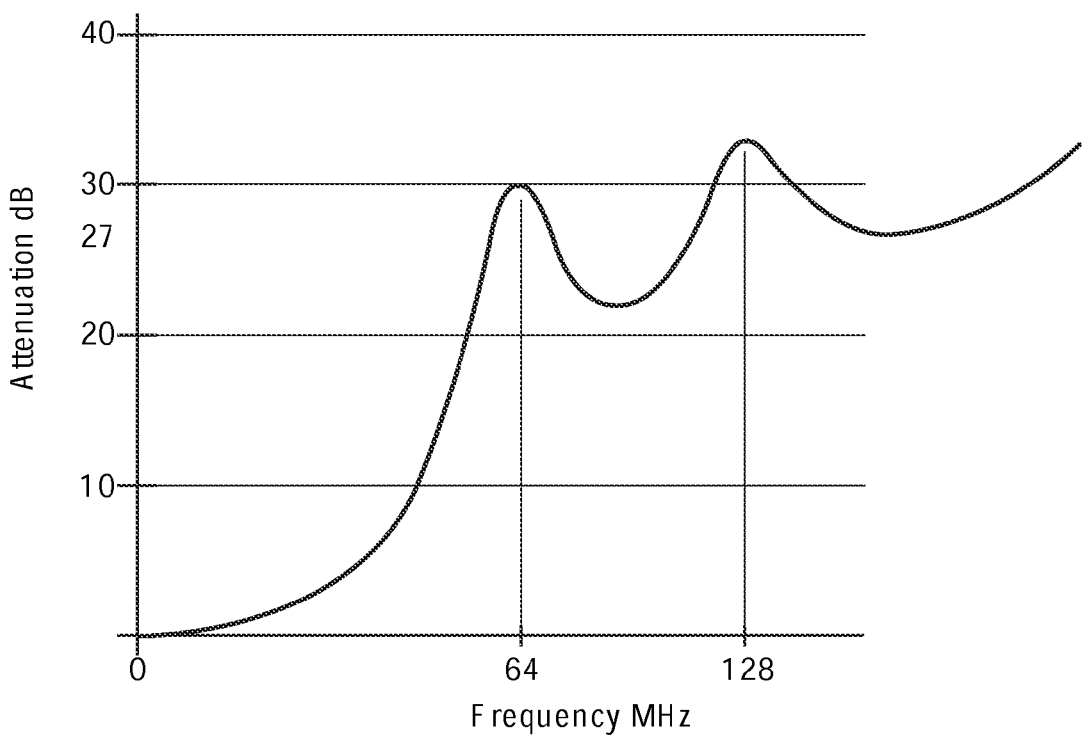
FIG. 36 is an attenuation versus frequency curve for the composite RF current attenuator shown in FIG. 35.

FIG. 36 is an attenuation versus frequency curve for the combination of two composite RF current attenuators 188 as shown in schematic diagram FIG. 35. One can see that there are two resonant peaks. In this case, one at 64 MHz and another at 128 MHz, which represent the MRI RF-pulsed frequencies for 1.5 Tesla and 3 Tesla MRI scanners. One can see that between the two resonant peaks of 64 MHz and 128 MHz, there is still substantial attenuation that's provided and this is because of the series inductor elements 190. One will also notice that at frequencies above 128 MHz, the attenuation continues to increase and again, this is due to the presence of the inductor elements 190.

Figure 37:
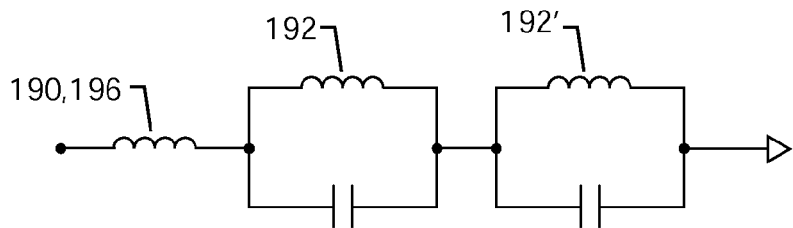
FIG. 37 illustrates that the inductor lowpass filter can be placed in series with one or more bandstop filters.

FIG. 37 illustrates that a single inductive element 190 or a distributive inductive element 196 can be placed in series with two or more BSF elements 192 and 192'.

Figure 38:
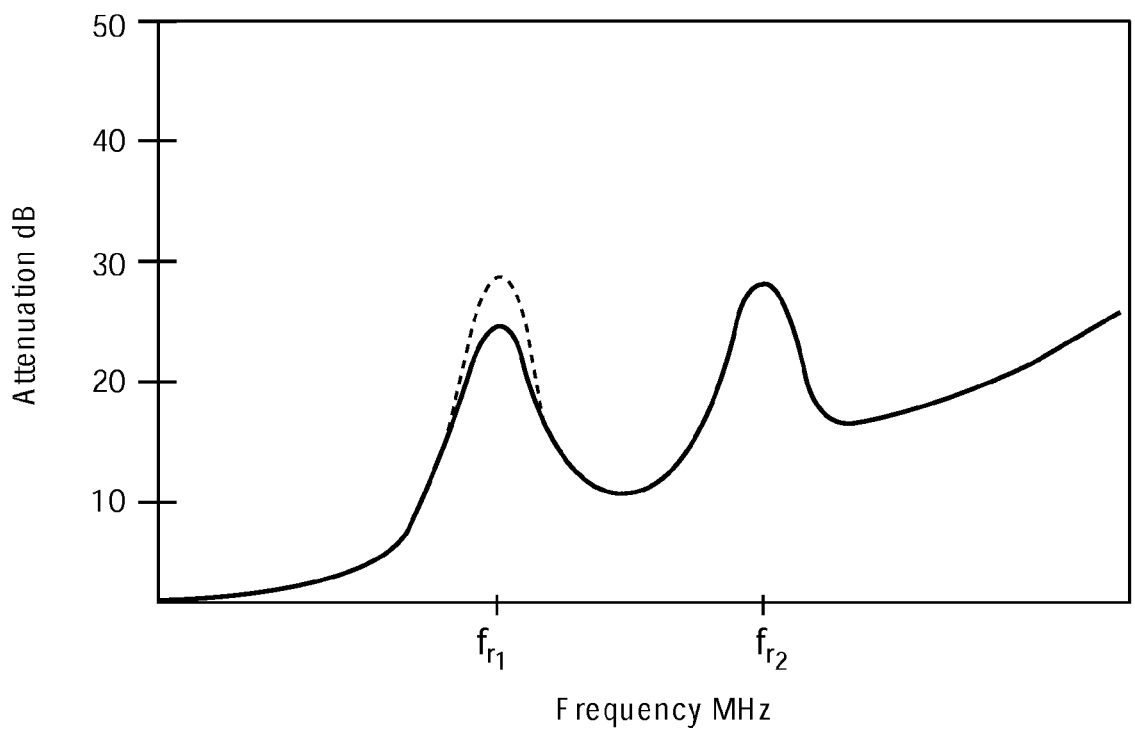
FIG. 38 is an attenuation versus frequency curve of the composite RF current attenuator illustrated in FIG. 37.

FIG. 38 is an attenuation versus frequency curve for the configuration shown in FIG. 37.

Figure 39:
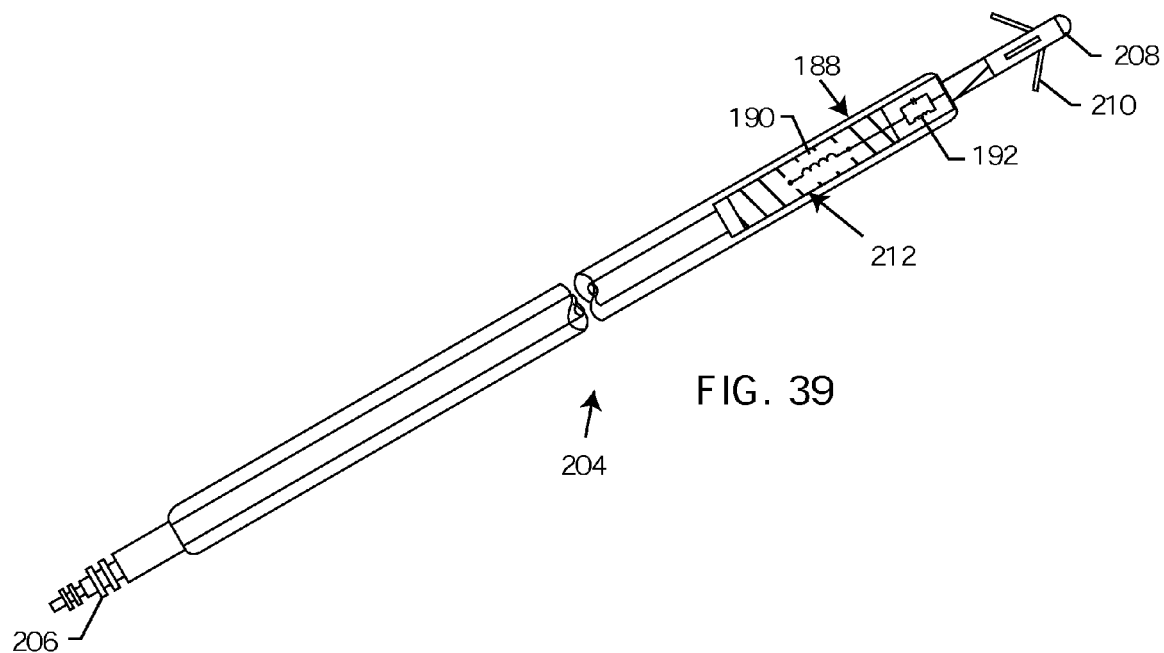
FIG. 39 is an elevational view of a unipolar pacemaker implantable lead having a proximal connector wherein a series broadband lowpass inductor and bandstop filter is installed at, near or within the distal electrode.

FIG. 39 illustrates a unipolar pacemaker lead 204 having a proximal connector 206 such as described by International Standards ISO IS-1, DF-1, DF4 or IS4. This proximal connector 206 would be plugged into a cardiac pacemaker 110C, a cardioverter defibrillator 110I or the like (not shown). The distal end of the lead has a passive tip or distal unipolar electrode 208 with tines 210 which are used to grasp trabecular or other tissue within a human heart. Shown is a composite RF current attenuator 188 of the present invention having an inductor 190 and BSF 192, which is located near, at or adjacent to the distal unipolar electrode 208. As previously described, when exposed to an MRI high intensity RF environment, the composite RF current attenuator 188 impedes the undesirable flow of RF currents into body tissues via electrode 208. The lead body has an overall insulation 212 which extends over the composite RF current attenuator 188 to a point near the distal electrode 208. This insulation 212 prevents RF currents from circulating through body fluids thereby tending to short out or degrade the impedance of the composite RF current attenuator 188. In a preferred embodiment, the overall insulation 212 still provides that the center of the composite RF current attenuator 188 can be hollow for convenient guide wire insertion. In addition, the center of the composite RF current attenuator 188 could incorporate one or more valves such that additional leads or guide wires placed from the proximal side can be routed and sealed.

Figure 40:
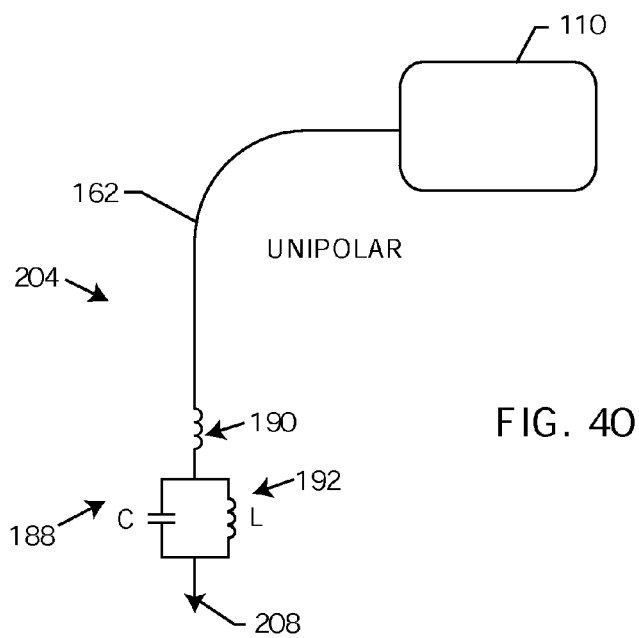
FIG. 40 is an electrical schematic diagram of the unipolar implantable lead of FIG. 39.

FIG. 40 is a schematic diagram of the unipolar lead 204 of FIG. 39 showing the AMD 110 and a composite RF current attenuator 188 of the present invention installed preferably at or near the distal tip electrode 208.

Figure 41:
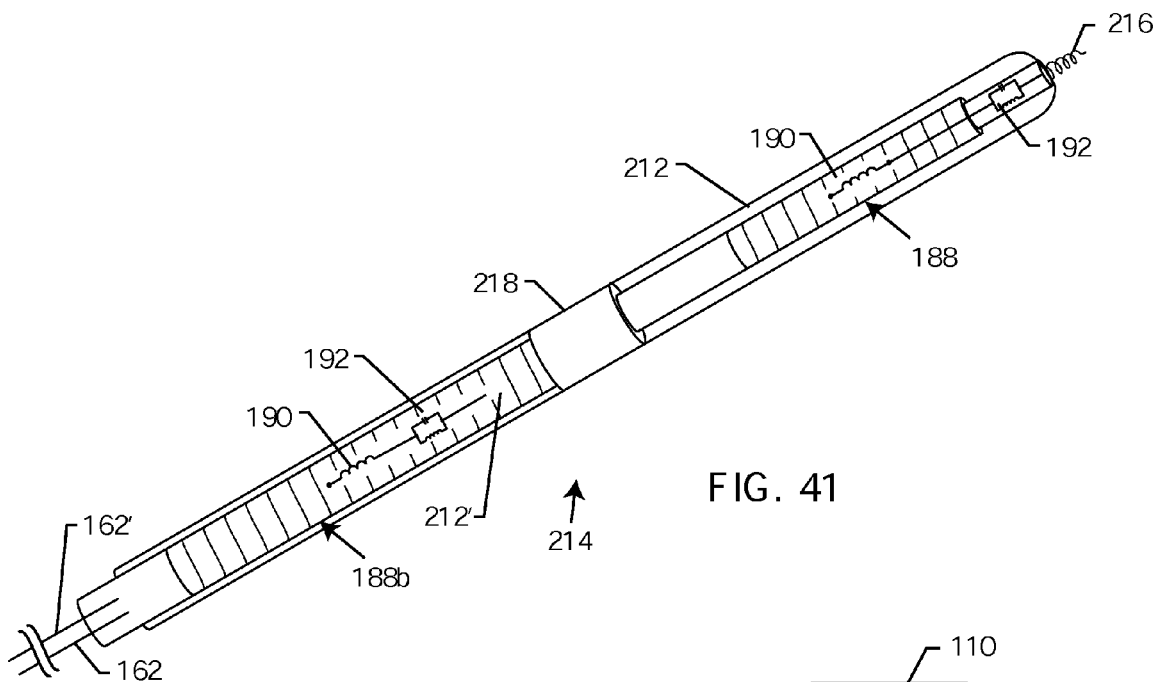
FIG. 41 is a view similar to FIG. 39 except that the composite RF current attenuator is associated with both the Tip and Ring electrodes of a bipolar pacemaker lead.

FIG. 41 is very similar to FIG. 39 except a bipolar active fixation electrode 216 is shown at the distal end or tip of the implanted lead 214. In this case, the active fixation screw-in helix tip electrode 216 has been extended, which would typically be screwed into cardiac tissue. A ring electrode 218 forms a bipolar electrode system wherein pacing and sensing can be conducted between the helix tip electrode 216 and the ring electrode 218. There are two lead conductors 162 and 162' which are plugged into the active medical device 110. There is a composite RF current attenuator 188 in series with the active fixation helix electrode 216 and also a composite RF current attenuator 188' in series with the ring electrode 218. In this way, both the distal helix 216 and ring electrodes 218 would both be prevented from overheating in an MRI environment. Insulation 212 prevents RF currents from flowing through body fluids and shorting out the composite RF current attenuator 188. It is important that the insulation 212 cover both the inductor portion 190 and the bandstop filter portion 192. Stray RF currents flowing through body tissue could seriously degrade the impedance of either of these important elements of the composite RF current attenuator. In addition, the insulating layer 212 also protects the implanted lead, provides flexibility and lubricity (to ease transvenous lead insertion) and aids in the long-term reliability of the overall lead system.

Figure 42:
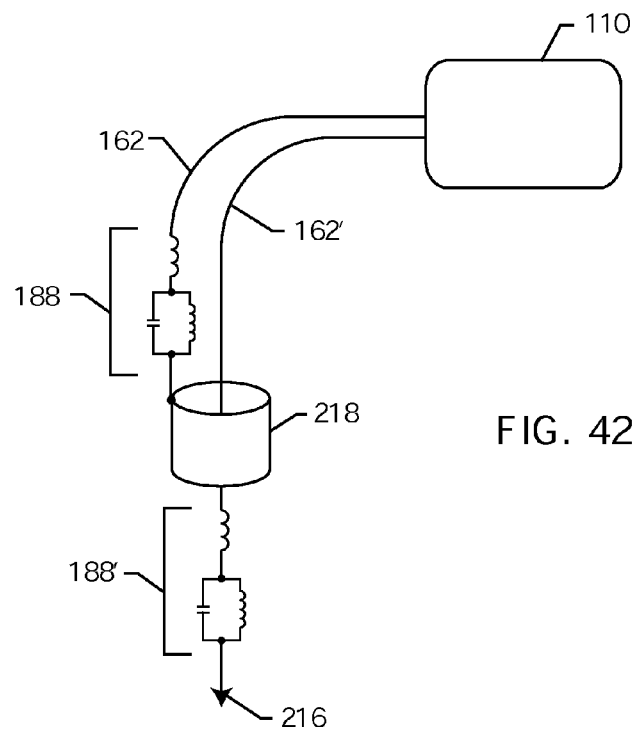
FIG. 42 is an electrical schematic diagram of the bipolar lead illustrated in FIG. 41.

FIG. 42 is the schematic diagram of the bipolar lead 214 illustrated in FIG. 41. One can see the active implantable medical device 110 such as a cardiac pacemaker 110C with implanted lead conductors 162 and 162'. Lead conductor 162 is connected in series with a composite RF current attenuator 188 to ring electrode 218. Lead conductor 162' has a composite RF current attenuator 188' connected in series with active fixation tip electrode 216. As previously described, in preferred embodiments, the series composite RF current attenuators 188 and 188' are very near, at or within the respective distal electrodes. This prevents RF current induction from MRI fields from coupling around the wave filters and inducing currents in the distal electrodes.

Figure 43:
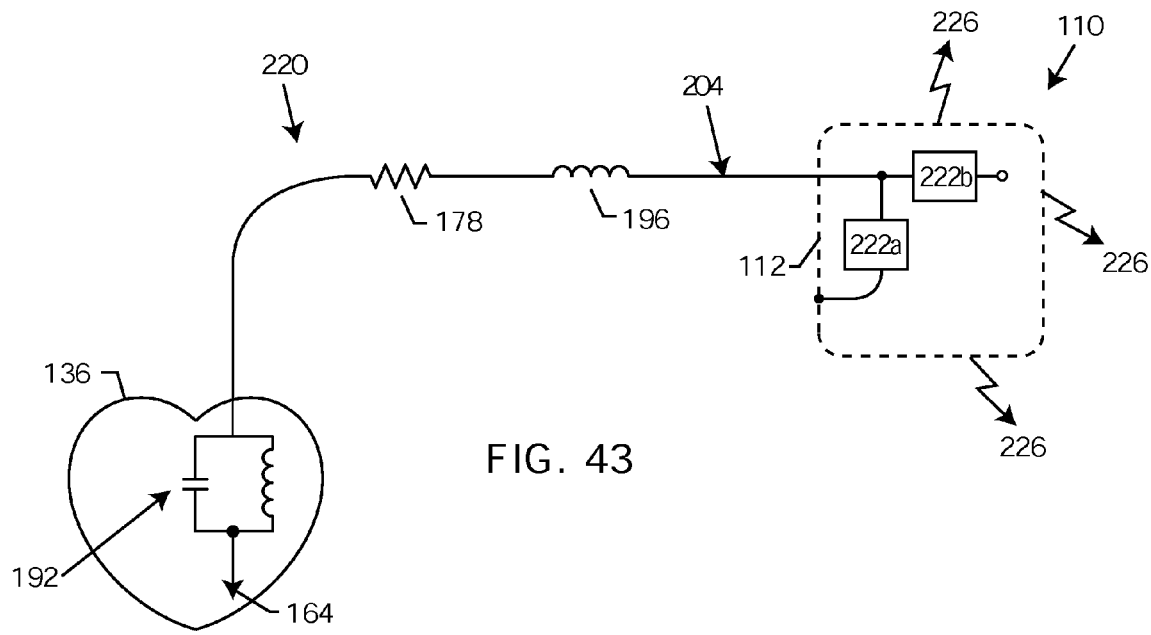
FIG. 43 is an electrical schematic illustration of a unipolar lead system for an AIMD.

FIG. 43 shows a unipolar lead system 220 for an active implantable medical device 110. A unipolar lead system is shown for simplicity. Any number of leads can be routed from an active medical device 110 to distal electrodes 164. The bandstop filter 192 is illustrated in close proximity to distal Tip electrode 164. Inside of the AIMD housing 112 is a diverter element 222a disposed between the conductor circuit trace 204 and the AIMD housing 112. In addition there is an impeder element 222b which is in series with the lead conductor 204 circuit trace. The impeder element 222b as illustrated in FIG. 43 is optional. The operation of impeders and diverters was described in connection with FIGS. 5-12 herein.

Figure 44:
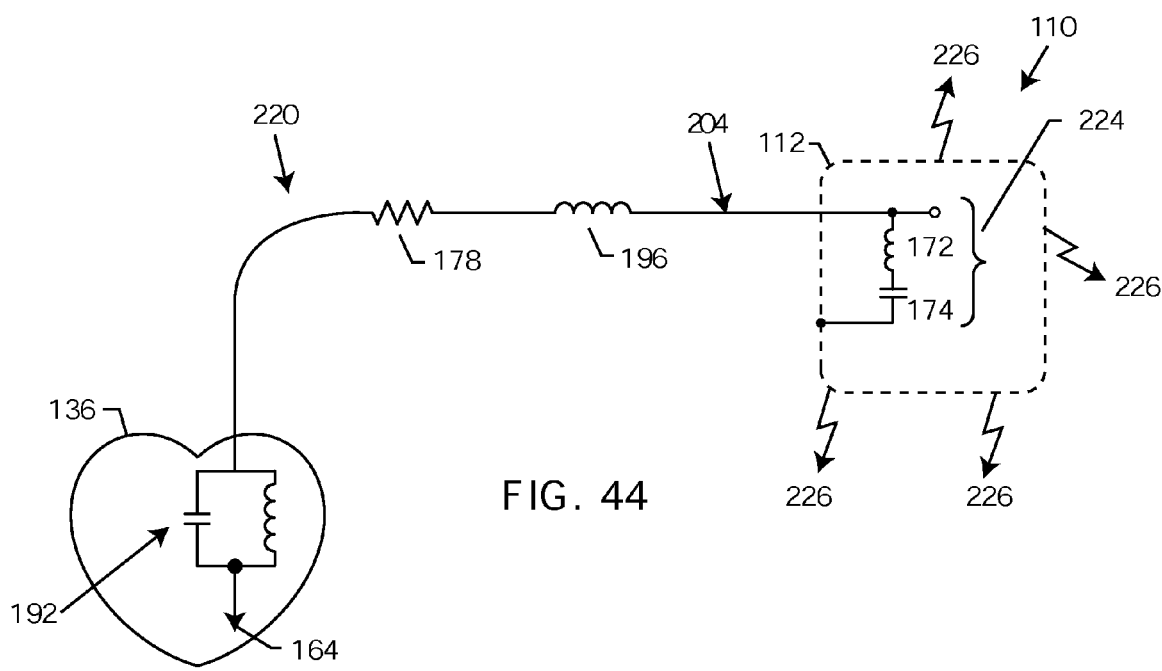
FIG. 44 is a schematic illustration similar to FIG. 43, wherein an L-C trap filter has been placed inside the AIMD housing.

FIG. 44 is similar to FIG. 43 except that the impeder element 222a has been replaced by an inductor 172-capacitor 174 trap filter. This is illustrative of just one type of diverter which can include capacitors or any type of lowpass filter. A more thorough description of FIGS. 43 and 44 can be found in U.S. Patent Publication 2010/0191236 the contents of which are incorporated herein. In FIG. 44, the inductor 172 and the capacitor 174 have been designed to be resonant at the pulsed RF frequency of the MRI equipment. Therefore, this forms an RF short to AIMD housing 112 which becomes an energy dissipating 226 surface. As previously described, an impeder 222b could be added in combination with the inductor 172-capacitor 174 trap filter in order to improve its high frequency attenuation performance. It is desirable that the energy dissipating surface be relatively large in area so that a very small temperature rise occurs on the surface 112 as the MRI RF energy is being dissipated. In one embodiment, as described in U.S. Patent Publication 2010/0191236, the impeder 222b can be any type of lowpass filter, an inductor, or a bandstop filter. In the present invention, the inductive component 196 of the lead cooperates with the bandstop filter 192 to form a composite RF current attenuator 188.

The equivalent inductance 196 and resistance 178 of the lead system also includes the impedance of any tissue return path. It should be noted that the present invention applies to any type of AIMD including those AIMDs whose housing 112 may actually be an active electrode or part of an electrode return path. For example, there are certain neurostimulator applications involving a number of distal electrodes that all have return paths through body tissue from a distal electrode 164 all the way to a common electrode which is also the device housing 112. Referring once again to FIG. 43 one can see that on the interior of the generally metallic housing 112 of the AIMD 110 there are frequency selective components 222a and 222b. These frequency selective elements can consist of various arrangements of capacitors, inductors and resistors or even short circuits.

Figure 45:
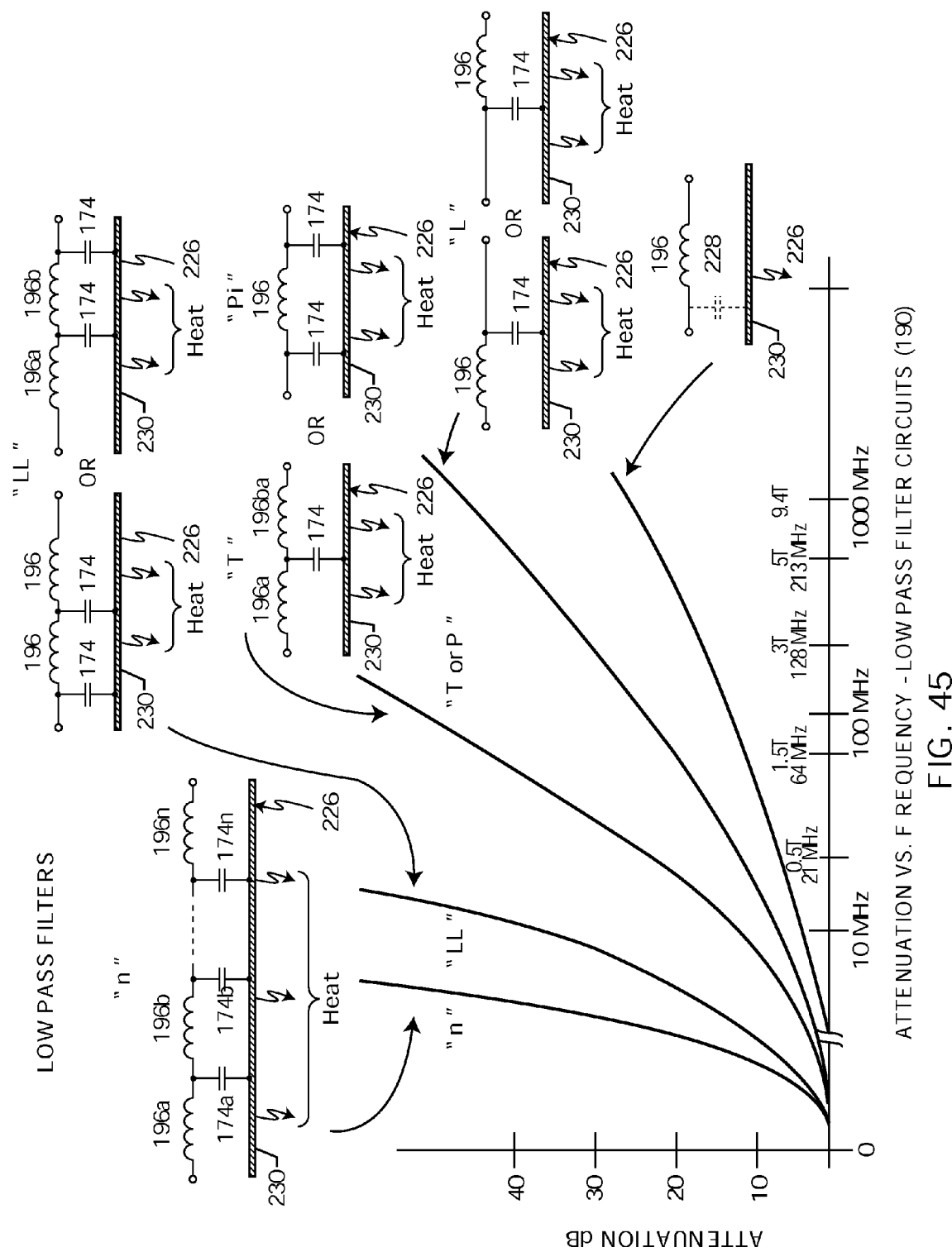
FIG. 45 is an attenuation versus frequency chart for various types of lowpass filters.

FIG. 45 illustrates various types of lowpass filter elements 190, which can be combined with the bandstop filters 192 to form the composite RF current attenuators 188 of the present invention. In the simplest embodiment, an inductor 196 is combined with the bandstop filter 192 to form the composite RF current attenuator 188 of the present invention. However, when combined with energy dissipating surfaces, higher order lowpass filters, including L, Pi, T or even "n" element filters can be used. The heat or energy dissipating surface can be the lead body itself and/or a conductive cylinder, a paddle or other surface area 230 that is in contact with body tissue through which energy may be dissipated. Referring once again to FIG. 45, one can see as one increases the number of filter elements 190, the ability to attenuate or block high frequency signals is improved. When filtering efficiency improves, less MRI RF energy will reach distal electrodes.

In summary, FIG. 45 shows a family of lowpass filters 190. These can include a simple inductor 196 which is known as a single element lowpass filter. Another type of single element lowpass filter is a simple capacitor (not shown). For the simple inductor, a parasitic capacitance 228 is shown. This parasitic capacitance is formed between the lead conductor 204 and the insulation 212 or body of the implanted lead. The energy dissipating surfaces 230 shown in FIG. 45 can be the lead body, the lead body insulation 212 or a separate energy dissipating surface such as a metallic shield which would surround the lead. Energy dissipating surfaces 230 are more thoroughly described in U.S. Pat. No. 7,689,288, the contents of which are incorporated herein by reference. The common terms of art to describe the lowpass filters of FIG. 45 are single element filter (inductor or capacitor), L or reverse L filter, Pi, T, LL or "n" element. In the simplest embodiment of the present invention, the lowpass filter 190 is a single element inductor 196 in series with the lead 204 which may or may not have a parasitic capacitance 228.

Figure 46:
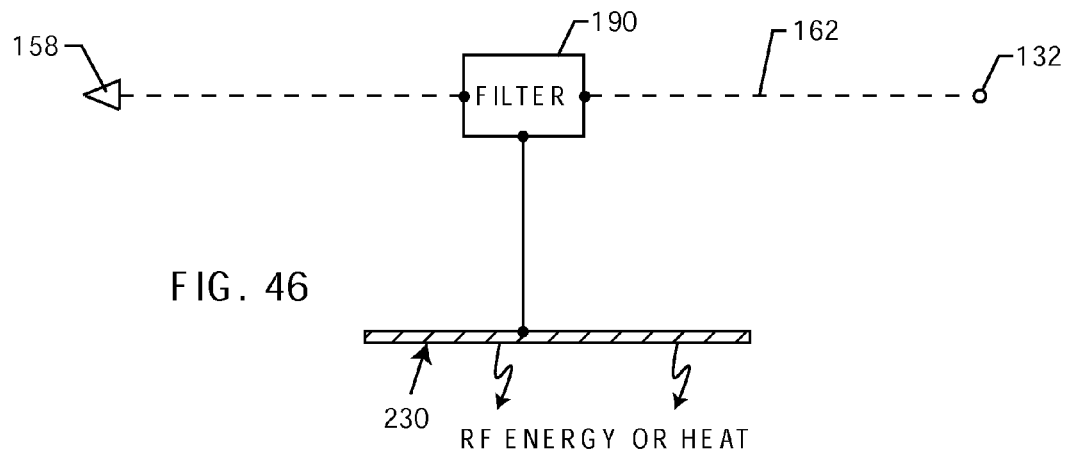
FIG. 46 illustrates how any of the lowpass filters of FIG. 45 can be placed in series with an implanted lead conductor.

FIG. 46 illustrates that any of the lowpass filters 190 previously illustrated in FIG. 45 can be placed in series in a lead conductor 162 between a proximal end 132 and a distal electrode 158. The energy dissipating surface 230 can be the lead body or any other type of metallic or non-metallic energy dissipating surface area associated with the lead. One is referred to U.S. Patent Publication 2010/0217262, the contents of which are incorporated herein by reference.

Figure 47:
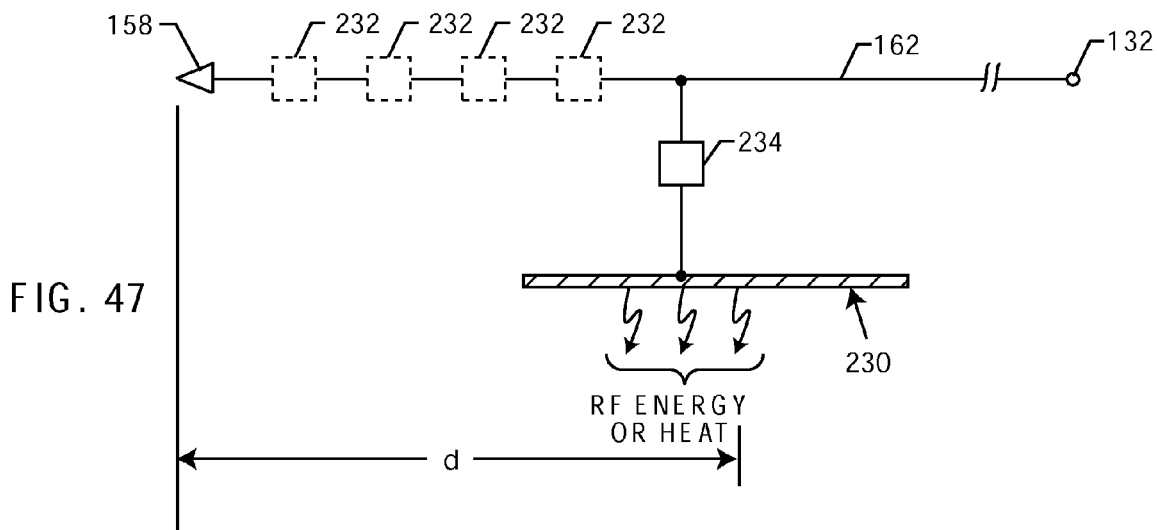
FIG. 47 illustrates that the lowpass filters of FIGS. 45 and 46 can be combined with any number of impeders or diverters.

FIG. 47 illustrates that the lowpass filter elements 190 of FIGS. 45 and 46 can be combined with any number of impeders 232, which in a particularly preferred embodiment, include one or more bandstop filters. As previously described, the lowpass filter 190 may be a simple series inductor 196 or any of the lowpass filter circuits 190 as previously described in FIG. 45. FIG. 47 shows an RF energy or heat dissipating surface 230 which could be the lead body, an outer electrically floating shield or other metallic surface used as an energy dissipating surface. For a more complete description of energy dissipation surfaces one is referred to U.S. Pat. No. 7,689,288 the contents of which are incorporated herein. Importantly, the RF or energy dissipating surface 230 of FIG. 47 could also be the lead body itself. There is a distributive capacitance that is formed between a lead conductor 162 and its surrounding insulative material in the lead body. When used in combination with the present invention, this becomes a great advantage. For example, in the case where the impeder element 232 is a bandstop filter 192, and the bandstop filter 192 was formed by parasitic capacitance 228 in parallel with inductive coils 196, then the diverter 234 would be a distributive capacitance 198 that would appear along the lead 162 to the lead or catheter body 230. This would have the effect of forming a Pi or n—multi element filter as illustrated in FIG. 45. In summary, the composite RF current attenuator 188 of the present invention can consist of a simple inductor lowpass filter 196 in series with a bandstop filter 192, or it can consist of more complicated lowpass filters 190 such as shown in FIG. 45 in series with a bandstop filter 192. A careful designer can carefully specify the inductance per unit length and control the distributive capacitance values that result from lead construction. Capacitance value, of course, depends on surface area of the thickness of the insulation and the dielectric constant of the lead body insulation.

Figure 48:
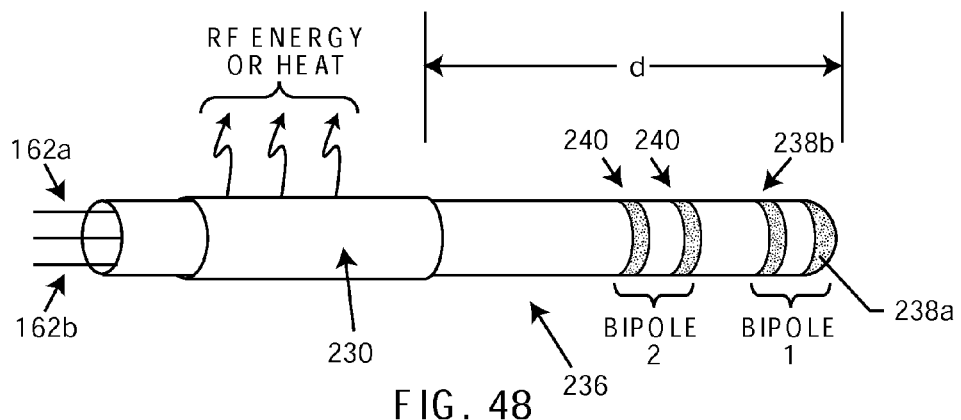
FIG. 48 is a fragmented perspective view of a probe or catheter that has both sense and ablation electrodes.

FIG. 48 illustrates an RF ablation probe or catheter 236 which includes distal ablation electrodes 238a and 238b. Also shown are sense electrodes 240a and 240b, which would typically be used for cardiac mapping. A typical type of ablation would be atrial pulmonary vein ablation. This is a very precise and difficult process wherein one creates a circumferential scar all the way around the pulmonary veins. Typically, this is done to prevent or eliminate atrial fibrillation. It would be an enormous advantage if one could perform this procedure during real time MRI imaging. The reason for this is that MRI is capable of imaging soft tissue and also capable of imaging the formation of the scar in real time. However, in order to enable this very important procedure, it is important that the distal electrodes 238 not pick up too much RF energy from the MRI RF-pulsed field such that ablation could occur inadvertently. In other words, it is very important that the electrodes 238a, 238b and 240a and 240b remain cool. It is only when the ablation tip 238a is in the precise location that one provides the RF ablation energy to create the scar. There are other types of ablation that are typically done, such as in the ventricle to control various ventricular arrhythmias and/or RF ablation treatment of various cancers.

Figure 49:
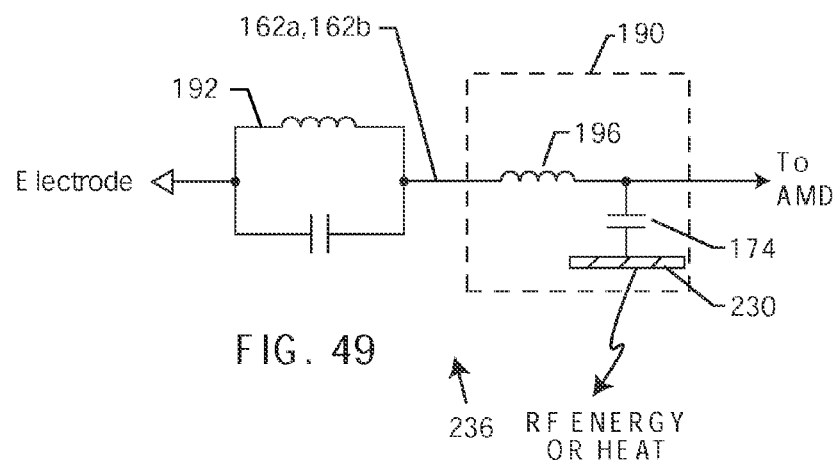
FIG. 49 illustrates that any of the lowpass filters of FIG. 45 can be combined with a bandstop filter.

FIG. 49 is an electrical schematic taken of the filter 190 placed in series with each one of the lead conductors 162a, 162b for the RF ablation catheter 236 illustrated in FIG. 48. Shown is an L-type lowpass filter 190 consisting of a series inductance 196 and a capacitance 174 (which may be a parasitic capacitance) to an energy dissipating surface 230. As previously described, the bandstop filter 192 provides a very high impedance, for example, at 1.5 Tesla (64 MHz) and the L filter provides broadband attenuation to higher MRI frequency system, such as 3 Tesla and higher. The L filter 190 in conjunction with the bandstop filter 192 forms a composite RF current attenuator 188.

Figure 50:
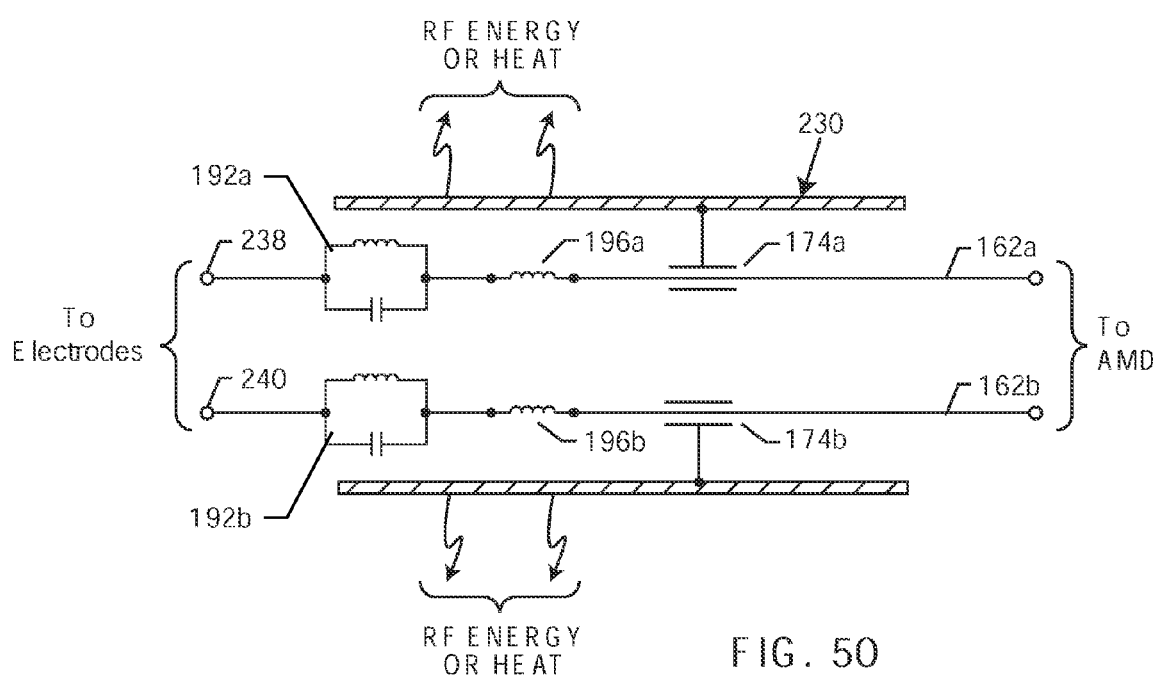
FIG. 50 illustrates how the present invention can be combined with a diverter (L filter shown in FIG. 45) to an energy dissipating surface (EDS)

FIG. 50 is a schematic diagram of the energy dissipating surface 230 illustrated in FIG. 49. In this case, a cylindrical metallic structure is placed around the lead body 162a, 162b in order to efficiently dissipate RF energy or heat into surrounding body fluids and tissues. Shown are the bandstop filter 192a, 192b in series with the inductor 196a, 196b of the present invention along with a capacitance 174a, 174b. In other words, what is formed is a L-type lowpass filter 190 in series with a bandstop filter 192 to provide a composite RF current attenuator 188 having broadband attenuation over a wide range of MRI RF-pulsed frequencies.

Figure 51:
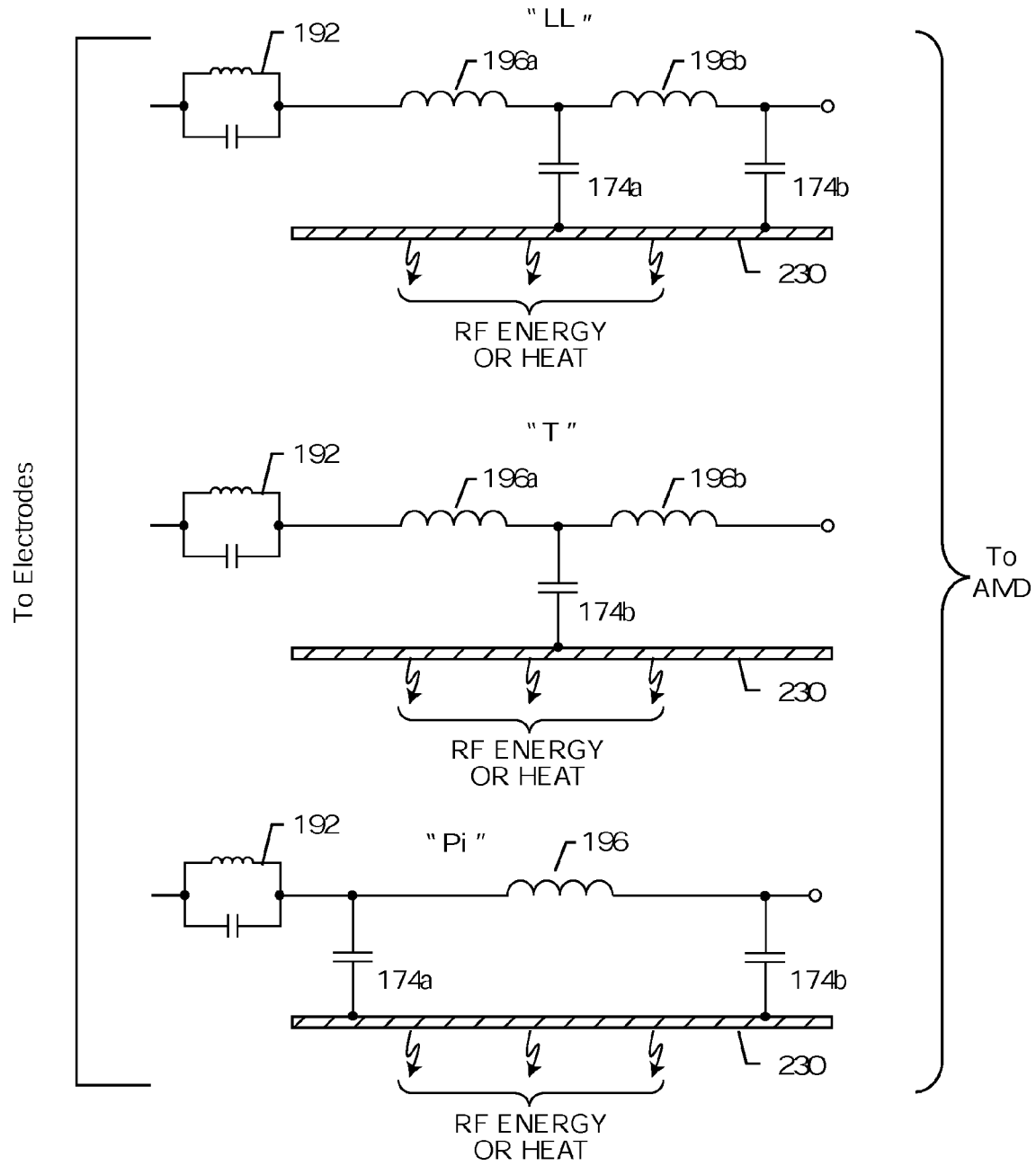
FIG. 51 illustrates LL, T and Pi filters associated with the energy dissipating surface (EDS)

FIG. 51 illustrates that the bandstop filters 192 of FIG. 50 can be combined with other types of lowpass filters 190, such as LL, T or Pi as illustrated.

Figure 52:
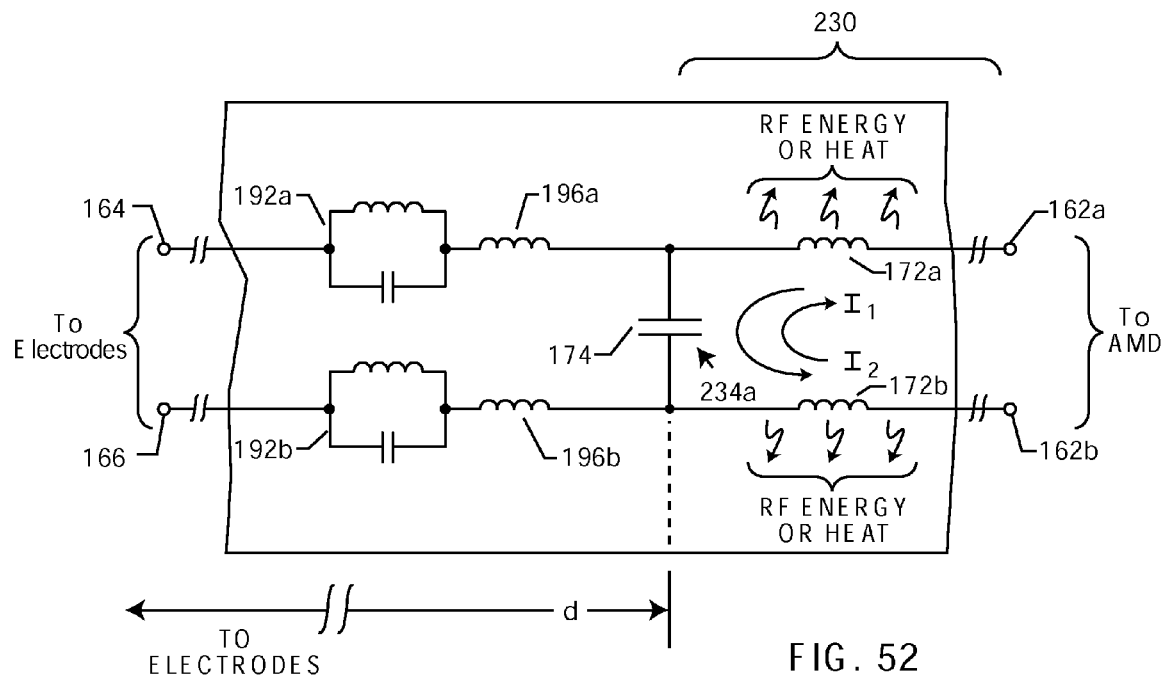
FIG. 52 is a schematic circuit diagram illustrating a bipolar lead assembly with distal Tip and Ring electrodes shown at a suitable distance from an energy dissipation surface (EDS)

FIG. 52 illustrates a bipolar lead of the present invention with distal tip and ring electrodes 164, 166 shown distally at a suitable distance d from an energy dissipation surface 230 such that energy dissipation would not cause a temperature rise at the distal electrodes. Shown is a capacitor 174 connected between the lead conductors 162a and 162b. Also shown are a pair of bandstop filters 192a and 192b as illustrated in FIG. 50. Also shown are a pair of lowpass filters 196a and 196b as illustrated in FIG. 50. Referring once again to FIG. 52, one can see that the capacitor element 174 acts as a high frequency energy diverter 234. This works in cooperation with the two lowpass filter inductors 196a and 196b and the two bandstop filter elements 192a and 192b, which act as energy impeders at a selected MRI RF-pulsed center frequency. Accordingly, high frequency energy that is induced on the lead conductors 162a and 162b at inductors 172a and 172b is converted to RF circulation currents $I_1$ and $I_2$. $I_1$ and $I_2$ are shown in opposite directions to illustrate, for example, for a 1.5 Tesla MRI system, that these oscillate back at 64 million times per second. This creates a great deal of current in the associated lead conductors to the right (as viewed in FIG. 52) of the diverting element 234. This causes heat to be dissipated along the lead conductors 162a and 162b into the energy dissipating surface 230 such as the overall insulation sheath or shield of the probe, catheter or implanted device as shown.

Figure 53:
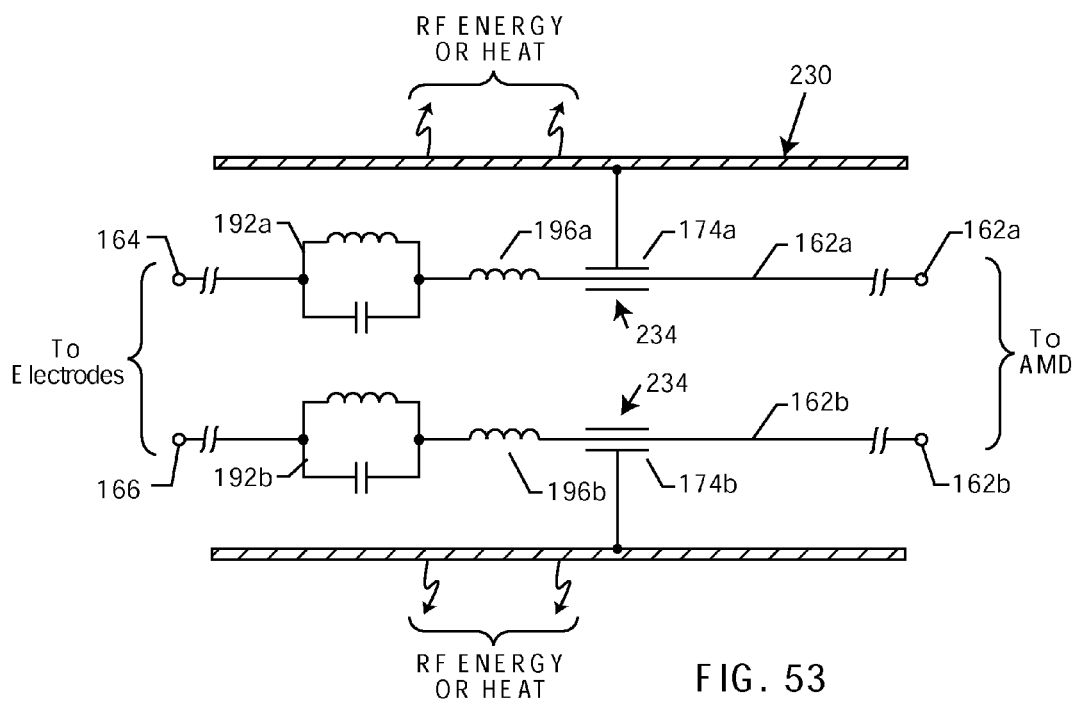
FIG. 53 is a schematic circuit diagram similar to FIG. 52, except that a pair of diverter capacitors are used.

FIG. 53 is very similar to FIG. 52 except that diverting element 234 has been replaced by a pair of capacitor elements 174a and 174b which connect from lead conductors 162a and 162b respectively to an electromagnetic shield or an energy dissipating surface 230. It is a desirable property of the present invention that the energy dissipating surface 230 be thermally conductive, have relatively high surface area for efficient transfer of RF or heat energy into surrounding fluids and body tissue and also be electrically conductive at RF frequencies.

Figure 54:
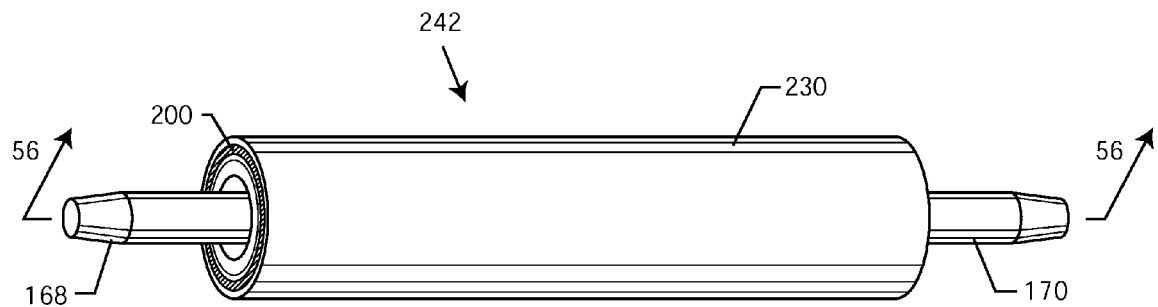
FIG. 54 is a perspective view of a hermetically sealed composite RF current attenuator embodying the present invention.

With reference to FIG. 54, custom or "off-the-shelf" non-biocompatible miniature inductor 198 and capacitor 200 components may be mechanically installed in hermetic packages or containers 242 in series, but have electrical circuit traces that couple the lumped inductor and capacitor elements electronically in parallel, thereby forming bandstop filters 192 as described above. These types of hermetically contained bandstop filters are more thoroughly described in U.S. Pat. No. 7,920,910, which is incorporated herein by reference. FIG. 54 illustrates an hermetically sealed container 242 having the inductor 198 and capacitor 200 components installed therein in series with one another, but whose lumped L and C elements are coupled electronically in parallel, so as to form one or more bandstop filters 192. The hermetically sealed container 242 is very small in diameter or cross-section and can be disposed between portions of an implantable lead 162, within an electrode assembly, etc.

Figure 55:
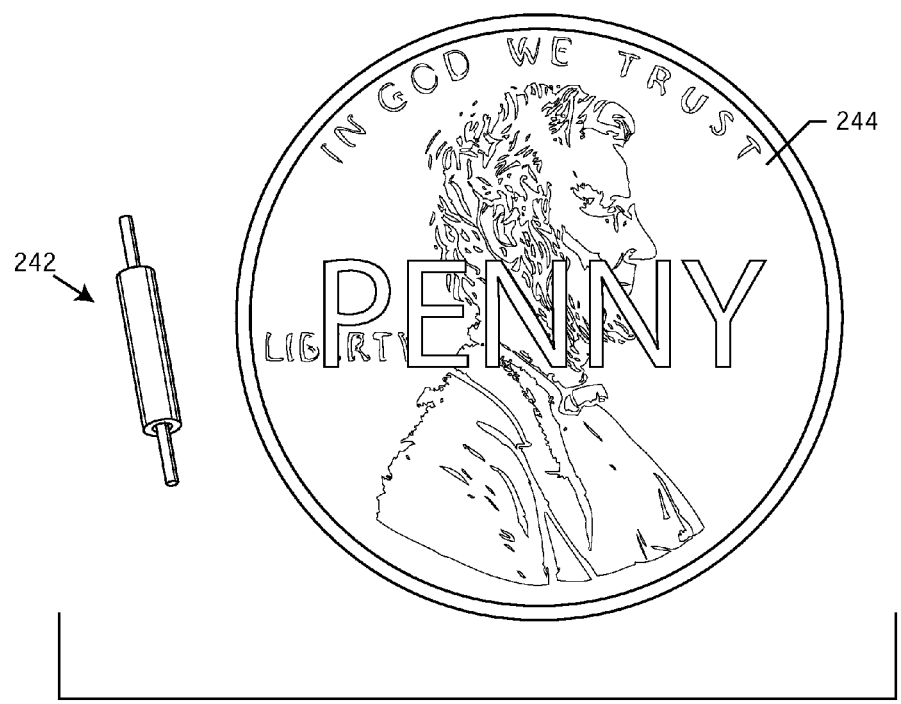
FIG. 55 is an illustration of how small the hermetically sealed assembly of FIG. 54 is in comparison with a U.S. one-cent coin.

FIG. 55 shows the exemplary hermetically sealed container 242 adjacent to a United States penny or one-cent coin 244.

Figure 56:
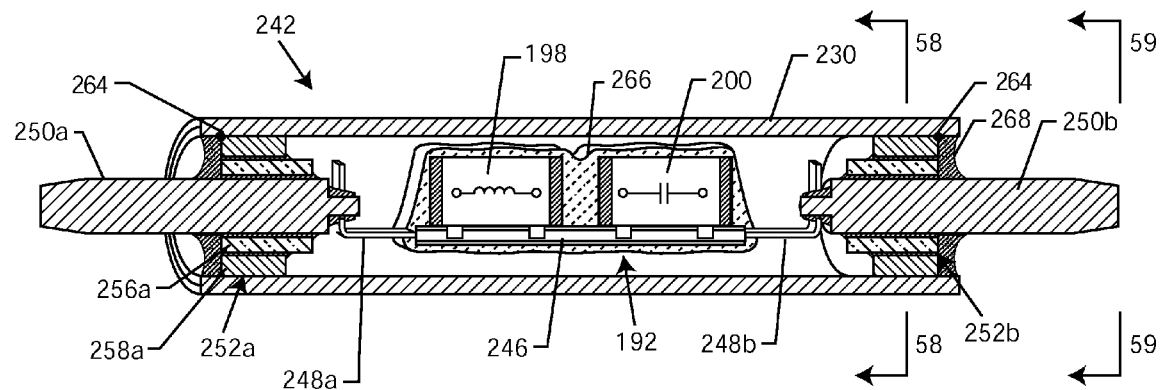
FIG. 56 is a cross-sectional view taken generally along the line 56-56 from FIG. 54.

FIG. 56 is a cross-sectional view taken generally along line 56-56 of FIG. 54 and shows the various component parts of the hermetically sealed container 242. The container 242 comprises a housing 230 which is biocompatible. By way of example, the housing 230 can be comprised of a biocompatible metal or alloy, such as titanium, platinum, platinum-iridium, gold, silver, etc., or a non-metallic material such as sapphire, ruby, alumina, ceramic, etc. The inductor 198 and the capacitor 200 are disposed on a substrate 246 and physically arranged in series, or end-to-end, with one another yet conductively or electronically coupled to one another in parallel. Circuit traces 248a and 248b are conductively coupled to the inductor 198 and capacitor 200 of the bandstop filter 192 and extend to conductive terminals 250a and 250b of hermetic seal assemblies 252a and 252b. The conductive terminals 250a and 250b are designed to be conductively coupled to portions of the implantable lead 162 or electrode assembly, and that any conductive members which can be conductively coupled to the bandstop filter 192 within container 242 and extend therethrough in a hermetic fashion could be used.

Figure 57:
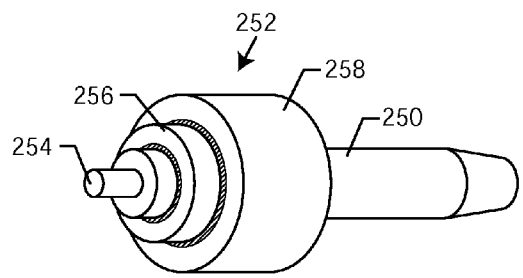
FIG. 57 is a perspective view of a hermetic terminal shown in FIG. 56.

FIG. 57 is an enlarged perspective view of the hermetic seal assembly 252, having the terminal 250 extending therethrough to a crimp, solder joint or laser weld tip 254. The electrical connection to the tip 254 could also be formed by thermal-setting conductive adhesives. The terminal 250 is attached to an insulator 256, which is in turn attached to an outer ferrule 258.

Figure 58:
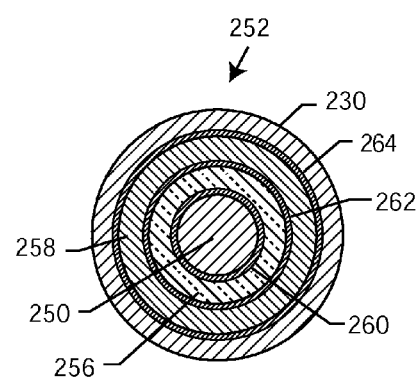
FIG. 58 is a sectional view of the hermetic terminal taken generally along the line 58-58 from FIG. 56.

FIG. 58 is a cross-section drawing taken along line 58-58 from FIG. 56. The terminal 250 is preferably of niobium or a common platinum-iridium alloy, such as 9010 or 8020. However, any biocompatible and suitable material could be used in place of platinum-iridium. Gold braze 260 forms a hermetic seal between terminal 250 and insulator 256. The insulator 256 may be a polished sapphire, ruby, polycrystalline alumina, or even glass or a general ceramic material. Sputtering would first be deposited on the surfaces so that the gold braze 260 will readily adhere and wet. Gold braze 262 forms a hermetic seal between insulator 256 and the ferrule 258. Gold brazes 260 and 262 are generally pure gold brazes for biocompatibility and long term reliability. The surface preparation process for the ceramic insulator 256 can be as follows: C-Axis single crystal, polycrystalline alumina (A1203), Zirconia Stabilized Alumina and/or Yttria Tetragonal Zirconia Polycrystalline YTZP is etched using RF plasma before PVD sputtering using a biologically compatible metallic system. Plasma cleaning removes organic surface contamination and hydroxyl/oxides resulting in a higher energy surface. This activated surface readily forms strong covalent bonds with metallization atoms promoting robust, hermetic adhesion. Through industry standard process refinements, the resulting low stress, dense coating does not spall off or blister and improves the function and reliability of the final brazed joint. The outer ferrule 258 is also, preferably, of platinum-iridium since it's very easy to laser weld. It is also radio-opaque.

In FIG. 57, one can see that the interior tip 254 of the terminals 250a and 250b has been extruded to be fitted into an aperture, socket, etc. of the conductive substrate or circuit traces 248a and 248b. Alternatively, the interior tip 254 may have an aperture therethrough so that a crimped connection can be formed between it and the conductive substrate or circuit traces 248a and 248b, and subsequently laser welded. The method of attachment to the interior tip 254 will vary in accordance with the type of attachment desired to the internal circuitry of the bandstop filter 192. In any event, the conductive terminals 250a and 250b are conductively coupled to the bandstop filter 192 as the associated hermetic seal assemblies 252a and 252b are slid into place and hermetically sealed by laser welding 264 to the housing 230 of the container 242.

FIG. 56 shows the bandstop filter 192 comprised of the inductor 198 and capacitor 200, and the flexible circuit substrates 248a and 248b extending therefrom, attached to the terminals 250a and 250b so as to place the terminals 250a and 250b in electrical series with one another. However, the inductor 198 and the capacitor 200, although placed end-to-end and physically in series with one another, are conductively coupled electrically with one another in parallel. An insulating material 266, such as a thermal-setting non-conductive polymer, at least partially fills the remainder of the housing 230 to provide protection and mechanical robustness to the overall container assembly 242. This structure lends itself to a novel "ship-in-the-bottle" method of manufacturing. That is, all of the elements contained within the housing 230 are pre-assembled outside the housing. In particular, the terminal 250a, the substrate 246 containing the inductor 198 and capacitor 200, and the opposite terminal 250b and the associated hermetic seals 252a and 252b, are all pre-assembled outside of the overall housing 230. This facilitates proper electrical connections and electrical testing of the pre-assembly. In addition, this entire subassembly can go through high reliability screening. Typically, this would consist of thermal cycling or thermal shock followed by a burn-in, which means applying a relatively high voltage at elevated temperature to the circuit components and then exhaustive electrical test afterwards. Once all of this has been done, this entire pre-assembly is slipped inside the overall cylindrical housing 230 and then a final continuous hermetic seal laser weld 264 is formed.

Figure 59:
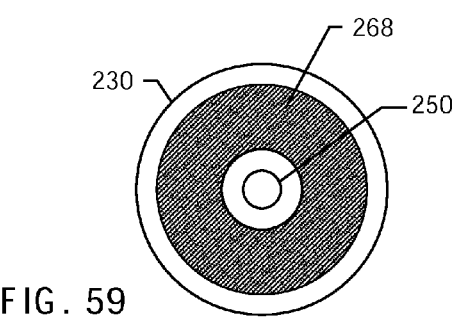
FIG. 59 is an elevational view taken generally along the line 59-59 from FIG. 56.

FIGS. 56 and 59 also show an optional conformal coating 268 which is provided over the two gold brazes 260 and 262. This conformal coating 268 could also be applied to the entire outer surface of the housing 230 and a portion of terminals 250a and 250b, as well as optionally over the electrical attachments to the lead system. This conformal coating 268 is important to provide electrical isolation between the two terminals 250a and 250b. When directly exposed to body fluids (which contain electrolytes), gold can migrate in the presence of a voltage bias. It has been shown that pacemaker pacing pulses in saline solution can actually cause a gold electromigration or electroplating action. The concern is that the gold braze materials 260 and/or 262, under voltage or pulse bias, may over time migrate or deposit (electro-plate) onto another surface such as the terminal 250b or the housing 230, which could negatively affect the long-term hermeticity and reliability of the hermetic seal assembly 252b. Accordingly, the conformal coating or backfill 268 is placed as shown to cover both of the gold brazes 260 and 262. The conformal coating 268 may comprise thermal-setting non-conductive adhesives, silicones, parylene (which is vapor deposited), and the like, including epoxies, polyimides, polyethylene oxide, polyurethane, silicone, polyesters, polycarbonate, polyethylene, polyvinyl chloride, polypropylene, methylacrylate, para-xylylene, and polypyrrhol. In particular, Epo-tek H81 is considered a preferred epoxy which has already been tested for long-term biocompatibility.

A complete conformal coating 268 over the entire housing 230 may be desirable to provide electrical isolation between the conductive terminal pins 250a and 250b. This provides critical performance capability in the event of complete saturation of the housing 230 in saline or biological fluid. Additional performance benefits for a conformal coating 268 include lubricity, radiopacity, and wear resistance.

Figure 60:
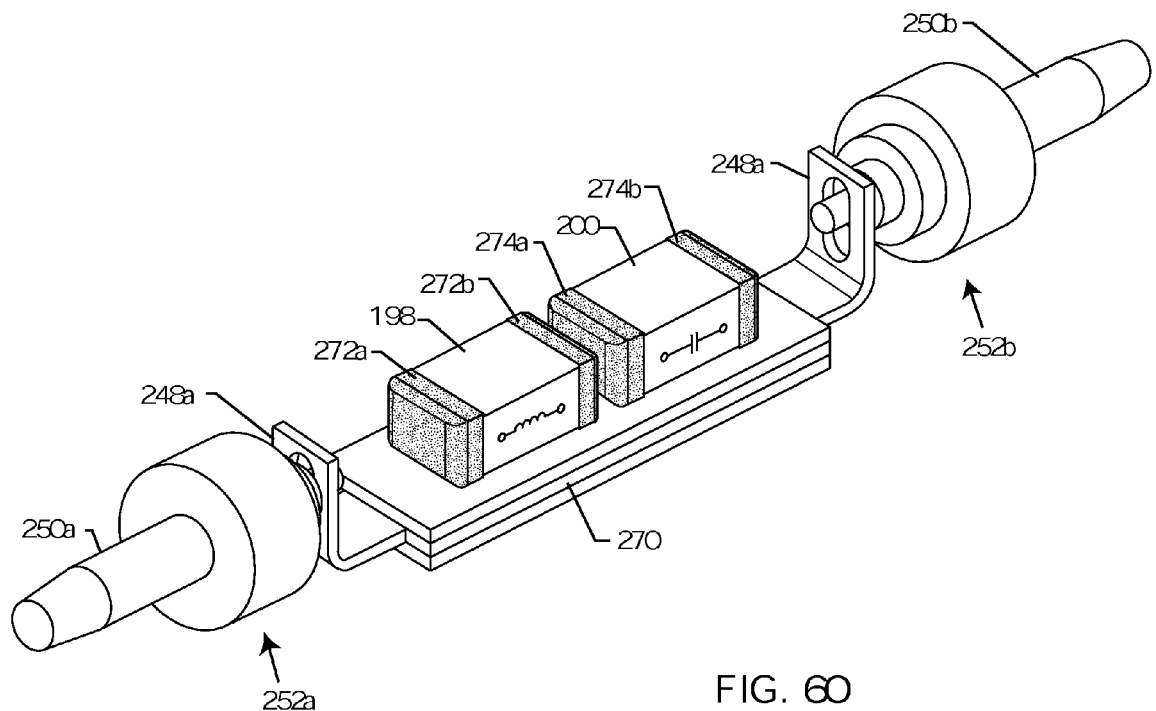
FIG. 60 is a perspective view illustrating a multilayer flex cable onto which a chip capacitor and a chip inductor are mounted to form a parallel L-C bandstop filter.
Figure 61:
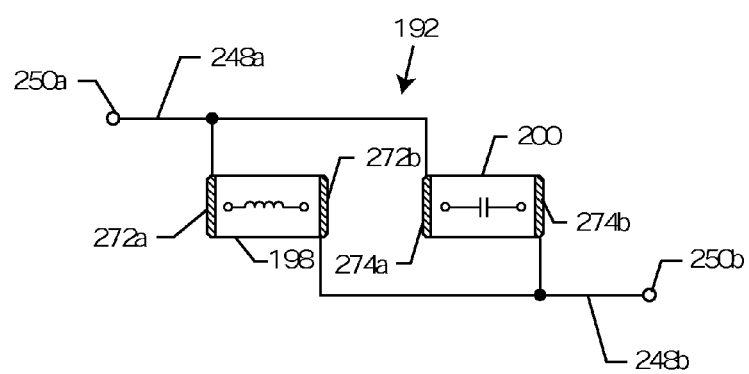
FIG. 61 is an electrical physical schematic of the bandstop filter assembly of FIGS. 56 and 60, illustrating conductive pathways and electrical connections to the serially arranged capacitor and inductor.

FIG. 60 illustrates a multi-layer flex cable or circuit board/substrate 270 onto which the inductor 198 and capacitor 200 are mounted. The inductor 198 is a chip inductor having first and second conductive termination surfaces 272a and 272b which are spaced from one another in non-conductive relation. The capacitor 200 also has first and second conductive termination surfaces 274a and 274b which are spaced apart from one another in non-conductive relation. The chip inductor 198 can be any number of chip inductor types; however the present invention is also not limited to chip inductors only. The inductor 198 could also be a solenoid inductor, a toroidal inductor, or any type of inductor that is known in the prior art. Moreover, the chip capacitor 200 can be any number of chip capacitor types, but the present invention is not limited to chip capacitors only. The capacitor 200 may be of many different types of capacitor technologies, including film capacitors, tantalum capacitors, monolithic ceramic capacitors, electrolytic capacitors, feedthrough-type capacitors, or even tubular capacitors. FIG. 60 shows that the inductor 198 and the capacitor 200 are physically disposed in series relative to one another, such that they are generally aligned with one another along a common longitudinal axis and placed end-to-end. However, in accordance with the present invention, the inductor 198 and the capacitor 200 are conductively or electrically coupled to one another in parallel. FIGS. 16 and 20 are electrical schematic diagrams of the bandstop filter of FIGS. 60 and 61. When electrically connected as shown in FIG. 61, the second conductive terminal 272b of the inductor 198 is spaced a suitable distance away from the first conductive terminal 274a of the capacitor 200. The reason that these termination surfaces 272b and 274a must be placed apart is that in the presence of an MRI scanner, a substantial RF voltage can be generated across this gap. Arcing or even short circuits may undesirably occur. Another concern is that a long term failure may occur due to the formation of metal dendrites or whiskers. This can happen even in the presence of a low voltage bias. However, having a large physical gap between the termination surfaces 272b and 274a is generally undesirable because it increases the overall length of the bandstop filter 192. As previously mentioned, the most critical dimension is the diameter. However, it is also important that the overall assembly not get too long.

FIG. 60 may be compared with FIG. 56 to see alternative configurations of the attachment between conductive terminals 250a and 250b, and the conductive circuit traces or electrodes in 248a and 248b. FIG. 56 illustrates a crimp configuration between the circuit traces or conductive substrates 248a and 248b, and the respective tips 254 of the conductive terminals 250a and 250b. In FIG. 60, an alternative configuration is shown wherein the hermetic seal assemblies 252a and 252b are pre-mounted to the conductive circuit traces or substrates 248a and 248b, and attached thereto by resistance welding or the like.

Figure 62:
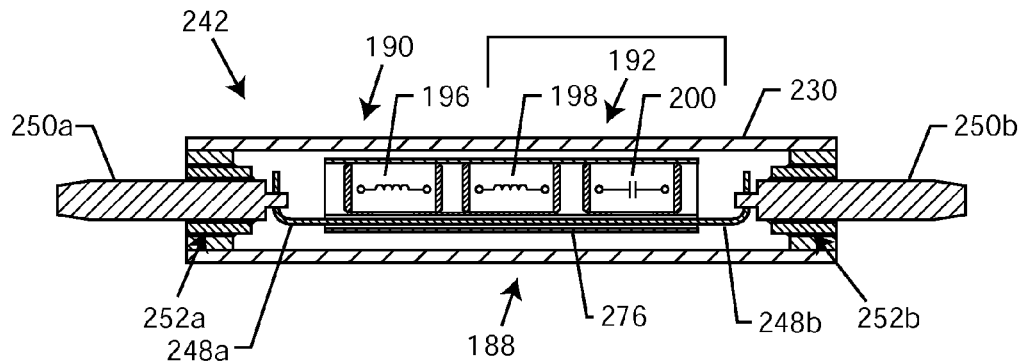
FIG. 62 illustrates the composite RF current attenuator of the present invention housed in a hermetic container similar to FIG. 54.

FIG. 62 is very similar to FIG. 56 except that a broadband lowpass filter 190 having inductor 196 has been placed in series with the bandstop filter 192 having components 198 and 200. As previously mentioned, circuit traces 276 connect that inductor 198 in parallel with the capacitor 200 to form the bandstop filter 192. This forms a composite RF current attenuator 188 of the present invention.

Figure 63:
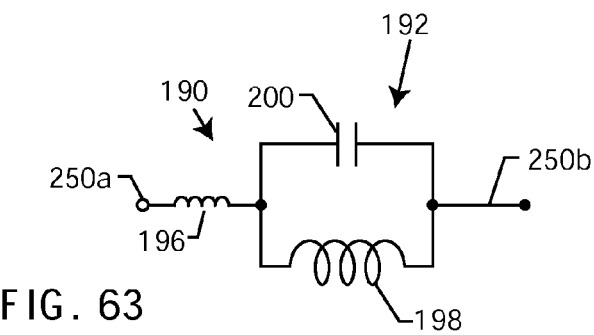
FIG. 63 is an electrical schematic of the composite RF current attenuator of FIG. 62.

FIG. 63 is the electrical schematic for the composite RF current attenuator 188 of FIG. 62.

Figure 64:
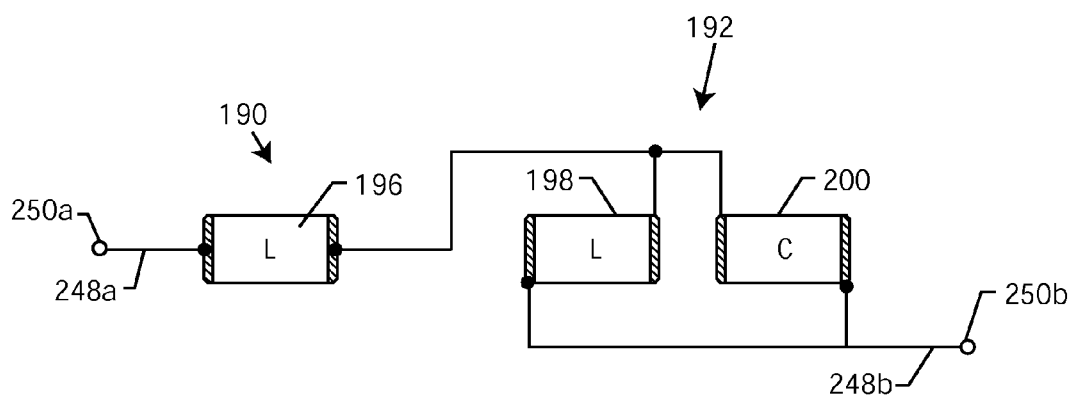
FIG. 64 is an electrical/physical schematic similar to FIG. 61, illustrating preferred conductive pathways and electrical connections for the composite RF current attenuator of FIG. 62.

FIG. 64 is very similar to FIG. 61 and shows a physical/electrical schematic showing the inductor 196 in series with the parallel combination of inductor 198 and 200. In a preferred embodiment, the inductors 196, 198 would be inductor chips and the capacitor 200 would be an MLCC chip capacitor.

FIG. 65 illustrates an exemplary lead 162 which embodies a lead body 230, a coaxial conductor 278 for the ring electrode 166 and coaxial conductor 280 for the tip (active fixation helix) electrode 164, a collar 282, and the translatable casing 242 which houses electronic components. The translatable casing 242 includes a pin 250a and a pin 250b. The pin 250a is electrically and mechanically connected to the tip electrode lead wire conductor 280 and the pin 250b is attached to the translatable seal assembly 284 which is also connected to the distal helix electrode 164. The distal helix electrode 164 is also known as an active fixation electrode. The pin 250a, the casing 242, the pin 250b and the translatable seal structure 284 all form what is defined herein as a casing subassembly 286. This is further illustrated in FIG. 66, which shows the broadband lowpass filter inductive element 190 in series with the bandstop filter 192. These components are all physically disposed in series, but are electronically connected to form the inductor 196 in series with the bandstop filter 192 as shown. This type of filter is further described in U.S. 2010/0100164, which is incorporated herein by reference.

Referring once again to FIG. 65, there will typically be a laser weld (not shown) electrically and mechanically connecting the tip conductor 280 to casing 242 terminal pin 250a. There is also a laser weld 238 connecting the casing pin 250b to a weld sleeve 290 of the translatable seal assembly 284. The weld sleeve 290 may be attached to the pin 250b in any known technique including laser welding, bonding, crimping, adhering, other forms of welding, or any other suitable method. The weld sleeve 290 is typically laser welded to the helix electrode 164. During transvenous insertion, the active fixation helix tip 164 is retracted (as shown) so that it will not stab or poke into body tissues during lead insertion. When the physician has positioned it in the desirable location (perhaps inside the cardiac right ventricle), then the physician takes a special tool and twists the proximal end of lead body 230 tip conductor 280 which causes the entire conductor 280 and casing subassembly 286 to rotate. As the distal helix electrode 164 rotates, it engages a guide 242 which causes the helix 164 to extend and screw into body tissue. The guide 242 may be formed as part of the collar 282 and engages the tip electrode 164 when the tip conductor 280 is rotated. The rotation causes the helical tip electrode 164 to rotate within the collar 282 and thereby translate in a forward manner. At the same time the tip electrode 164 is advancing relative to the collar 282, it is engaging with body tissue by being screwed directly into the tissue forming an attachment. The tip electrode 164 can be rotated in the opposite direction by the tip conductor 280 and thereby disengaged from the tissue for removal and/or reattachment at a different location. This is a method of active affixation which is well known in the art.

FIG. 66 is generally taken from section 66-66 from FIG. 65. Shown is the interior of the translatable casing 242 illustrating the broadband lowpass filter inductor 196 in series with the bandstop filter 192. Shown are terminal pins 250a and 250b which extend in non-conductive relationship with the translatable casing 242. Hermetic seals 294a and 294b are shown which form a hermetic seal between the pins 250a and 250b and the translatable casing 242. This protects the inductor 196 and bandstop filter 192 (or other electronic components) from intrusion of body fluids. It is well known in the art that intrusion of moisture, body fluids or other contaminants can cause electronic circuits to short out. It is not an absolute requirement that the translatable casing 242 be hermetically sealed. Electronic components, such as inductor 196, 198 and capacitor 200 components, could be utilized that are inherently non-toxic and biocompatible. Components for direct body fluid exposure are described in U.S. Pat. No. 7,535,693, the contents of which are incorporated herein.

Referring once again to FIG. 66, the present invention is applicable to any type of combination of lowpass filter and bandstop filters, including those that were previously shown and described in any of the drawing FIGS. herein, including FIGS. 26, 27, 31, 32, 33, 34, 35, 37, 45, 47, 49, 50, 51, 52 and 53, that may be disposed in a translatable electronic casing 242. The flexible seal 296 of FIG. 65 slides against the interior of the collar 282 thereby preventing the entrance of ionic body fluids into the inside of the lead body 230. The seal 296 may be bonded, molded, adhered, or formed onto the weld sleeve 290 by any suitable means. The seal 296 can be formed in a multitude of ways appreciated by those skilled in the art, such as multiple wipers, o-rings, thin disks or sheets, and various molded profiles.

There is a secondary optional O-ring seal 298 as shown in FIG. 65. The O-ring seal 298 is disposed between the inside diameter of the lead collar 282 and the outside diameter of the electronic component casing 242. The purpose of seal 296 and the O-ring seal 298 is to ensure that ionic body fluids cannot be disposed across the important electrical path between pins 250a and 250b. Ionic body fluids could represent a parallel path as low as 80 ohms. Over time, due to bulk permeability, body fluids will penetrate into the interior of the lead body 230. However, this is an osmotic type of action. The resulting fluids that would occur over long periods of time inside the lead body 230 would be distilled and free of ionic contaminants (de-ionized). This means that they would be less conductive of high frequency electrical signals from one end to the other of the electronic component casing 242. The presence of the optional O-ring 298 is desirable in that it also presents a high impedance to such a parallel circuit path. The casing 242 may also have a conformal insulative coating (not shown) for further electrically isolating terminals 250a and 250b such that a parallel path through body fluid is further impeded. The insulative coating may be formed from any suitable material, such as a dielectric material, including, but not limited to parylene, ETFE, PTFE, polyamide, polyurethane and silicone. It will be understood that the exemplary embodiment of FIG. 65 may work with or without such coatings.

Figure 67:
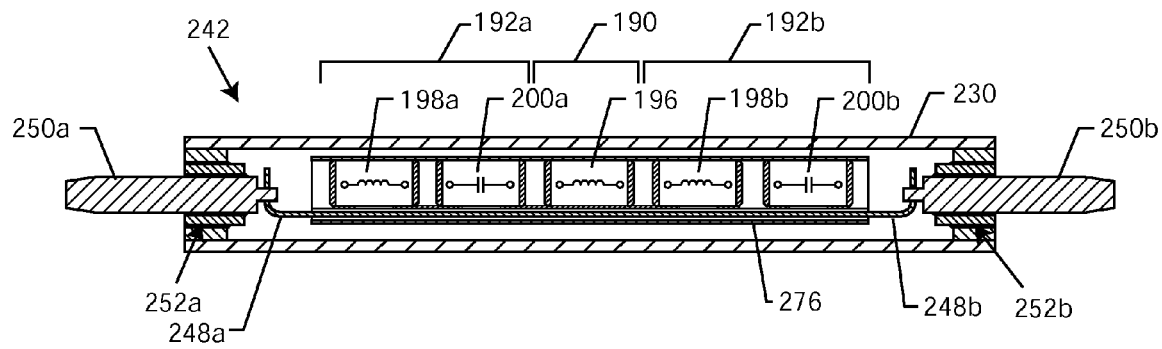
FIG. 67 illustrates another embodiment of the present invention where two bandstop filters have an inductor element placed between them within a hermetically sealed container.
Figure 68:
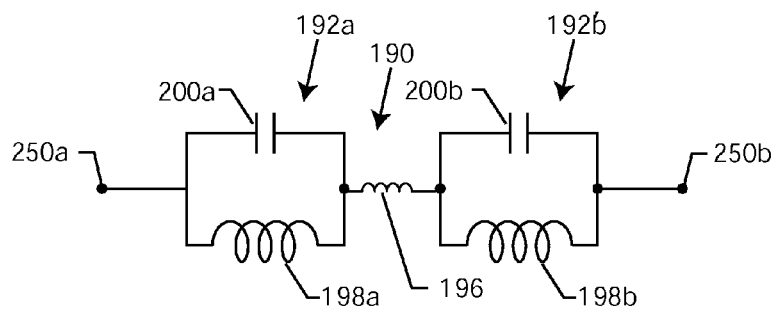
FIG. 68 is an electrical schematic of the dual composite RF current attenuator assembly of FIG. 67.
Figure 69:
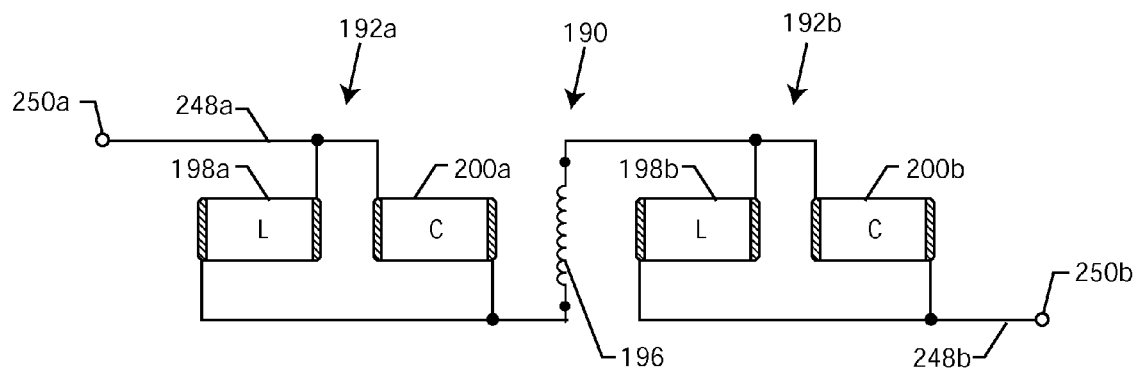
FIG. 69 is an electrical/physical schematic similar to FIGS. 61 and 64, illustrating preferred conductive pathways and electrical connections for the dual composite RF current attenuator assembly of FIG. 67.

FIGS. 67-69 illustrate a configuration where two bandstop filters 192a and 192b are disposed in series with a single element broadband lowpass filter 190 inductor 196 disposed in series between them. Referring to FIG. 67, inductor 198a and capacitor 200a are electrically connected in parallel to form the first bandstop filter 192a. Inductor 196, which may be a chip inductor, is disposed electrically in series, and inductor 198b and capacitor 200b are connected in parallel to form the second bandstop filter 192b.

FIG. 68 is the schematic diagram of the configuration from FIG. 67.

FIG. 69 is a physical/electrical diagram showing the electrical connections wherein the components are physically placed in series, but electrically form one bandstop filter, 192a in series with an inductor, 190 in series with a second bandstop filter 192b. The first conductive substrate or circuit trace 248a cooperates with an intermediate internal circuit trace or conductive substrate (not shown) to conductively couple the capacitor 198a and the inductor 200a of the first bandstop filter 192a in parallel electrical relation with one another, and the second end circuit trace or conductive substrate cooperates with the intermediate circuit trace or conductive substrate to place the inductor 196 in series with the bandstop filters 192a and 192b. The second bandstop filter 192b is formed by the cooperation of the intermediate circuit trace or conductive substrate 248b, which places the inductor 198b in parallel with the capacitor 200b.

Figures 70, 71:
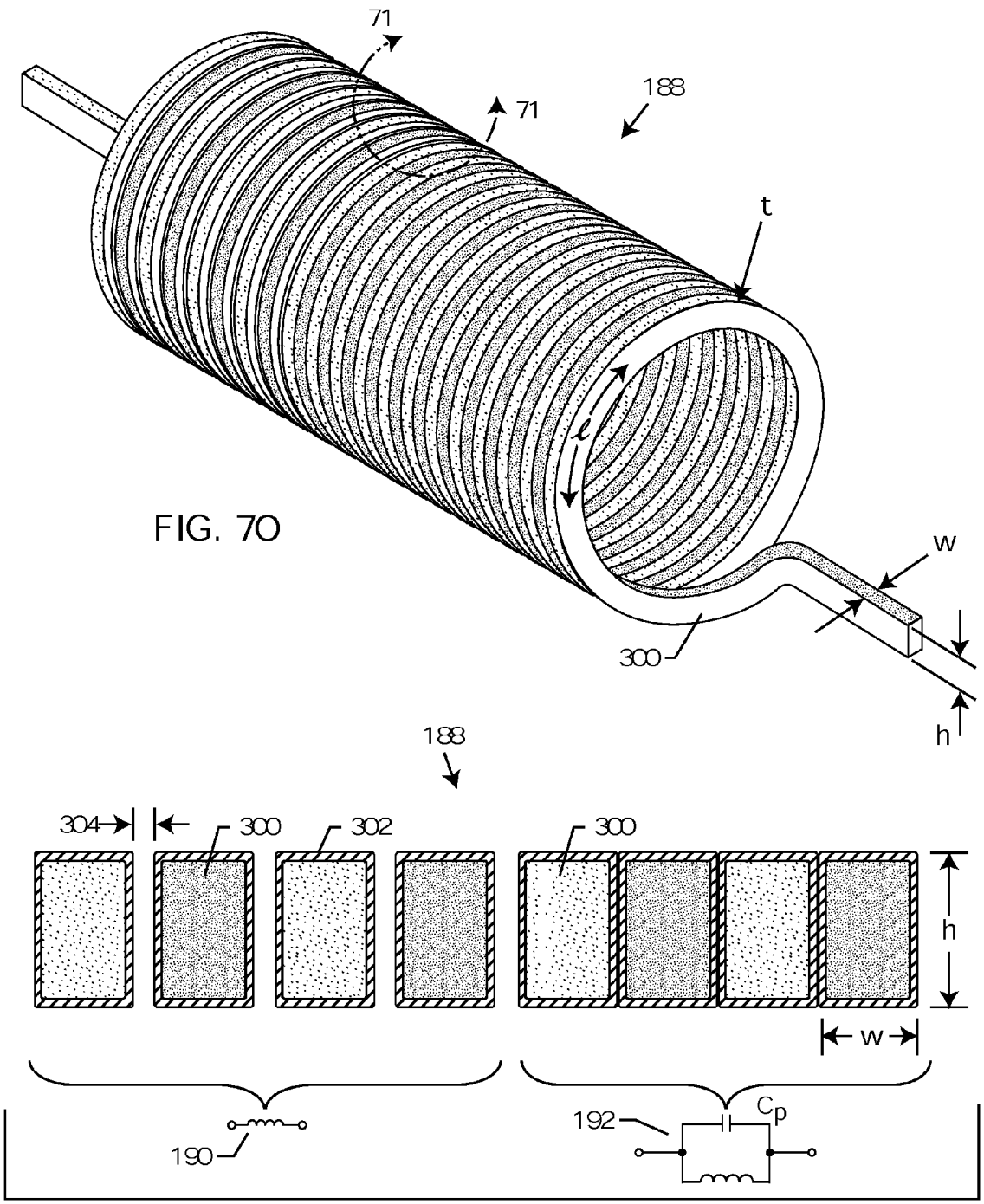
FIG. 70 is an isometric view of a co-radial lead comprising an inductor in series with a bandstop filter which is formed by parasitic capacitance.
FIG. 71 is a sectional view taken generally of the area indicated by line 71-71 of FIG. 70, showing the adjacent conductor turns.

FIG. 70 is an isometric view of a round coaxial winding composite RF current attenuator 188 which is at least a portion of an AMD lead conductor composed of rectangular wire 300 which has a dielectric coating 302. The inductor portion 190 of the coaxial winding 188 has air gaps 304 wherein the turns are spaced apart such that an inductive coil is formed. The BSF portion 192 of the winding 188 is closely spaced such that a parasitic capacitance is formed. This is best illustrated in FIG. 71, which is taken generally from section 71-71 from FIG. 70. The inductor portion 190, shown on the left, has air gaps 304. These spaces or air gaps 304 diminish the parasitic capacitances to the point where, for the present invention, it is trivial. The BSF portion 192 has little to no air gap 304 and hence has a significant amount of parasitic capacitance. This forms a parasitic capacitive inductive bandstop filter 192 as illustrated.

In FIG. 71 the dielectric coating 302 is very important over the bandstop filter portion 192. The dielectric coating 302 can include a high k material such that the parasitic capacitance is increased. In addition, the dielectric coating is insulative, thereby preventing adjacent turns from shorting out to each other and reducing the inductance. The dielectric coating 302 in the inductor portion 190 is optional. In fact, it would be better if there were no dielectric coating 302 in the inductor portion 190 since it's desirable to have little to no parasitic capacitance in this area. Referring once again to FIG. 70, it is preferable that the elongated conductor 300 is of square or rectangular cross-section. The elongated conductor 300 could also be a round cross-section except this tends to reduce the parasitic capacitance area and may also cause undesirable variability in the parasitic capacitance value FIG. 72 illustrates the broadband composite RF current attenuator 188 previously illustrated in FIGS. 70 and 71 with a non-conductive and non-ferromagnetic mandrel 306 and end caps 308a and 308b for convenient mechanical and electrical connection of the composite RF current attenuator 188 in series into one or more conductors of an implantable lead 162 of an AMD 110. The center of the mandrel 306 is preferably hollow to facilitate convenient guide wire transvenous insertion. There are optional valves 310a and 310b which preventingress of body fluids during the insertion process. Hollow bandstop filters for transvenous insertion are described in U.S. Pat. No. 7,702,387. In FIG. 72, one can see that mandrel 306 is a rigid or semi-rigid material such that the inductor coils 190 and bandstop filter coils 192 are held in a mechanically stable position. This is important in that the resulting value of inductance in the inductor 190 and the resulting values of capacitance and inductance in the bandstop filter 192 do not vary either during lead insertion, lead flexure or during repeated movements such as happens with cardiac leads.

An implantable lead may be comprised of material MP35N which is easily laser welded to mandrel end caps 308a and 308b. The composite RF current attenuator 188 of the present invention is disposed between these two end caps. End cap 308a would be in series with a distal electrode 164 in contact with body tissues. The composite RF current attenuator 188 of the present invention can be disposed anywhere along the length of the implanted lead 162. However, in a particularly preferred embodiment, it is disposed at, near or within the lead distal electrode(s) 164. An active fixation tip electrode assembly 312 may be electrically and mechanically connected to end cap 308b.

FIG. 73 is a schematic diagram of the composite RF current attenuator 188 illustrated in FIGS. 70 and 72.

Figure 74:
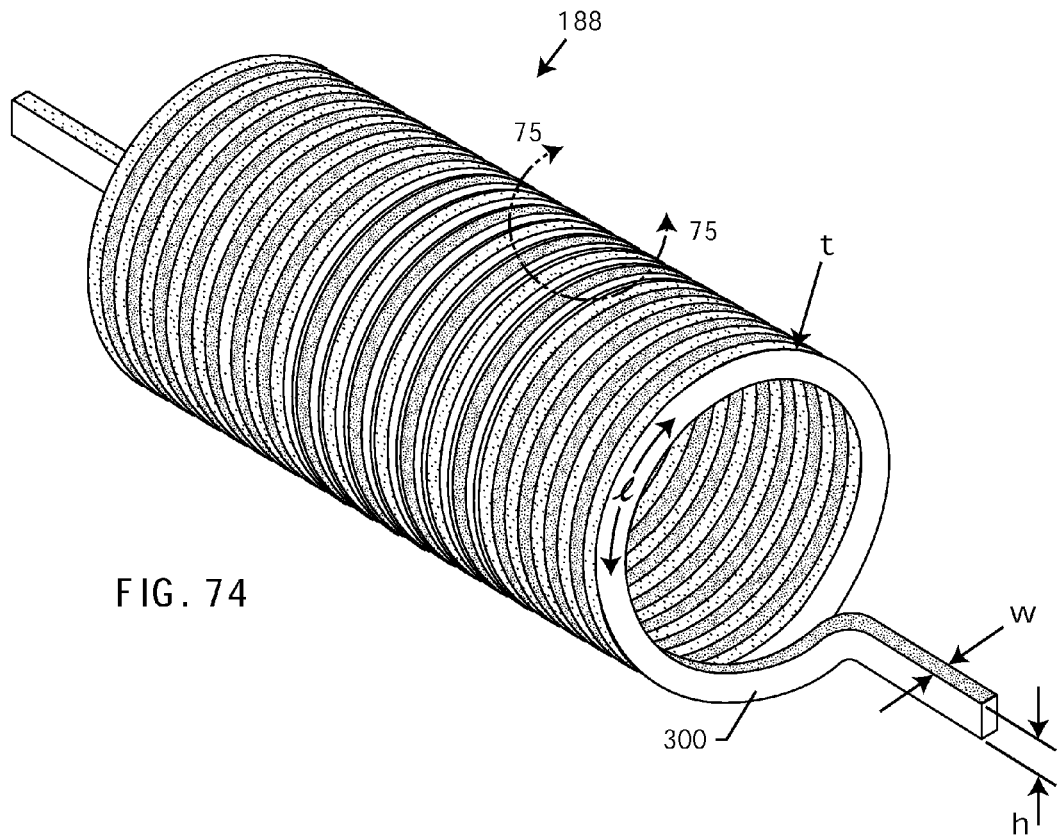
FIG. 74 is an isometric view of a series lowpass filter inductor-parasitic capacitor bandstop filter embodying the present invention.

FIG. 74 is an isometric view of a composite RF current attenuator 188 having an inductive portion 190 in series with a first 192a and a second 192b parasitic capacitive-inductive bandstop filter. This composite RF current attenuator 188 is formed from one continuous wound elongated electrical conductor 300. Different shadings are shown to illustrate each individual turns and the air gaps 304 and the fact that the coil turns of both of the parasitic capacitance-inductive bandstop filters 192a and 192b are preferably closely spaced. In a particularly preferred embodiment, the elongated conductor 300 is of square or rectangular cross-section. The elongated conductor 300 could also be a round cross-section except that this tends to reduce the parasitic capacitance area and may also cause undesirable variability in the parasitic capacitance value. The center of the composite RF current attenuator 188 is preferably left hollow to facilitate transvenous guidewire insertion. Hollow bandstop filters for guidewire insertion are described in U.S. Pat. No. 7,702,387.

Figure 75:
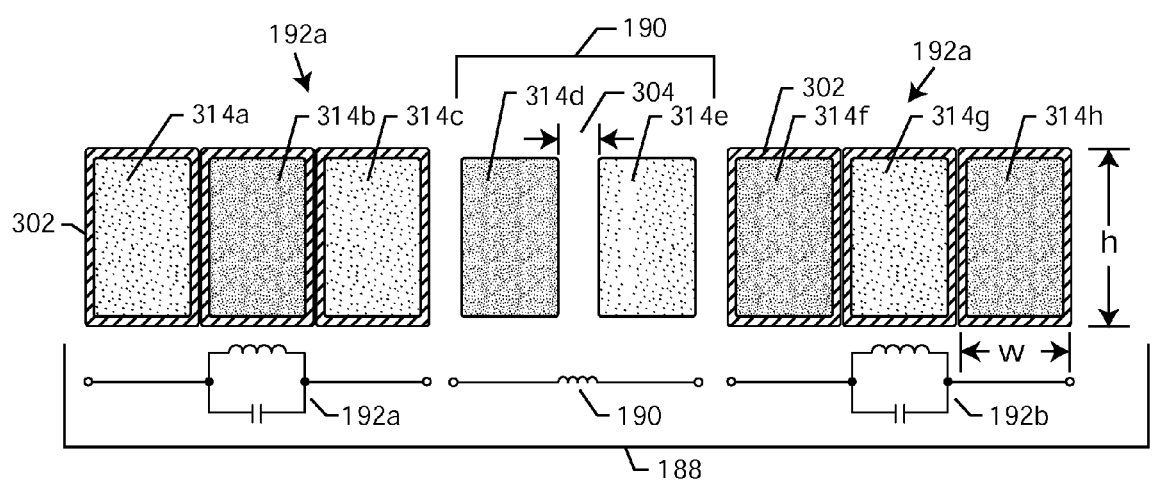
FIG. 75 is a sectional view taken generally from section 75-75 of FIG. 74, showing the adjacent inductor turns.

FIG. 75 is a sectional view generally taken from section 75-75 of FIG. 74. Shown are adjacent turns 314a-314c, which forms a first parasitic capacitance bandstop filter 192a and then turns 314d and 314e, which form an inductive portion 190 with air gaps 304 and minimal parasitic capacitance, and a second parasitic capacitance bandstop filter 192b formed by turns 314f through 314h. Referring once again to FIG. 75, it will be obvious to those skilled in the art that a much higher number of turns would be required for all three segments of the filter 188. Three turns are shown for the bandstop filters 192a, 192b and two turns are shown for the inductor 190 just for simplicity. However, it should be apparent that any number of turns could be used for each of the sections. It is important that turns 314a through 314c and turns 314f through 314h have a dielectric coating 302, for several reasons: 1) so that the individual turns of the inductive coil 300 do not short out to each other; 2) to provide a material with a uniform thickness and dielectric constant so that a significant and consistent parasitic capacitance Cp is formed; and (3) the dielectric coating material 302 has a much higher dielectric constant than air, thereby allowing one to increase or tune the parasitic capacitance Cp between adjacent coils. The dielectric coating 302 is optional for the inductor turns 314d through 314e. These turns are spaced further apart with air gaps 304 in order to reduce parasitic capacitance. Of course, these adjacent turns will still have some parasitic capacitance. However, it's preferable that the value of parasitic capacitance be so low such that this inductive portion 190 does not self-resonate at the MRI frequencies of interest. Dielectric coating material 302 is also important so that the adjacent turns such as 314*f* and 314*g* do not short out to one another.

Figure 76:
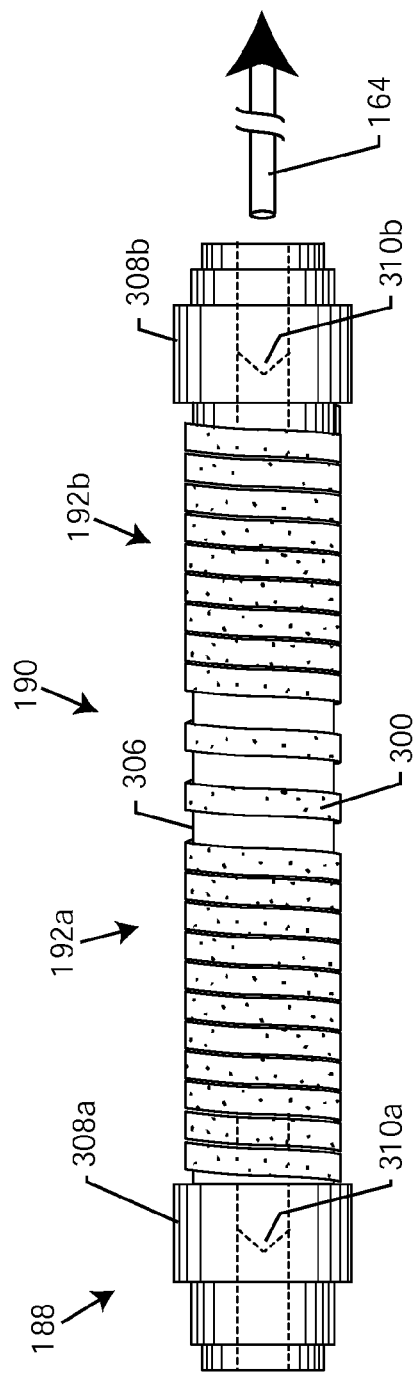
FIG. 76 is an elevational view of a lowpass inductor-parasitic capacitance dual bandstop filter with end caps for convenient mechanical and electrical connection in series with an implanted lead conductor.

FIG. 76 illustrates the three-section composite RF current attenuator 188 previously illustrated in FIGS. 74 and 75 with a non-conductive and non-ferromagnetic mandrel 306 and end caps 308*a* and 308*b* for convenient mechanical and electrical connection of the composite RF current attenuator 188 in series into one or more conductors of an implantable lead 162 of an AMD 110. The center of the mandrel 306 is preferably hollow to facilitate convenient guide wire transvenous insertion. There are optional valves 310*a* and 310*b* which preventingress of body fluids during the insertion process. Hollow bandstop filters for transvenous insertion are described in U.S. Pat. No. 7,702,387.

An implantable lead may be comprised of material MP35N which is easily laser welded to mandrel end caps 308*a* and 308*b*. The composite RF current attenuator 188 of the present invention is disposed between these two end caps. End cap 308*a* would be in series with a distal electrode 164 in contact with body tissues. The composite RF current attenuator 188 of the present invention can be disposed anywhere along the length of the implanted lead 162. However, in a particularly preferred embodiment, it is disposed at, near or within the lead distal electrode(s) 164. An active fixation tip electrode assembly 312 may be electrically and mechanically connected to end cap 308*b*.

Figure 77:
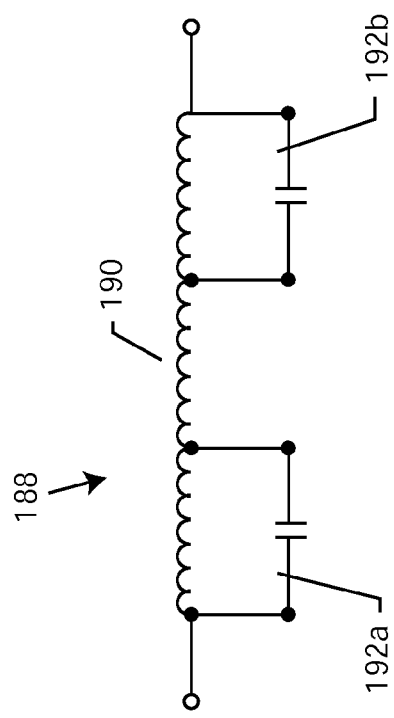
FIG. 77 is an electrical schematic of the structure shown in FIGS. 74 and 76.

FIG. 77 illustrates the schematic diagram of the composite RF current attenuator 188 previously described in FIGS. 74 and 76.

Figure 78:
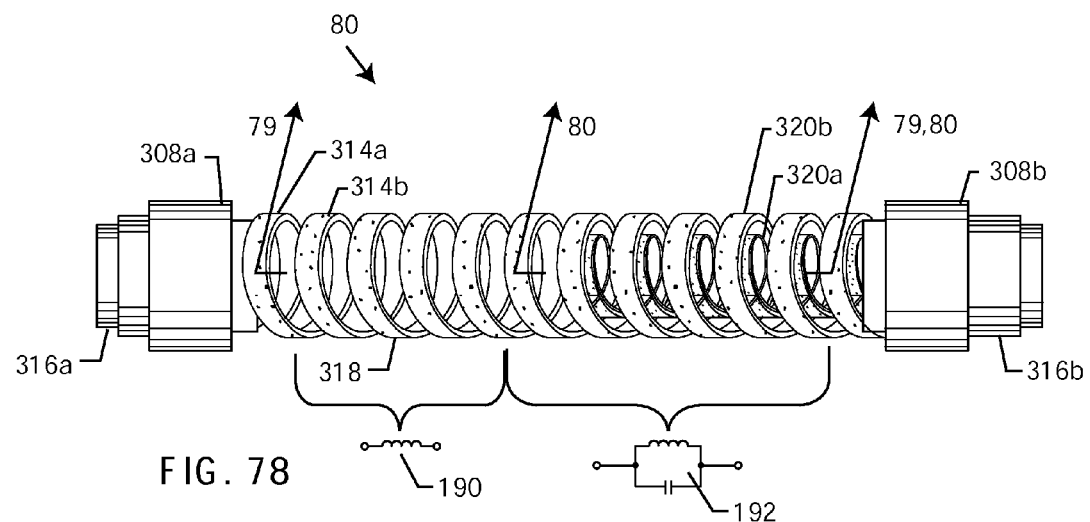
FIG. 78 is an elevational view of an inductive lowpass filter-multilayer helical parasitic capacitance bandstop filter having end caps for convenient mechanical and electrical connection into an implantable lead conductor.

FIG. 78 illustrates an inductor 190 in series with a multihelical wave filter 192 with end caps 308*a* and 308*b* for convenient mechanical and electrical connection in series into one or more conductors of an implantable lead 162 of an AIMD 110. For example, an implantable lead 162 may be comprised of material MP35N. The lead conductor would be easily laser welded to contact 316*a* of end cap 308*a*. The inductor 190 and multilayer helical wave filter 192 are disposed in series between these two end caps 308*a* and 308*b*. End cap 308*b* is connected (not shown) to a distal electrode 164 in contact with body tissues. The composite RF current attenuator 188 of the present invention can be disposed anywhere along the length of an implanted lead 162. However, in a particularly preferred embodiment, it is disposed at or near the distal electrode 164. An electrode assembly (not shown) may be electrically and mechanically connected to end cap 308*b*.

Referring once again to FIG. 78, the inductor portion 190 is spaced apart as shown to have minimum parasitic capacitance between adjacent coils 314*a* and 314*b*. This forms an inductor in series with the multihelical wave filter 192. The multihelical wave filter 192 is more thoroughly described in U.S. patent Ser. No. 13/193,495 entitled, MULTILAYER HELICAL WAVE FILTER FOR MRI APPLICATIONS, the contents of which are incorporated herein by reference. Along the length of an implanted lead, any combination of inductor portions 190 and multihelical wave filter portions 192 may be put in series in various combinations. The simplest embodiment is the inductor portion 190 in series with a single multilayer helical wave filter 192 as illustrated in FIG. 78.

Figure 79:
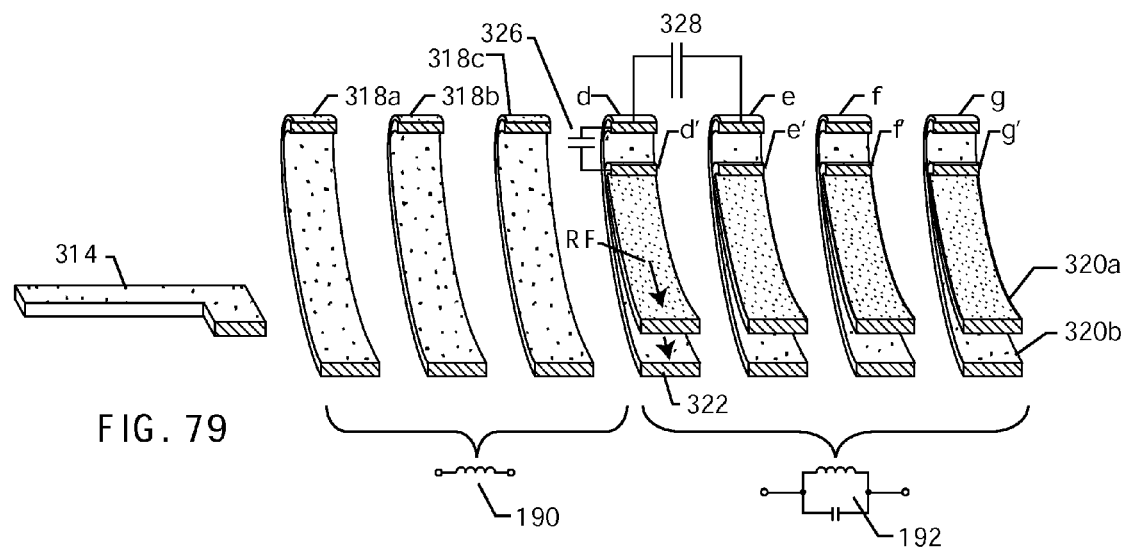
FIG. 79 is a sectional view taken generally along the line 79-79 from FIG. 78.

FIG. 79 is generally taken from section 79-79 from FIG. 78. On the left is the single layer helical portion 318*a*, 318*b*, 318*c* that forms the simple inductor portion 190. On the right side, one can see the inner 320*a* and outer 320*b* helices that form the multihelical wave filter 192.

Figure 80:
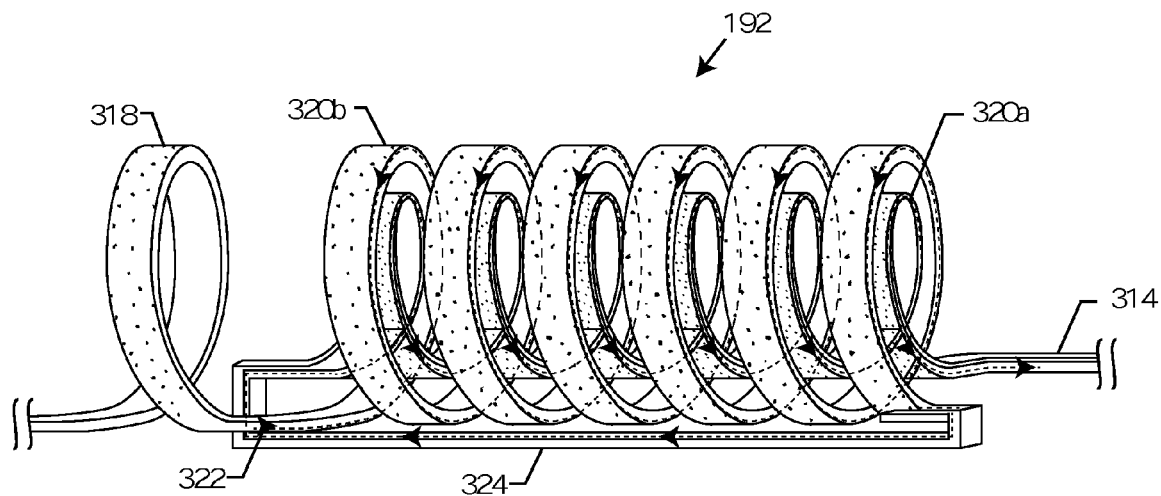
FIG. 80 is a partially schematic view of the structure shown in FIGS. 78 and 79, wherein the first helically wound segment of the bandstop filter is much larger in diameter than the second helically wound segment for illustrative purposes.

FIG. 80 is generally taken from section 80-80 from FIG. 78 and shows the multilayer helical wave filter 192.

FIG. 80 is an isometric view of the multilayer helical wave filter 192 of FIG. 78 which is in series with an inductor 190 in an implanted lead 162. Not shown is an overall insulation covering the multilayer helical wave filter 192 which is contiguous with the implanted lead 162 to provide isolation of the multilayer helical wave filter 192 from body fluids. This insulation is omitted for clarity purposes in many of the drawings, however, it will be understood that this insulation is essential so that the impedance of the multilayer helical wave filter 192 at resonance is not degraded by parallel RF current paths through body tissues or fluids. Shown is an elongated rectangular conductor 314 with an MRI RF induced current 322 shown entering it. The elongated conductor 314 forms a first helically wound inductor segment 318. This segment 318 is attached to a second helically wound inductor segment 320*b* and in the second segment 192. There is also a return wire connecting segment 324 (which could be coiled) which is used to wind a second helically wound inductor 320*a* inside of the second segment 192. Accordingly, the two helically wound inductor segments 320*a* and 320*b* of the second portion 192 are wound in the same longitudinal direction and share a common longitudinal axis where planar surfaces of the outer helically wound segment 320*b* face or abut planar surfaces of the inner helically wound inductor segment 320*a*. In general, this forms an inductor portion 198 in series with a parasitic capacitance-bandstop filter portion 200 of the present invention. The elongated conductor 314 has a dielectric insulation 302 which is also used to insulate the entire composite RF current attenuator 188 such that RF currents through body fluids do not degrade its impedance at resonance. A capacitance 326 is formed between the planar surfaces in the second section 192 of the outer helically wound inductor segment 320*b* and the inner helically wound inductor segment 320*a*. There is also a capacitance 328 formed between adjacent turns of this bandstop filter section 192. The effect of these inductor segments and capacitances will be to form a helical wave filter which behaves electrically like a bandstop filter 192. There are a number of advantages to the multilayer helical-inductor-helical bandstop wave filter construction as illustrated in FIG. 78. First of all, by using biocompatible materials, there is no need for discrete components placed inside of a hermetic seal. One is referred to US 2010/0231237 for a description of how discrete passive capacitors and inductors are placed inside a hermetically sealed housing to form a bandstop filter. This package is both large and very expensive to produce. It will be apparent that the multilayer helical wave filter 192 of the present invention is both volumetrically efficient and relatively much lower in cost.

FIG. 79 is very similar to FIG. 78 except that this shows the side view and the helically wound segments are exploded and separated so one can see the internal construction. For the first inductor portion 190, there is not an inner coil. However, in the bandstop filter portion 192, there is an outer helically wound inductor segment 320*b* and an inner helically wound inductor segment 320*a*, which are connected by the return wire. The direction of RF current flow 322 is also indicated. As one can see, in the inductor portion in both the first (outer) helical wound inductor segment 320*b* and the second (inner) helically wound inductor segment 320*a*, the RF induced current flow 322 from MRI is always in the same direction. Having the current flow be in the same direction of the various inductor segments of the present invention is critically important. Having the RF current flow in the same direction increases the inductance by up to a factor of four times as compared to having a single inductor winding. Current flow in the same direction results in much stronger effective fields as opposed to field reduction in the case of opposite current flows in adjacent turns.

As shown in FIG. 80, the design of the return wire or segment 324, which can be straight, curvilinear or coiled, (and also be either external or internal to the inductor segments) is a key. In the prior art, which teaches parasitic inductance to form simple bandstop filters, the current flow of adjacent coils is generally in opposite directions. In the present invention, the fields associated with the return wire or segments 324 are negligible in comparison with the fields generated by both the inner 320a and outer 320b multilayer helical inductor segments. Referring once again to FIG. 80, one could also vary the pitch between adjacent turns of portions of the multilayer helical wound wave filter 192. This would create sections that had a different resonant frequency as compared to other sections. Accordingly, it is a feature of the present invention that the multilayer helical wave filter 192 can be resonant at 1, 2 or even "n" number of selected RF frequencies. Similar effects can be achieved by carefully controlling the overlap area between the planar surfaces of the outer inductor segment 320b and the inner inductor segment 320a. This would affect the amount of parasitic capacitance and hence the resonant frequency. It is also possible to control this parasitic capacitance by controlling the dielectric thickness or the dielectric type in various sections of the multilayer helical wave filter 192 of the present invention. By controlling the dielectric type, the dielectric constant can be varied anywhere from two to fifty. Most polymer-type dielectric coatings 302 have a dielectric constant that fall between two and four. However, there are certain other types of dielectrics such as tantalum oxide, which would provide significantly higher dielectric constants (closer to 40). Different materials with different dielectric constants can be used in different sections of the multilayer helical wave filter.

The return wire or segment 324 may be directed through the inside (not shown) of both the outer helically wound inductor segment 320b and the inner helically wound inductor segment 320a of the multilayer helical wave filter portion 192. FIG. 80 shows the return wire or segment 324 returns outside of both the first helically wound inductor segment 320b and the second helically wound inductor segment 320a. This return wire or connecting segment 324 is a straight elongated conductor. It is also be possible to coil this conductor 324 to increase mechanical flexibility of the filtered region. It is advised that the number of coils in this return path 324 be limited to the minimum number of turns needed. This is to ensure that the eddy currents created by this return path 324 (reverse currents) will be minimal and should not greatly impact the overall inductance of the first and second helical wound segments 320a, 320b. Typically, the coiled return path is disposed at an angle to the first and second helically wound segments 320a, 320b. This is to reduce the effect of eddy currents due to reverse currents in the return path [ideally close to 90 degrees is better but it could be anywhere greater than 0 degrees except (n*pi) n being 0, 1, 2, etc.]. This coiled return path is also useful in increasing or controlling the phase shift between the RF induced currents in the first helically wound inductor segment 320b relative to the currents in the second helically wound inductor segment 320a.

Figure 81:
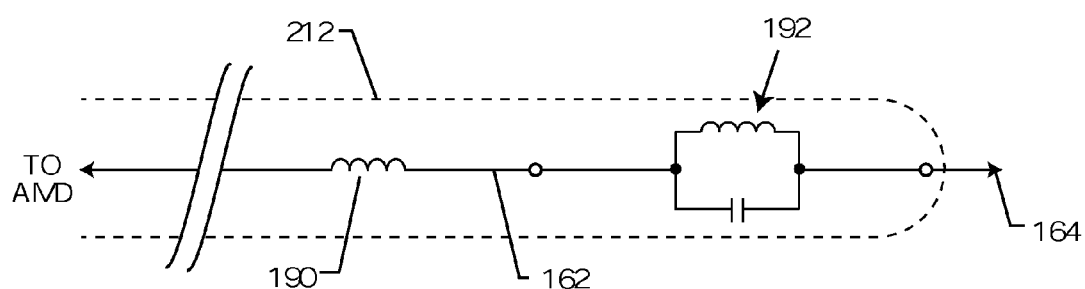
FIG. 81 is an electrical schematic diagram of the multilayer helical wave filter of FIGS. 78-80.

FIG. 81 is a schematic diagram of a lead, probe or catheter showing an inductor portion 190 in series with a bandstop filter portion 192. Also shown is an overall lead body insulation 212 which is integral to the lead 162 and also covers both the inductor 190 and the bandstop filter 192. This insulation 212 is very important to prevent RF electrical leakage through body fluids in parallel with the composite RF current attenuator 188 of the present invention. Such RF leakage currents can significantly degrade the impedance of the composite RF current attenuator 188 at its one or more resonant frequencies. The amount of RF current leakage can be so severe that the composite RF current attenuator 188 becomes ineffective in preventing a distal electrode 164 from overheating during an MRI scan.

Figure 82:
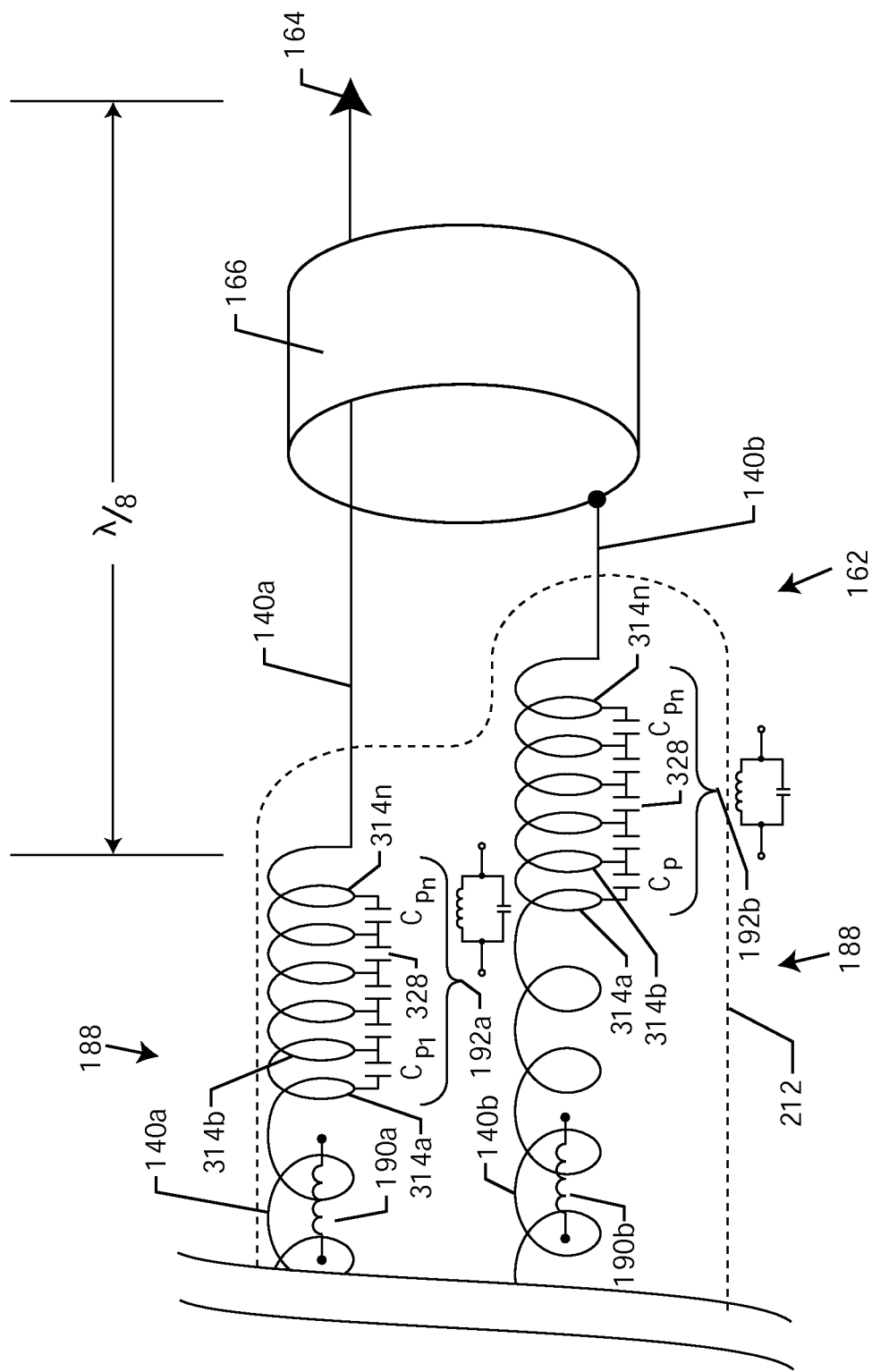
FIG. 82 is similar to FIGS. 31 and 72, but illustrates series inductors and bandstop filters formed by lead inductance and parasitic capacitance, disposed within an insulative sheath.

FIG. 82 is a schematic illustration of a bipolar pacemaker lead 162 with a tip 164 and ring 166 electrode. The tip electrode conductor 140a and the ring electrode conductor 140b both have a series inductor 190a, 190b and bandstop filter 192a, 192b in accordance with the present invention. The implantable lead conductors 140a and 140b can either be coiled as shown or straight (filer) or the like. By way of background, the individual conductors of prior art implanted leads are usually not individually insulated. In the prior art, the lead body does have an overall insulation covering 212. In prior art uninsulated adjacent lead conductors, the coils tend to short out in many places, particularly when the lead is going around sharp, torturous bends in a venous system. In accordance with the present invention and as shown in FIG. 82, there are two series lowpass 190 and bandstop 192 broadband filter sections in series with the implanted lead conductors 140a and 140b that is coiled, wherein the inductive conductors 190 do have an insulative coating 302 with a specific dielectric constant material coated over them. These inductive coils 314 in the BSF filters 192a and 192b are generally closely spaced (with a predetermined spacing) such that a distributed capacitance 328 is formed between the adjacent coils/windings 314a, 314b, etc. of the inductor. Along the length of both bandstop filters 192a and 192b, an inductance (inductor) is formed along with the parallel parasitic (or stray) capacitance 328 from turn to turn in order to form the bandstop filters 192 of the present invention.

As used further herein, the terms "parasitic capacitance" and/or "stray capacitance" and/or "distributed capacitance" are synonymous and refer to the capacitance formed between the adjacent turns of an inductive coil 314a, 314b, etc. In addition, as used herein, the terms "parasitic capacitance" and/or "stray capacitance" and/or "distributed capacitance" can also refer to the total capacitance formed in the inductor coil which is the sum of all of the individual turn to turn capacitances. Electrically, in FIG. 82, the total capacitance $C = C_{p1} + C_{p2} + \ldots C_{pn}$ appears in parallel with the total inductance L of the inductive coil to form the parallel resonant bandstop filters 192a and 192b.

In a preferred embodiment, these inductive coil-parasitic capacitance self-broadband filters 192a and 192b are located at, near or within the distal electrodes 164 of the implantable lead 162. In the case of FIG. 82, these are the bipolar Tip and/or Ring electrodes 164 and 166 of a typical cardiac pacemaker 110C. Each bandstop filter 192a and 192b is a single inductive coil component with enough total parasitic capacitance to be self-resonant at the MRI RF pulsed frequency or frequency range. Accordingly, FIG. 82 is also the equivalent circuit schematic of FIG. 81. The capacitance C, as illustrated in FIG. 82, is the sum of the parasitic capacitances $C_{P1}$ through $C_{pn}$. In this case, "n" indicates that any number of inductor coil turns, as desired, can be created for the inductive coil portion of the leads of 140a and 140b. The self-resonant inductor bandstop filter portions 192a, 192b of the implanted leads 140a and 140b can be formed at the same time the overall lead 140a, 140b conductor is formed, or they may be prefabricated (coiled) and then installed in one or more locations along the lead by laser welding attachment or the like. In an embodiment, the dielectric insulation 302 that coats the coils of the inductive-parasitic capacitance bandstop filter portions 192a, 192b may also coat the entire lead 140a, 140b conductor coils (this would facilitate easy fabrication in some cases). Referring once again to FIG. 82, the inductor 190a, 190b and bandstop filter 192a, 192b composite RF current attenuator 188 ideally should be at, near or within both the distal tip 164 and the distal ring 166 electrode. This is not always possible and in some cases, it may be necessary to space the composite RF current attenuator 188 further away from the electrode. Electrically speaking, the composite RF current attenuator 188 should be spaced no greater than the wave length of the RF frequency divided by 8 ($\lambda/8$). If the composite RF current attenuator 188 is spaced further away from the distal electrode 164 than this, then it is possible that RF energy may be deposited from the MRI scanner on the wrong side of the filter, where it could induce dangerous currents or heating into a distal electrode 164. In no case should the spacing exceed $\lambda/4$.

Figure 83:
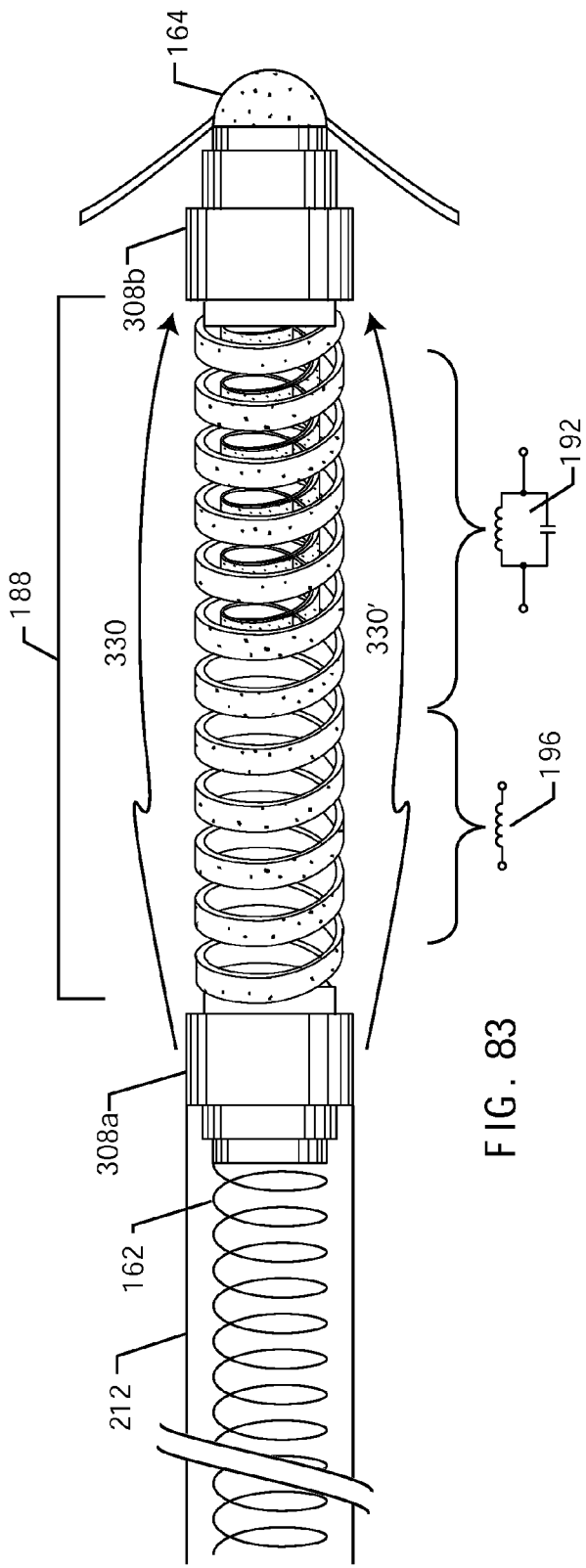
FIG. 83 is an elevational view of the composite RF current attenuator of FIG. 82 shown in series with a passive fixation electrode in an implanted cardiac lead.

FIG. 83 illustrates the composite RF current attenuator 188 with end caps 308a and 308b that were previously illustrated in FIG. 78. End cap 308b is shown attached to the conductor 162 of an implanted lead which has an overall insulation sheath 212. In this case, by way of example, the composite RF current attenuator 188 could present 2000 ohms at its primary resonant frequency of 64 MHz. However, in this configuration, since the composite RF current attenuator 188 does not have overall end to end insulation, there are undesirable RF leakage paths 330 and 330' through body tissue (actually, a very large number of leakage paths). The 2000 ohms of impedance desirably impedes the flow of MRI induced RF currents into body tissue through the electrode 164. However, if both ends of the composite RF current attenuator 188 are not isolated from each other, parallel paths 330 and 330' result through body fluid (ionic fluid). This parallel leakage path effect as measured by the inventors can be approximately 80 ohms. Referring back to FIG. 83, if an 80 ohm parallel path existed between the end caps 308a and 308b, this would seriously degrade the impedance at resonance. The amount of degradation in impedance can result in RF currents flowing through the distal electrode 164 into body tissues that could result in life-threatening overheating of these adjacent tissues.

Figure 84:
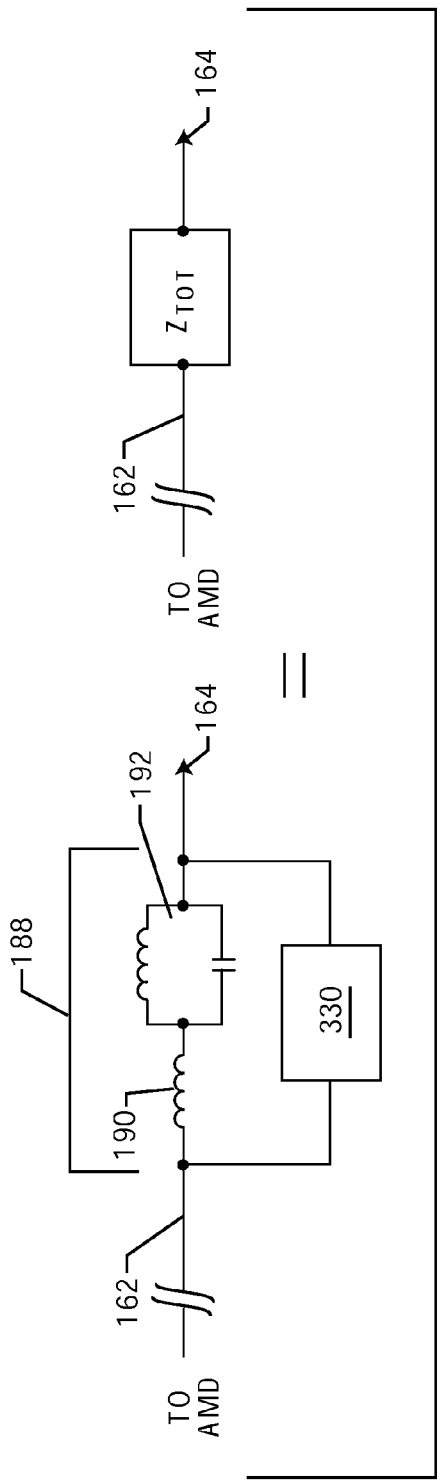
FIG. 84 is a schematic diagram which illustrates undesirable electrical leakage through body fluids in parallel with the composite RF current attenuator of FIG. 83.

FIG. 84 is the schematic diagram taken from FIG. 83 showing the 2000-ohm impedance $Z_F$ at the primary resonance of the composite RF current attenuator 188. Shown in parallel with the composite RF current attenuator 188 is the RF leakage path 330 or 80-ohm impedance of the body tissues. Using the parallel resistance formula, when one has 80 ohms in parallel with 2000 ohms, the result is a combined impedance $Z_{TOT}$ of 76.82 ohms. As one can see, this is a catastrophic reduction of the impedance of the composite RF current attenuator 188 at resonance. It is a feature of the present invention that these body fluid paths 330 and 330' be insulated and/or blocked such that they cannot cause significant leakage in parallel with any of the elements of the composite RF current attenuator 188 of the present invention.

Figure 85:
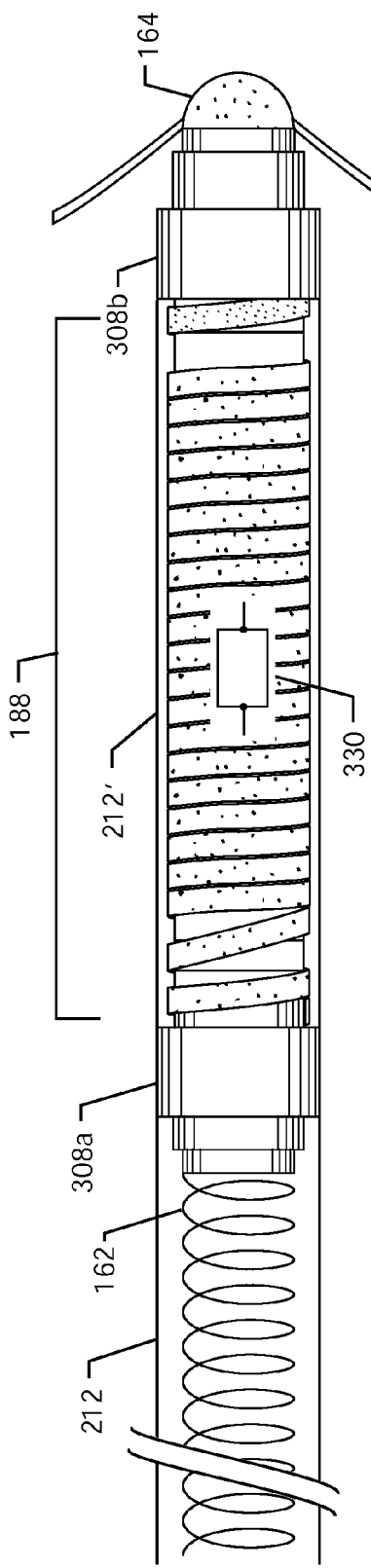
FIG. 85 is an elevational view of the composite RF current attenuator of FIG. 84 with electrical insulation such that electrical leakage through body fluids is inhibited or prevented.

FIG. 85 is very similar to FIG. 83 except that the lead insulation 212' has been extended completely over the composite RF current attenuator 188 of the present invention. Accordingly, the leakage paths 330 through body fluid or tissues have been eliminated. In this case, the composite RF current attenuator 188 of FIG. 85 would present nearly the full 2000 ohms of impedance at the MRI RF-pulsed frequency. It should be noted that no insulation material is perfect. In other words, the insulation material 212' would still allow for a very slight amount of leakage. However, the intention here is that the amount of leakage resistance in ohms would be negligible (very high) compared to the overall bandstop filter impedance at resonance. The insulating coating may, in addition to what is proposed, provide an environment conducive to parasitic capacitance with (i) external fluids, (ii) external structures in the lead construction or (iii) to "nano" (colloids) metal or metal like materials suspended in the insulating coating.

Figure 86:
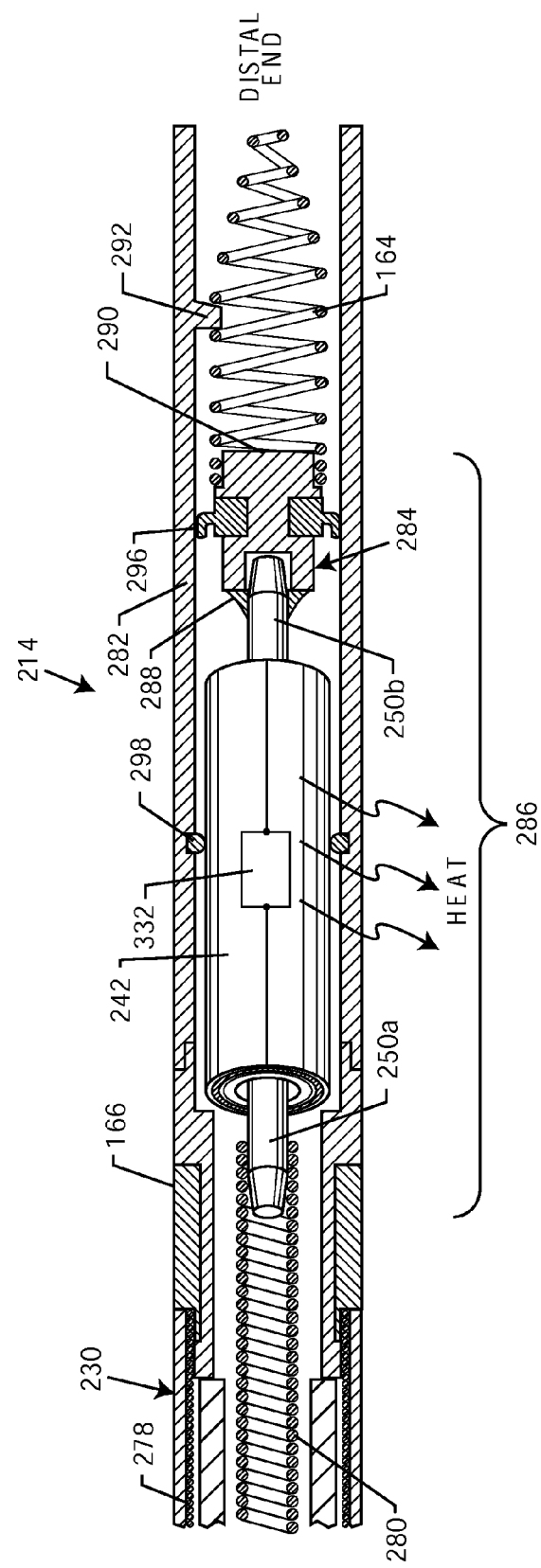
FIG. 86 is a sectional view of an active fixation electrode assembly embodying an inductive coil-parasitic capacitance bandstop filter with seals to preventingress of body fluids.

FIG. 86 is a translatable active fixation electrode assembly that was previously described in connection with FIG. 65. Shown is a box 332 which indicates that any of the circuits of the present invention can be disposed within the hermetically sealed casing 242.

Figure 87:
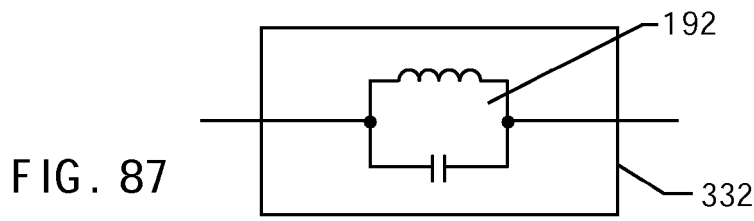
FIG. 87 illustrates that the box 332 shown in FIGS. 85 and 86 may be a bandstop filter.
Figure 88:
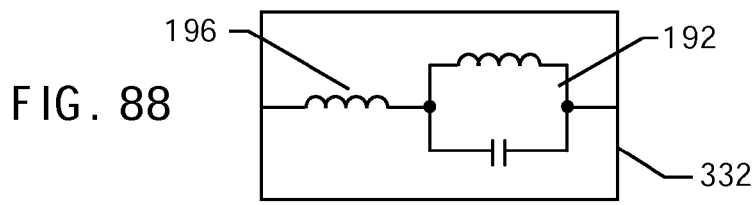
FIG. 88 illustrates that the box 332 could be an inductor lowpass filter in series with a bandstop filter in accordance with the present invention.
Figure 89:
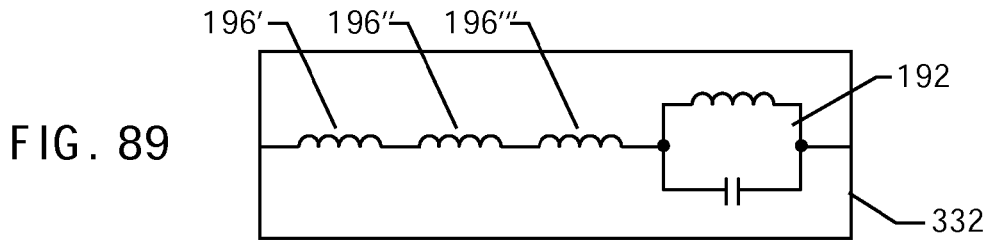
FIG. 89 illustrates that the box 332 could be a number of inductors in series with a bandstop filter in accordance with the present invention.
Figure 90:
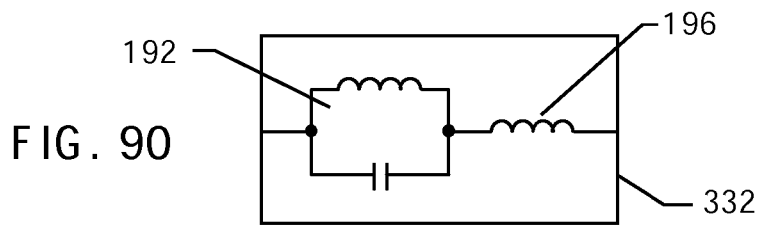
FIG. 90 illustrates that the inductor can be on either side of the bandstop filter.
Figure 91:
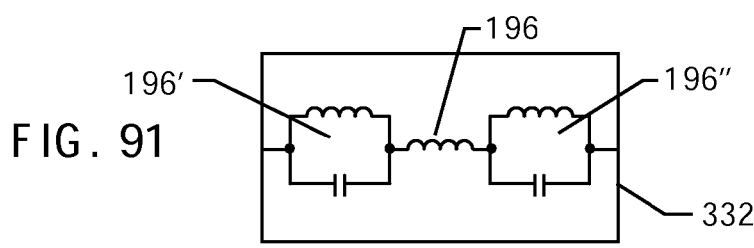
FIG. 91 illustrates that box 332 may consist of a bandstop filter in series with a lowpass filter inductor in series with a bandstop filter.
Figure 92:
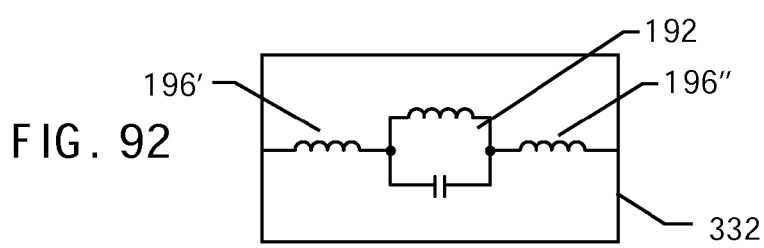
FIG. 92 illustrates that the box 332 illustrated may also consist of a broadband lowpass filter inductor in series with a bandstop filter and in turn in series with another lowpass filter inductor.
Figure 93:
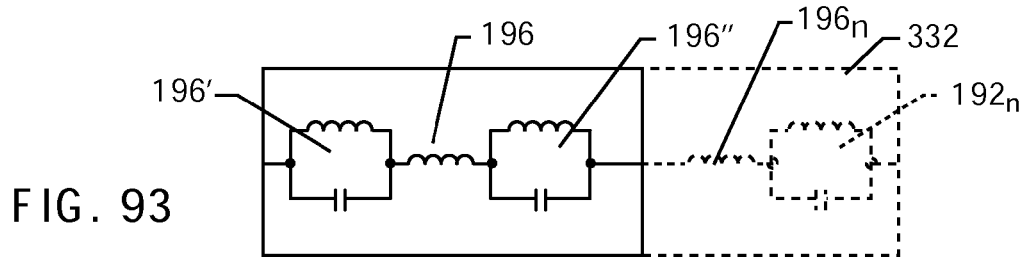
FIG. 93 illustrates that the box 332 may consist of any number of bandstop filters and series inductances placed in a lead conductor.

FIGS. 87-93 illustrate various electrical circuits 332 which could be placed within the translatable casing 242. FIG. 87 illustrates a bandstop filter 192. FIG. 88 illustrates a single element lowpass filter inductor 196 in series with a bandstop filter 192. Any of the lowpass filters shown in FIG. 45 can be used to replace any of the inductors 196 in drawings FIGS. 87-93. FIG. 89 illustrates that the inductor element 196 can consist of a number of inductors disposed along the length of a lead conductor 196' through 196'''. FIG. 90 illustrates that the configuration illustrated in FIG. 88 can be reversed. FIG. 91 illustrates that a bandstop filter 196' can be connected in series with a single element lowpass filter (or any of the lowpass filters of FIG. 45) in series 196 with a second bandstop filter 196". FIG. 92 illustrates that conductor 196' can be placed in series with a bandstop filter 192 and then in turn in series with a second conductor 196". Of course these inductors may be broken up and distributed along the length of the entire lead on both sides of bandstop filter 192. FIG. 93 illustrates that any number of bandstop filters 196 can be placed in series with any number of lowpass filters (in this case a single element lowpass filter inductor 196) in any order along the length of a lead conductor.

Figure 94:
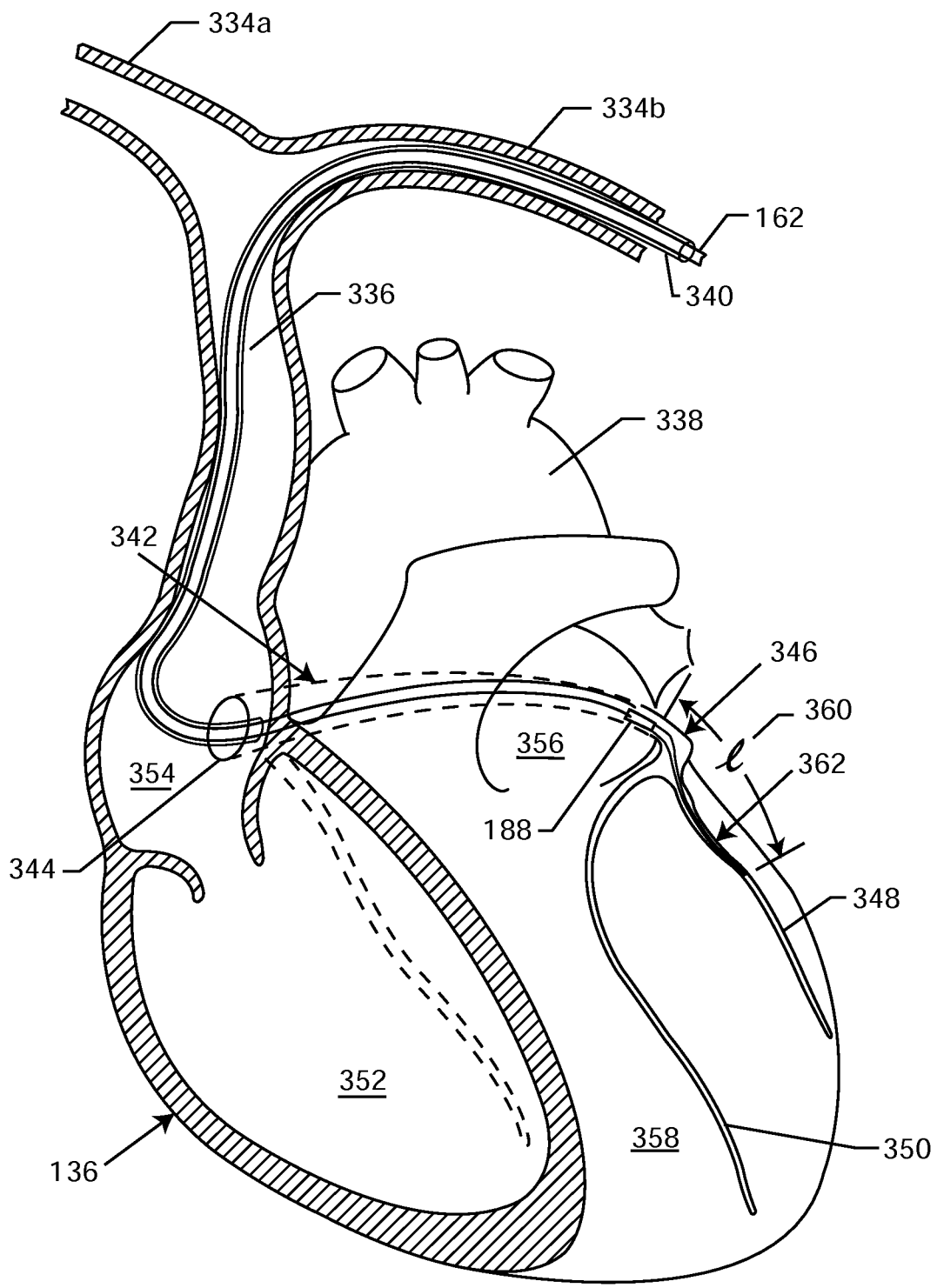
FIG. 94 is a diagrammatic representation of the human heart showing a left ventricular endocardial lead system embodying the present invention.

FIG. 94 is a diagrammatic representation of a human heart 136 which includes right and left subclavian veins 334a and 334b respectively, the superior vena cava 336 and the aorta 338. A lead 162, which is typically routed from a CRT-D or CRT-P device (not shown), is routed through a catheter 340 and directed, in this case, through the left subclavian vein 334b and then down through the superior vena cava 336 and into the coronary sinus 342. The lead 162 must first enter the coronary sinus ostium 344 where the implanting physician selects the correct location. The coronary sinus 342 is actually divided into two zones: the first part (on the left) is known as the coronary sinus 342; and the second part (on the right) is called the great cardiac vein 346. The great cardiac vein 346 wraps around the back of the left ventricle. The composite RF current attenuator 188 is intended to be placed ideally near the end of the great cardiac vein 346 where it breaks into several venous branches. These branches are called the posterior branch, the lateral branch 348 and the anterior branch 350. A more comprehensive name, for example, would be the interventricular branch.

Again referring to FIG. 94, one can also see the right ventricle 352 and the right atrium 354. Also shown are the left atrium 356 and the left ventricle 358. The ideal location for a composite RF current attenuator 188 is shown. An ideal length for the lead extension 360 of the composite RF current attenuator 188 would be between 5 and 7.5 mm in length. At this particular location, at the end of the great cardiac vein 346, cardiac motion is relatively small and fibrotic tissue will tend to encapsulate the composite RF current attenuator 188 and its associated lead 162 and thereby attach it/fixate it in position in this relatively low motion region. This is particularly advantageous in that the lead 162 will remain highly reliable and resistant to breakage. Because of the relatively large diameter of the coronary sinus 342 and the great cardiac vein 346, this portion of the lead system, including the composite RF current attenuator 188, can be of much larger diameter (for example, 7 or 8 French). Beyond this point, where the great cardiac vein 36 branches, the venous systems become much smaller. In general, these branches are below 6 French in diameter and ideal electrode sizes go all the way down to 3 French. Referring once again to FIG. 94, one can see that the furthest back the composite RF current attenuator 188 should be from the distal electrode is shown as length 360. As previously mentioned, this should ideally be no more than an RF wave length divided by 8 ($\lambda/8$) but in no case greater than $\lambda/4$. By keeping the distance to the filter $<\lambda/8$, one ensures that MRI RF fields will not couple on the wrong side (the distal side) of the composite RF current attenuator 188. As used herein, wave length refers to the wave length of the MRI pulsed RF field in body tissue.

FIG. 95 shows the relationship between French size, millimeters and inches. Since left ventricular pacing is important for cardiac resynchronization and treatment of congestive heart failure, it is a feature of the present invention that a lead body diameter/size reduction occurs at the distal end of the composite RF current attenuator 188 allowing insertion of the smaller diameter/size lead extension 362 with distal electrodes into the small diameter venous system in the proper position outside the left ventricle 358.

The primary benefit of locating the composite RF current attenuator 188 in the coronary sinus 342 and/or great cardiac vein 346 is that the diameter of the composite RF current attenuator 188 itself can be larger making it much easier to manufacture. The distal portion 362 of the lead 162 from the composite RF current attenuator 188 is smaller (3 to 6 French size) for easier employment and navigation into the branch veins of the left ventricle 358. Secondary benefits beyond the diameter of the composite RF current attenuator 188 include the length of the composite RF current attenuator 188. Entering into and navigating the coronary sinus 342 and great cardiac vein 346 generally involve larger bend radii compared to accessing and navigating the branch vessels. Therefore the lead extension 362 that traverses through and resides in the branch vessels must be very small and very flexible, not having a stiff section longer than approximately 1.5 mm as a rule of thumb. Rigid sections of the lead 162 measuring longer than 1.5 mm can impede the ability to navigate around the tight corners and bends of the branch vessels. In the coronary sinus 342 and great cardiac vein 346, however, there is substantially more latitude, and stiff sections of the lead could approach 5 mm or even 7.5 mm without drastically impeding deliverability.

A secondary benefit of locating the composite RF current attenuator 188 in the coronary sinus 342 or the great cardiac vein 346 has to do with MRI image artifacts. Although the image artifact will be quite small due to avoiding the use of ferromagnetic materials, it is still beneficial to locate the composite RF current attenuator 188 away from the coronary arteries, ventricular wall motion or other anatomies/physiologies/pathologies of most interest. If a composite RF current attenuator 188 is located in the coronary sinus 342, however, it could generate small artifact in the vicinity of the valves. Another benefit of having the composite RF current attenuator 188 located in the coronary sinus 342 or the great cardiac vein 346 is that its rigidness provides a foundation on which optional fixation fixtures may be more strategically utilized. For example, one or more tines could originate from the region of the lead where the composite RF current attenuator 188 resides. Additionally, rigidness of the filter 188 makes the tines more effective in their engagement of the vessel walls. Alternatively, a rigid portion of the lead 162, skillfully navigated beyond a corner or bifurcation, can function as a fixation mechanism that proves difficult or requires skill to track the lead.

The portion of an implanted lead which is distal of a composite RF current attenuator 188 is known as the lead extension 362. In general, this lead extension 362 at its proximal end will be connected to the composite RF current attenuator 188 and its distal end will terminate in electrodes in contact with body cells or tissue. For the purposes herein, it is important that the electrical wave length ($\lambda$) of the lead extension 362 not be physically too long. This has to do with its efficiency as an antenna and picking up energy from the RF pulsed fields of an MRI system. In general, for 1.5 Tesla systems, lead lengths that couple very efficiently are in the 42 to 60 cm range. In a preferred embodiment, the length ($\lambda$) of any lead extension, whether it be for a cardiac application, a deep brain application or the like, should be less than $\frac{1}{8}$ of an electrical wavelength ($\frac{1}{8}\lambda$). It has been shown that leads that are less than $\frac{1}{8}$ of electrical wavelength of the MRI RF frequency do not act as effective antennas and therefore pick up an insignificant amount of energy from the external MRI RF pulse field. In some cases, the electrical length of the lead extension could be as long as $\frac{1}{4}$ or even $\frac{1}{4}\lambda$. In these cases, variables include the lead trajectory, the sensitivity of the tissues that are in contact with a distal electrode, patient characteristics and the like. For example, myocardial tissue is much less subject to thermal damage than is deep brain tissue.

FIG. 96 is an enlarged perspective view of the lead system 162 taken from FIG. 94. One can see that there is a guide wire 364 which is common in the prior art for inserting into position prior to sliding the highly flexible lead system 162 down over it. A terminal pin 366 is designed to plug into an implantable medical device, such as a pacemaker or ICD. The composite RF current attenuator 188 is shown at the point where the lead 162 would be reduced from 6-9 French down to the 3-6 French lead extension 362. Optional fixation tines 368 are shown which may be affixed, disposed, or adjacent to the composite RF current attenuator 188. By way of reference, the French scale is related to both diameter in millimeters (mm) or inches. For example, 7 French is 2.3 mm (0.092 inch) in diameter and 3 French is only 1 mm in diameter (0.039 inch). The electrical length ($\lambda$) of the reduced diameter lead extension 362 can be adjusted in accordance with the branch vein into which the lead system is being inserted in the desired location of the electrodes 370.

Below the electrodes 370 is the other end of the guide wire 364. Once the electrodes 370 are in the proper position and the system has been tested, the guide wire 364 is then removed. A particular advantage of the lead system 162 as shown in FIG. 96 is that no new deployment instruments or catheters are required. In other words, this system that includes the composite RF current attenuator 188 is backwards compatible with most known deployment systems. It is also very important that the lead system 162 is designed to be extracted in the case of a broken lead, defective lead or infected lead. The lead system illustrated in FIGS. 96 and 97, is also backwards compatible with current mechanical and laser lead extraction technologies.

Referring to FIG. 97, one can see that there is an inductor 196, 196' plus bandstop filter 192, 192' associated with each of the lead conductors and distal electrodes 370 and 370'. These composite RF current attenuators 188 are placed in series with each one of the electrode lead conductors 140a, 140b as shown. One can see that there is an inductor 172 disposed distal to the bandstop filters 192. This is best understood by referring to the schematic diagram in FIG. 98 which shows an inductor 196 in series with the bandstop filter 192 in series with a second inductor 172.

Figure 99:
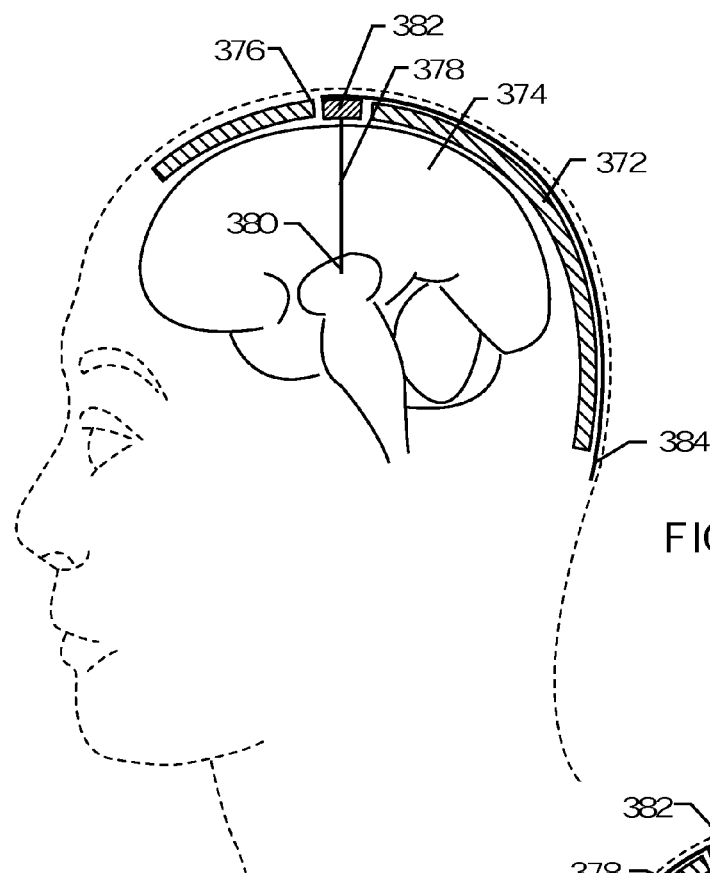
FIG. 99 is a diagrammatic, side cross-sectional view of the human head showing the placement of a deep brain probe and electrode embodying the composite RF current attenuator of the present invention.

FIG. 99 is a diagrammatic side cross-sectional view of the human head showing the skull 372 and the brain 374. A burr hole 376 is drilled through the skull 372 for placement of deep brain probe 378 with associated electrodes 380. The deep brain probe 378 is equivalent to a lead extension in that the composite RF current attenuators 188 are placed within burr hole container 382. This allows for the deep brain probe 378 and its associated electrodes 380 to be very small in diameter which is equivalent to the lead extension 362 previously discussed in FIG. 94. One can see that there is a lead 384 which has been tunneled up underneath the skin and attaches to the deep brain probe 378. The distal end of the lead 384 is generally connected to an AIMD (not shown) such as a pulse generator. The AIMD may be located somewhere in the patient's skull or tunneled through the neck and located in a pectoral implant region. One or more composite RF current attenuators 188 are located inside of the skull burr hole 376 in housing 382. The composite RF current attenuator housing 382 may be located within the burr hole 376, above the burr hole 376, or even in the dura mater or subdural region.

Figure 100:
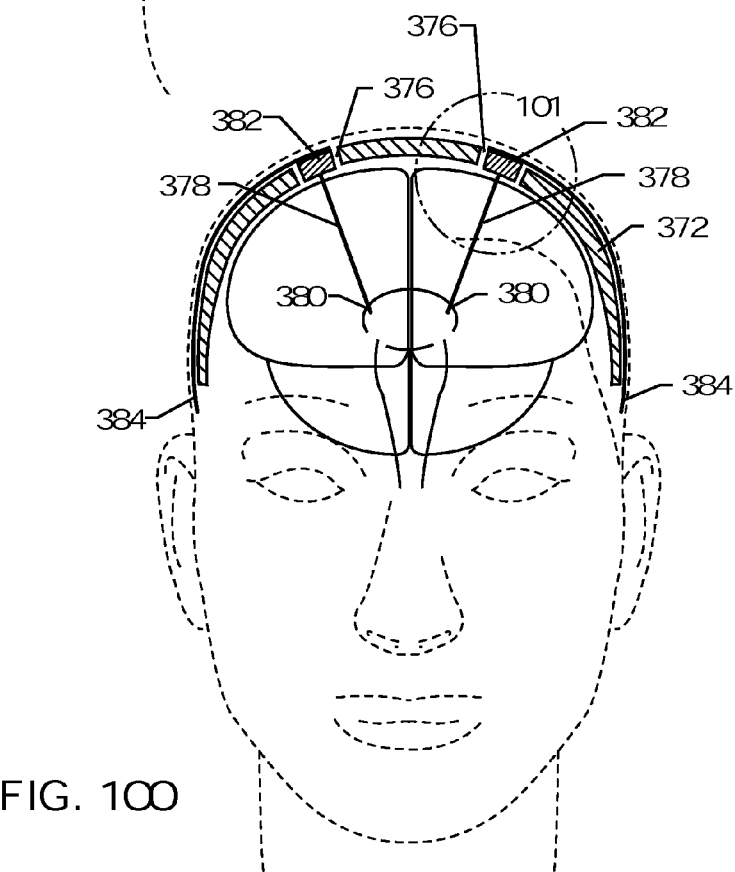
FIG. 100 is a diagrammatic, front cross-sectional view of the human head showing use of multiple deep brain probes.

FIG. 100 is a diagrammatic cross-sectional front view of the human head, showing that there can be multiple deep brain probes 378 . . . 378$_n$ placed as previously described in connection with FIG. 99. In a preferred embodiment, the top of the deep brain probe 378 and associated composite RF current attenuator containers 382, 382' would be flush with the top of the skull 372. The lead 384 is generally connected to a pulse generator or transmitter which is either implanted or can sit outside the skin. There can also be a receiver which sits on the skin. The deep brain probe 378 can also have a nail head or nail shank.

Figure 101:
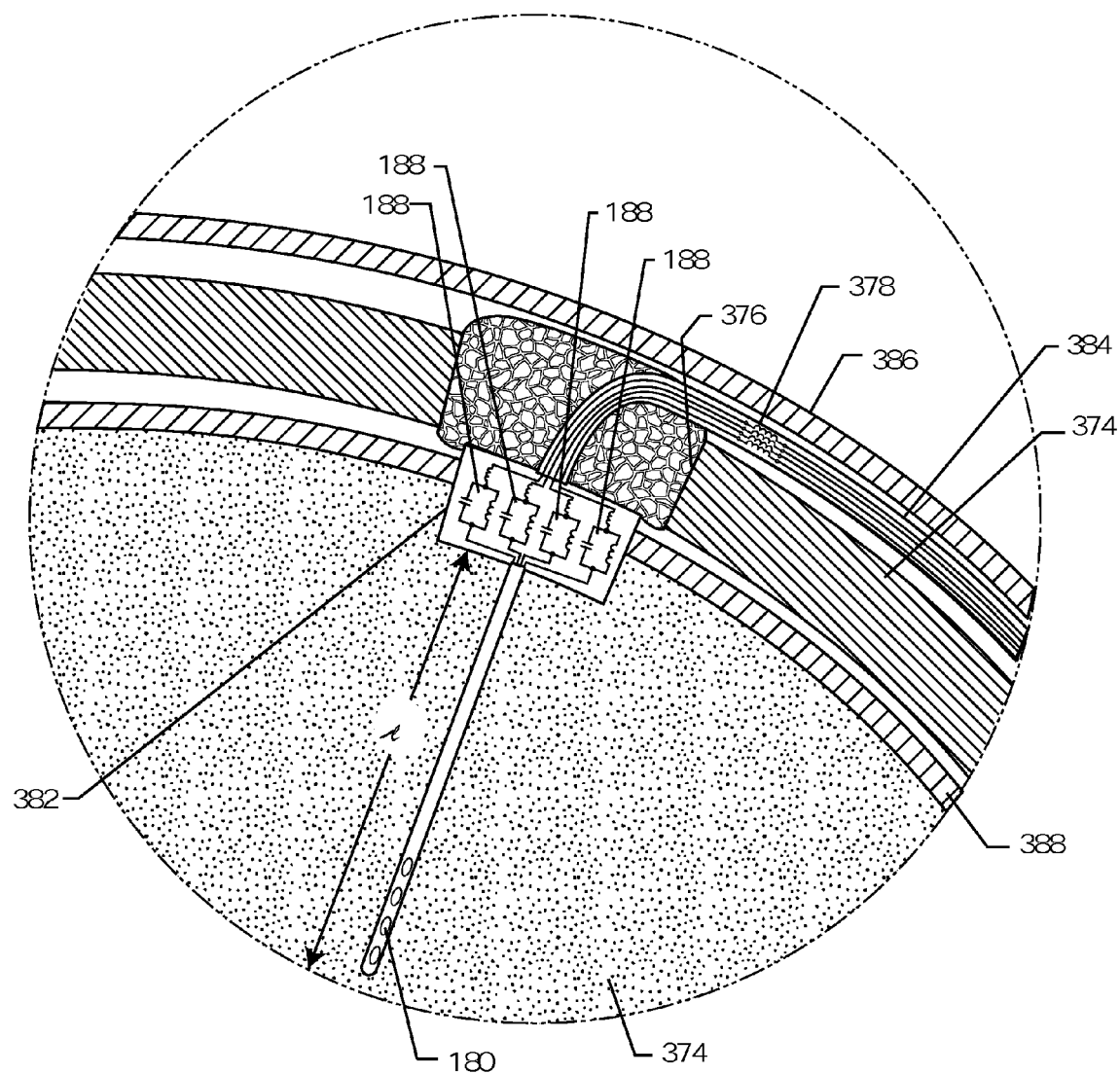
FIG. 101 is an enlarged sectional view taken generally of the area indicated by the line 101 in FIG. 100.

FIG. 101 is an enlarged sectional view of the area indicated by line 101 in FIG. 100, of the deep brain probe 378. Shown are the locations of the composite RF current attenuators 188, 188' 188", and 188''' in the housing 382, the skin 386 which covers the skull 374, the lead 384, the burr hole 376, dura mater 388 and the brain 374. At the end of the deep brain probe 378 are electrodes 180. The inductors can be incorporated into the same housing 382 as the bandstop filter of the composite RF current attenuators 188 or may be distributed along the length of the leads as shown in location 378. An optional location for the inductors is along the length of the leads 384 tunneled under the skin 386 (outside the skull 372).

Figure 102:
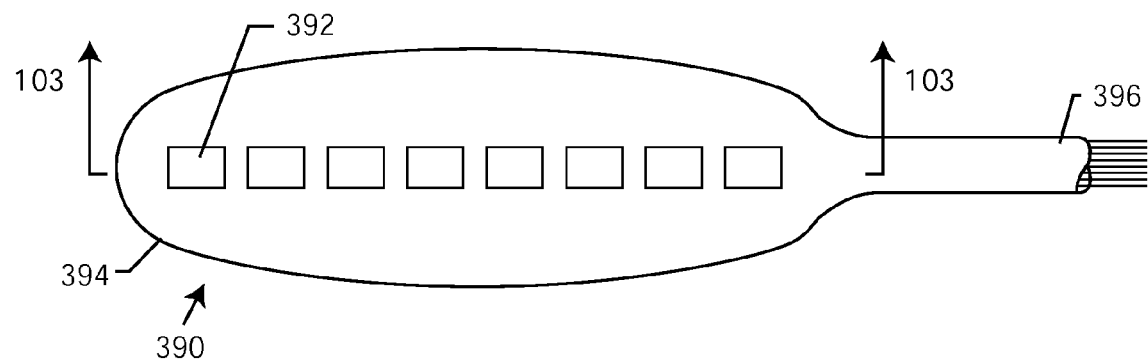
FIG. 102 is a fragmented top plan view of an exemplary paddle or PAD electrode embodying the present invention.

FIG. 102 illustrates a paddle or PAD electrode array 390 which could be used, for example, in spinal cord simulator applications. It has eight electrodes 392 housed in a biocompatible insulative and flexible body 394. An eight conductor lead 396 (there can be any number) is connected respectively to each of the eight electrodes 392. As previously discussed, the elongated lead 396 can pick up significant amounts of RF energy during MRI scanning. It is very important that the electrodes 392 do not overheat since they are in direct contact with body tissue, for example, with the spinal cord.

Figure 103:
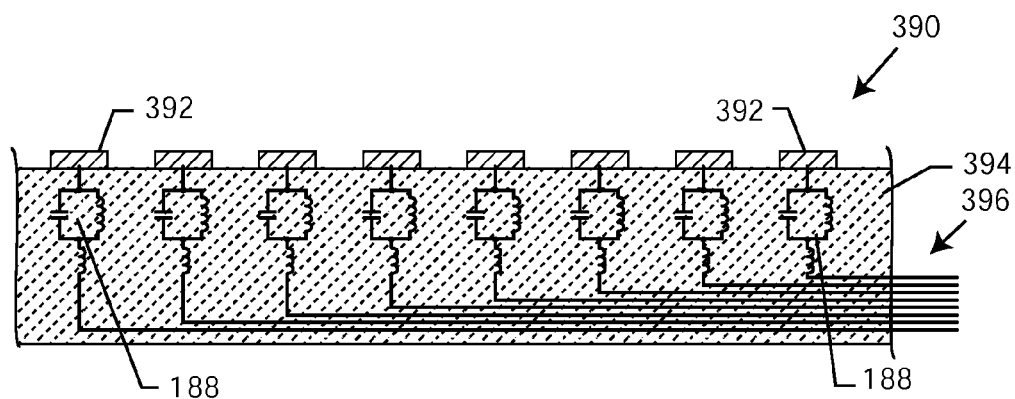
FIG. 103 is an enlarged sectional view taken generally along the line 103 in FIG. 102.

FIG. 103 is a sectional view taken of section 103-103 from FIG. 102. Shown are the eight electrode PADs 392 each of which is connected in series with a composite RF current attenuator 188 of the present invention. Accordingly, there are eight electrode PADs 392 in contact with body tissue, there are eight composite RF current attenuators 188 and eight conductors that make up the lead bundle 396. Referring once again to FIG. 103, if it were necessary to save space, the composite RF current attenuators 188 could be placed at a point proximal from the electrode PAD array 390. The electrodes 392 would then be located at the distal end of a lead extension in accordance with the present invention.

Figure 104:
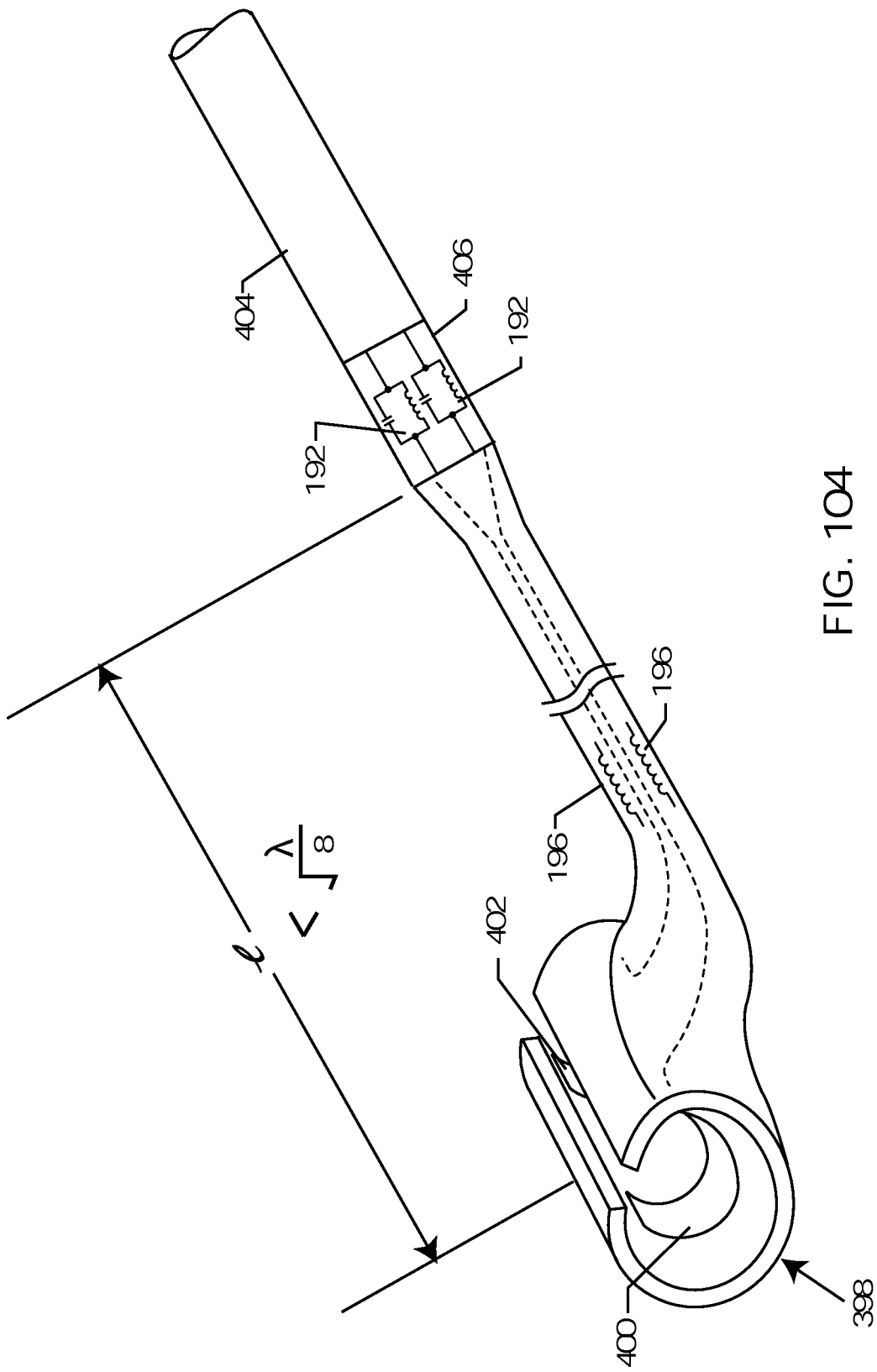
FIG. 104 illustrates a split cylinder cuff electrode designed to wrap around a nerve.

FIG. 104 illustrates a split cylinder cuff electrode 398 embodying two electrodes (Anode 400 and Cathode 402). This is designed to be inserted by a physician around a nerve. It is a bipolar system typically consisting of a 6-8 French diameter lead body 404. A double bandstop filter 406 (two discrete bandstop filters 192 in parallel) each in series with an inductor 196 in accordance with the present invention is located as shown to form a dual composite RF current attenuator 188. In general, the cuff 398 is sized to match the diameter of the nerve which passes through its center. The lead body 404, after the double bandstop filter 406, is of a reduced diameter, generally in the 3-4 French range. Not shown is a closing suture which is typically used to draw the cuff together after it's installed.

Figure 105:
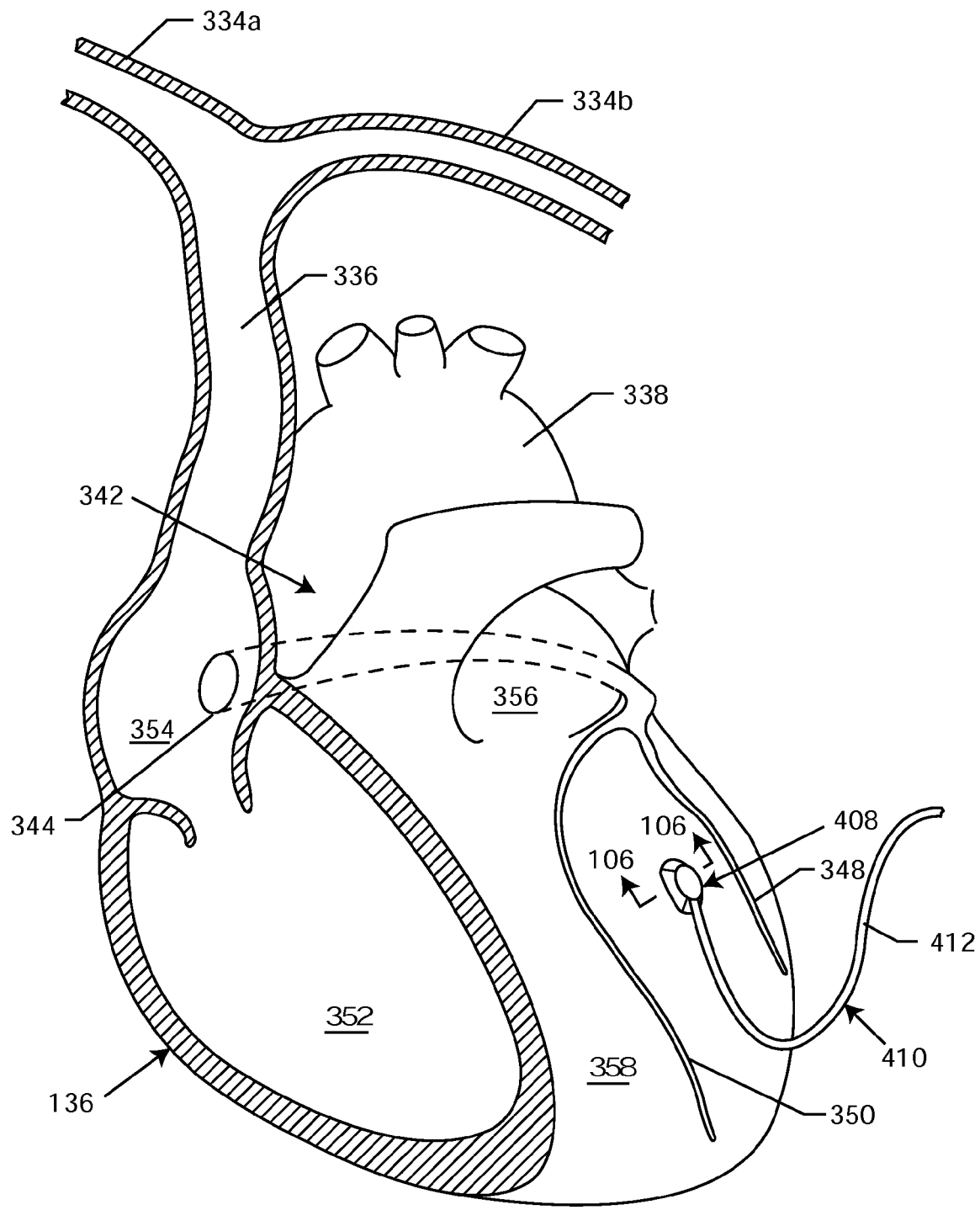
FIG. 105 is a diagrammatic representation of the human heart, showing epicardial lead attachment to the outside of the left ventricle.

FIG. 105 is a diagrammatic representation of the human heart 136 similar to that illustrated in FIG. 94. However, in this case, external (epicardial) electrodes 408 are attached outside and to the left ventricle 358 by means of epicardial leads 410. A sutureless myocardial lead 410, 412 is shown affixed to the outside of the left ventricle. This methodology is well known and generally involves an insertion between the ribs outside of the heart and a screwdriver type feature to affix the sutureless epicardial lead tip electrode 408 in place. Epicardial leads may also have a suture feature which can have a helical or other configuration type tip. It should be apparent that the present invention can be extended to any type of external (epicardial) electrode 408 or satellite pacer affixed to the outside of the heart, particularly outside of the left ventricle.

Figure 106:
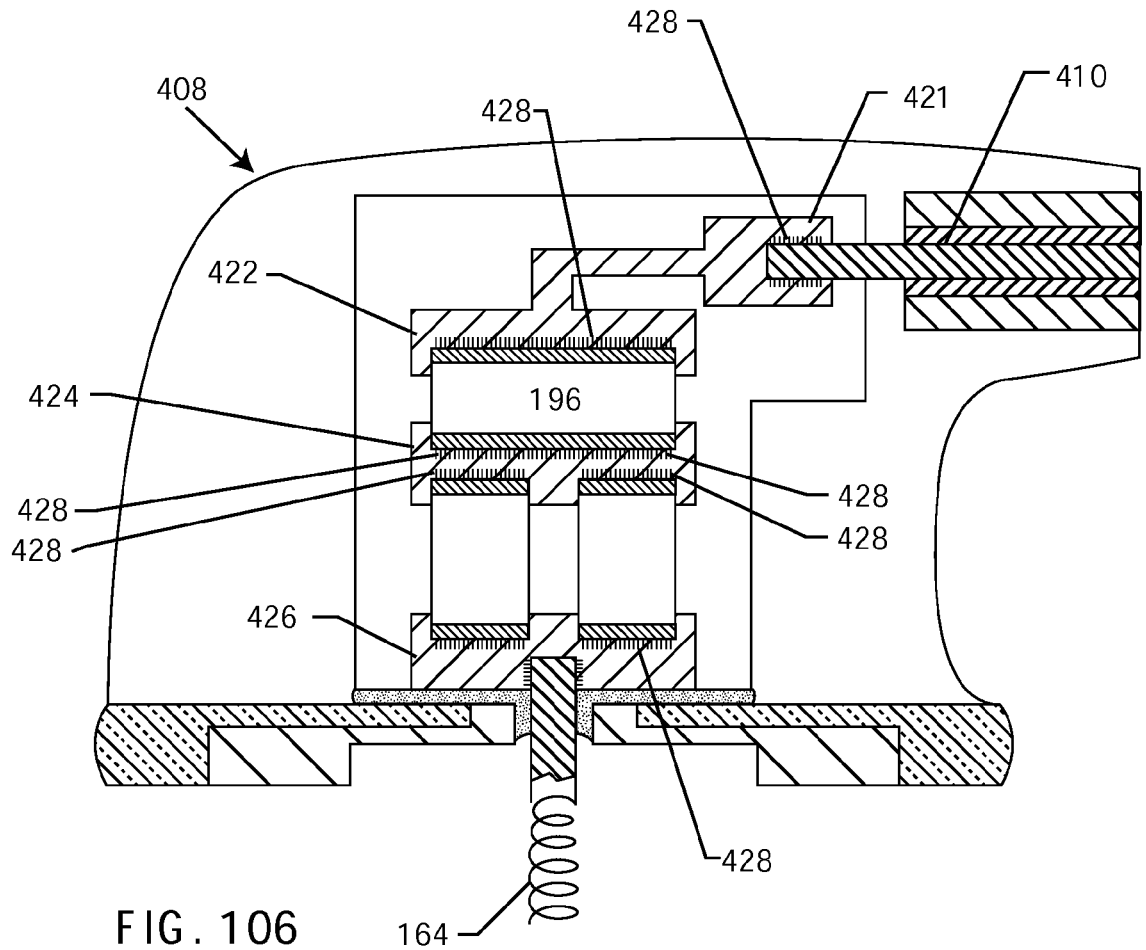
FIG. 106 is taken from section 106-106 in FIG. 105 showing the present invention disposed within an epicardial electrode.

FIG. 106 is a sectional view of the epicardial electrode 408 taken generally from section 106-106 from FIG. 105. As shown, there is a composite RF current attenuator 188 of the present invention consisting of inductor 196 in series with bandstop filter 192 (which consists of inductor 198 in parallel with capacitor 200). The lead conductor 410 enters the housing of the epicardial electrode 408 and is connected to an end on a circuit trace 421. The circuit trace connects to a second end 422 where the inductor chip 196 is electrically attached either with a solder or a thermal-setting conductive adhesive 428. The other end of inductor 196 is connected to a second circuit trace end 424. Both of the inductor 198 and the capacitor 200 bandstop filter elements are connected to this circuit trace 424. The other end of the inductor 198 and capacitor 200 are connected to circuit trace land 426 which has the effect of putting the capacitor in parallel with the inductor forming thereby a bandstop filter 192.

Figure 107:
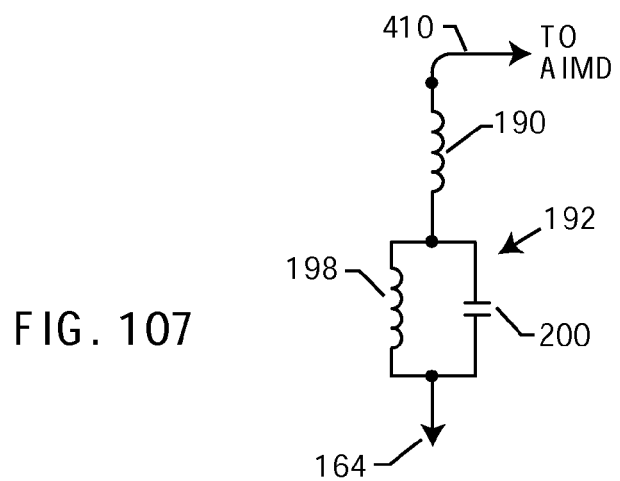
FIG. 107 is the electrical schematic diagram of the structure illustrated in FIG. 106.

FIG. 107 is the schematic diagram of the structure shown in FIG. 106, showing a lowpass filter element 190 (inductor 196) in series with the bandstop filter 192. The bandstop filter is connected to the epicardial electrode 164 as shown.

Figure 108:
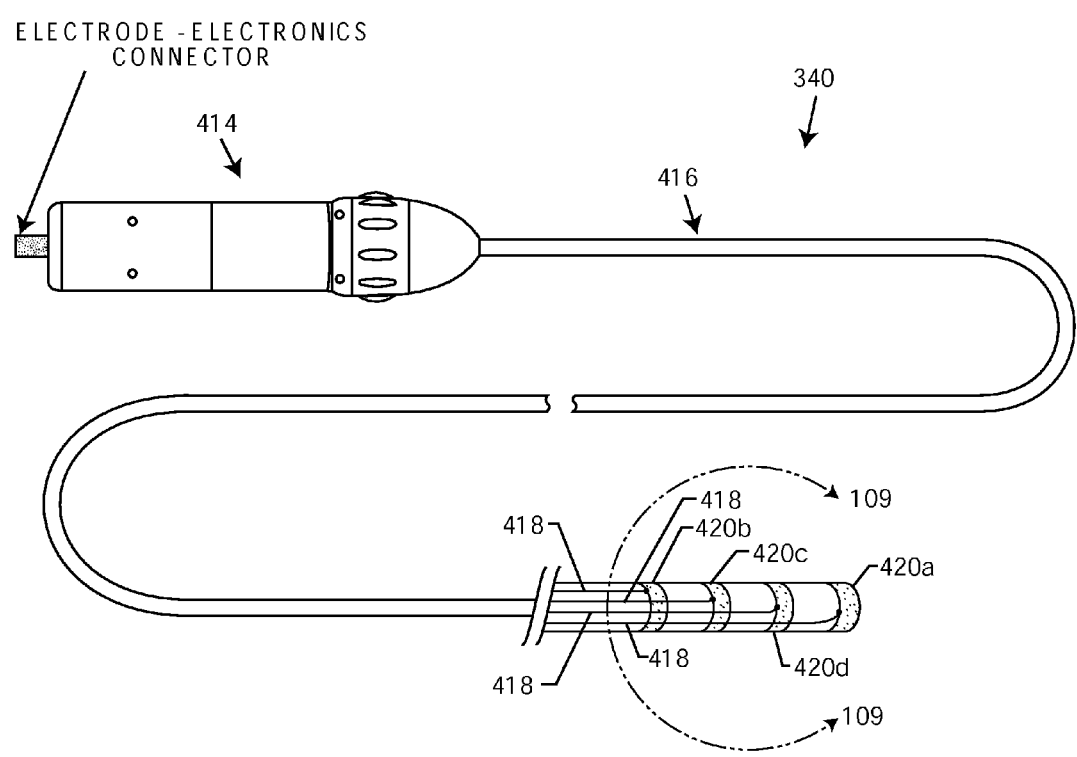
FIG. 108 is a schematic diagram of a prior art probe or catheter showing ablation and sense electrodes.

FIG. 108 is a schematic diagram of a typical probe or catheter 340. Typically, the probe or catheter 340 has a handle or pistol grip 414 connected to a steerable elongated body 416 which includes leadwires 418$a$-418$d$. In general, by adjusting the handle 414, the body 416 can be curved through torturous transvenous lead paths. In this case, there are four electrodes shown including ablation electrode 420$a$, as well as, sense electrodes 420$b$-420$d$.

Figure 109:
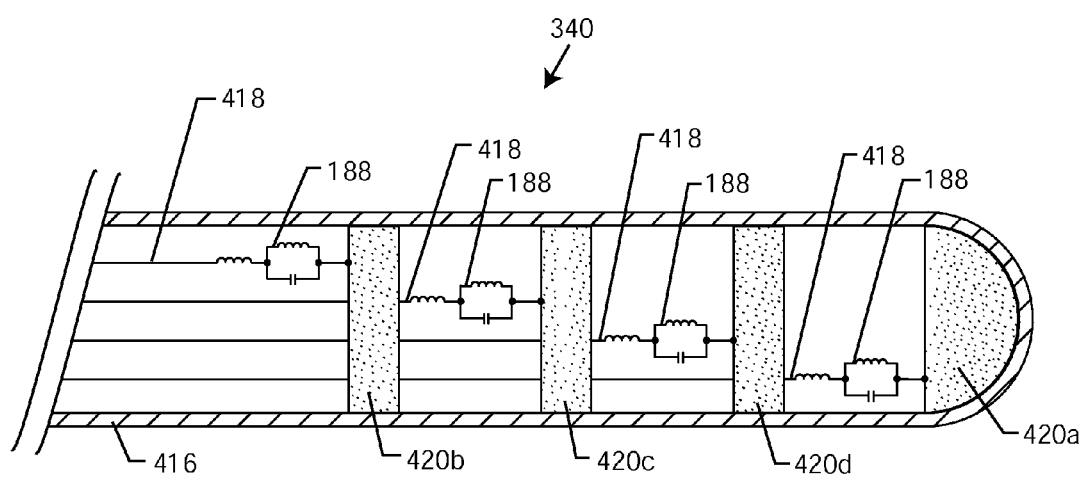
FIG. 109 is taken generally of the area designated by line 109-109 from FIG. 108, and illustrates composite RF current attenuators placed in series with each of the electrodes.

FIG. 109 is taken generally of the area designated by line 109-109 from FIG. 108, and illustrates that there is a composite RF current attenuator 188$a$-188$d$ of the present invention in series with each one of the conductors 418$a$-418$d$. As previously described, these composite RF current attenuators 188$a$-188$d$ present a high impedance at the MRI RF pulsed frequency and thereby prevent inadvertent overheating of the distal electrodes 420$a$-420$d$. The ablation electrode 420$a$ delivers RF ablation energy only when it's located in a precise location. For example, this precise location could be related to scar tissue formation around atrial pulmonary vein(s) to eliminate atrial fibrillation. Inadvertent electrode heating (from the MRI RF field) is highly undesirable in that scar tissue would occur in unwanted locations. For example, if the sinus node is accidently ablated, the patient would then be pacemaker dependent for the rest of their life.

From the foregoing it will be appreciated that the present invention is directed to a medical lead comprising a conductor having a distal electrode contactable to biological cells, and a composite RF current attenuator 188. The composite RF current attenuator includes a bandstop filter comprising at least a portion of the lead conductor, for attenuating RF current flow through the lead conductor at a selected center frequency or across a range of frequencies, wherein the bandstop filter comprises a capacitance in parallel with a first inductance, said parallel capacitance and inductance placed in series with the lead inductor, wherein values of capacitance and inductance are selected such that the bandstop filter attenuates RF current flow at the selected center frequency or across the range of frequencies. The composite RF current attenuator further comprises a lowpass filter in series with the bandstop filter and comprises of at least a portion of the lead conductor. A lowpass filter, in one embodiment, may comprise a second inductance in series with the bandstop filter and form at least a portion of the lead conductor. More broadly, the lowpass may comprise an L filter, a T filter, a Pi filter, an LL filter, or an "n" element filter in series with the bandstop filter and form at least a portion of the lead conductor.

Although several embodiments of the invention have been described in detail for purposes of illustration, various modifications of each may be made without departing from the spirit and scope of the invention. Accordingly, the invention is not to be limited, except as by the appended claims.

What is claimed is:

1. An implantable device, comprising:
   a) at least one lead conductor having a length extending from a proximal conductor end to a distal conductor portion having a distal conductor end, wherein the proximal conductor end is electrically connectable to an active implantable medical device;
   b) at least one electrode electrically connected to the distal conductor portion or the distal conductor end, wherein the electrode is contactable with biological cells; and
   c) at least one self-resonant inductor comprising at least a portion of the lead conductor formed as a coiled inductor;
   d) a first dielectric material coating the lead conductor forming the self-resonant inductor having a parasitic capacitance between adjacent turns of the coiled inductor to thereby provide an equivalent circuit comprising a first inductance in parallel with a capacitance so that the self-resonant inductor has a resonant impedance centered at an MRI RF pulse frequency or across a range of frequencies about the center frequency;
   e) at least one second non-resonant inductance of at least 100 nanohenries electrically connected in series with the self-resonant inductor along the length of the lead conductor, wherein the second inductance is non-resonant at or near the MRI RF pulsed frequency; and
   f) a second dielectric material coating the second inductance;
   g) wherein at least the first dielectric material adhesively attaches together adjacent coils comprising the self-resonant inductor so that a resulting resonant impedance remains stable.

2. The implantable device of claim 1, wherein an inductance resistance and a capacitance resistance of the self-resonant inductor provide an overall Q so that the resultant 3-dB bandwidth is at least 100 kHz.

3. The implantable device of claim 1, wherein an inductance resistance and a capacitance resistance of the self-resonant inductor provide an overall Q so that the resultant 3-dB bandwidth is at least 0.5 MHz.

4. The implantable device of claim 1, wherein the at least one second inductance comprises a plurality of second inductances provided at spaced locations along the at least one lead conductor.

5. The implantable device of claim 1, wherein the at least one second inductance is equal to or greater than 300 nanohenries.

6. An implantable device, comprising:
   a) at least one lead conductor having a length extending from a proximal conductor end to a distal conductor portion having a distal conductor end, wherein the proximal conductor end is electrically connectable to an active implantable medical device;
   b) at least one electrode electrically connected to the distal, conductor portion or the distal conductor end, wherein the electrode is contactable with biological cells; and
   c) at least one self-resonant inductor comprising at least a portion of the lead conductor formed as a coiled inductor;
   d) a first dielectric material coating the lead conductor forming the self-resonant inductor, wherein the self-resonant inductor has a parasitic capacitance between adjacent turns of the coiled inductor to thereby provide an equivalent circuit comprising a first inductance in parallel with a capacitance so that the self-resonant inductor has a resonant impedance of at least 500 ohms centered at an MRI RF pulse frequency or across a range of frequencies about the center frequency; and
   e) at least one low pass filter connected in series along the length of the lead conductor, wherein the low pass filter comprises at least one inductor is series with the conductor and wherein the at least one inductor has a second inductance of at least 100 nanohenries,
   f) wherein at least the first dielectric material adhesively attaches together adjacent coils comprising the self-resonant inductor so that the resonant impedance remains stable.

7. The implantable device of claim 6, wherein the at least one low pass filter is selected from the group consisting of a single element inductor, an L filter, a T filter, a Pi filter, an LL filter, and an "n" element filter.

8. The implantable device of claim 6, wherein the at least one inductor of the low pass filter is selected from the group consisting of a discrete passive inductor, an inductor chip, an inductor winding, an inductor meander, a spiral inductor, and an inductor trace.

9. The implantable device of claim 6, wherein an inductance resistance and a capacitance resistance of the at least one self-resonant inductor provide an overall Q so that the resultant 3-dB bandwidth is at least 100 kHz.

10. The implantable device of claim 6, wherein an inductance resistance and a capacitance resistance of the at least one self-resonant inductor provide an overall Q so that the resultant 3-dB bandwidth is at least 0.5 MHz.

11. An implantable lead comprising a lead length extending axially from a proximal lead end to a distal lead portion having a distal lead end, wherein the proximal lead end is configured to be permanently or removably connectable to electronic circuits of an active implantable medical device, the implantable lead comprising
- a) at least a first electrode contactable with biological cells, wherein the first electrode is disposed axially along the lead length at or near the distal lead end;
- b) at least a first conductor extending from an electrical connection at the first electrode to or adjacent to the proximal lead end;
- c) at least a second electrode contactable with biological cells, wherein the second electrode is disposed axially along the lead length at or near the distal lead portion and axially proximal the first electrode;
- at least a second conductor electrically insulated from the first conductor and extending from an electrical connection at the second electrode to or adjacent to the proximal lead end;
- e) a first self-resonant inductor comprising at least portion of the first conductor formed as a first coiled inductor;
- f) a first dielectric material coating the lead conductor forming the first self-resonant inductor, wherein the first self-resonant inductor has a first parasitic capacitance between adjacent turns of the first coiled inductor to thereby provide an equivalent circuit comprising a first inductance in parallel with a first capacitance so that the first self-resonant inductor has a first resonant impedance of at least 500 ohms centered at an MRI RF pulsed frequency or across a range of frequencies about the center frequency, and wherein the first self-resonant inductor is disposed axially along the lead length between the first and second electrodes;
- g) a second self-resonant inductor comprising at least a portion of the second conductor formed as a second coiled inductor;
- h) a second dielectric material coating the lead conductor forming the second self-resonant inductor, wherein the second self-resonant inductor has a second parasitic capacitance between adjacent turns of the second coiled inductor to thereby provide an equivalent circuit comprising a second inductance in parallel with a second capacitance so that the second self-resonant inductor has a second resonant impedance of at least 500 ohms centered at an MRI RF pulse frequency or across a range of frequencies about the center equency, and wherein the second self-resonant inductor is disposed axially along the lead length between the second electrode and the proximal end of the implantable lead;
- i) a third inductance of at least 100 nanohenries electrically coupled in series along the first conductor and disposed axially along the lead length between the first and second electrodes;
- j) a third dielectric material coating the second inductance;
- k) a fourth inductance of at least 100 nanohenries electrically coupled in series along the second conductor and disposed axially along the lead length between the second electrode and the proximal end of the implantable lead;
- l) a fourth dielectric material coating the fourth inductance,
- m) wherein at least the first and second dielectric materials adhesively attach together adjacent coils forming the first and second self-resonant inductors so that the first and second resonant impedances remain stable.

12. The implantable lead of claim 11, wherein the third and fourth inductances are non-resonant at or near the MRI RF pulsed frequency.

13. The implantable lead of claim 11, wherein the first and second self-resonant inductors each comprise an overall circuit Q, wherein a resultant 3-dB bandwidth comprises at least 100 kHz.

14. The implantable lead of claim 11, wherein the first and second self-resonant inductors each comprise an overall circuit Q, wherein a resultant 3-dB bandwidth comprises at least 0.5 MHz.

15. The implantable lead of claim 11, wherein the first and second self-resonant inductors each comprise an overall circuit Q, wherein, a resultant 3-dB bandwidth comprises at least 10 MHz.

16. The implantable lead of claim 11, as a transvenous cardiac lead and the first electrode comprises an active fixation tip electrode.

17. The implantable lead of claim 16, as a transvenous cardiac lead and the second electrode comprises a ring electrode.

18. The implantable lead of claim 11, as a transvenous cardiac lead and the first electrode comprises a passive tip electrode including fixation tines.

19. The implantable lead of claim 18, wherein the second electrode comprises a ring electrode.

20. An implantable lead comprising a lead length extending axially from a proximal lead end to a distal lead portion having a distal lead end, wherein the proximal lead end is configured to be permanently or removably connectable to electronic circuits of an active implantable medical device, the implantable lead comprising:
- a) at least a first electrode contactable with biological cells, wherein the first electrode is disposed axially along the lead length at or near the distal lead end;
- b) at least a first conductor extending from an electrical connection at the first electrode to or adjacent to the proximal lead end;
- c) at least a second electrode contactable with biological cells, wherein the second electrode is disposed axially along the lead length at or near the distal lead portion and axially proximal the first electrode;
- d) at least a second conductor electrically insulated from the first conductor and extending from an electrical connection at the second electrode to or adjacent to the proximal lead end;
- e) a first self-resonant inductor comprising a portion of the first conductor formed as a first coiled inductor;
- f) a first dielectric material coating the lead conductor forming the first self-resonant inductor, wherein a first inductance is formed by the first coiled inductor, and wherein a first capacitance comprises a first parasitic capacitance between adjacent turns of the first coiled inductor so that the first self-resonant inductor has a first resonant impedance of at. least 500 ohms centered at an MRI RF pulse frequency or across a range of frequencies about the center frequency, and wherein the first self-resonant inductor is disposed axially along the lead length between the first and second electrodes;
- g) a second self-resonant inductor comprising a portion of the second conductor formed as a second coiled inductor;
- h) a second dielectric material coating the lead conductor forming the second self-resonant inductor, wherein a second inductance is formed by the second coiled inductor, and wherein a second capacitance comprises a second parasitic capacitance between adjacent turns of the second coiled inductor so that the second self-resonant inductor has a second resonant impedance of at least 500 ohms centered at an MRI RF pulse frequency or across a range of frequencies about the center frequency, wherein the second self-resonant inductor is disposed axially along the lead length between the second electrode and the proximal end of the implantable lead;
i) a third inductance of at least 100 nanohenries and which is non-resonant at or near the MRI RF pulsed frequency, wherein the third inductance is electrically coupled in series along the first conductor and disposed axially along the lead length between the first and second electrodes; and
j) a fourth inductance of at least 100 nanohenries and which is non-resonant at or near the MRI RF pulsed frequency, wherein the fourth inductance is electrically coupled in series along the second conductor and disposed axially along the lead length between the second electrode and the proximal end of the implantable lead,
k) wherein the first and second dielectric materials adhesively attach together adjacent coils forming the first and second self-resonant inductors so that the first and second resonant impedances remain stable.

21. The implantable lead of claim 20, wherein the first electrode comprises an active fixation tip electrode or a passive tip electrode including fixation tines.

22. The implantable lead of claim 20, wherein the second electrode comprises a ring electrode.

23. The lead of claim 20, wherein the first and second electrodes each comprise ring electrodes.

24. The implantable lead of claim 23, wherein the first and second self-resonant inductors have respective inductance resistances and capacitance resistances to provide an overall Q for each self-resonant inductor, wherein a resultant 3-dB bandwidth comprises at least 100 kHz.

25. The implantable lead of claim 24, wherein the resultant 3-dB bandwidth for each of the first and second self-resonant inductors is at least 0.5 MHz.

26. The implantable lead of claim 24, wherein the resultant 3-dB bandwidth for each of the first and second self-resonant inductors is at least 10 MHz.

27. An implantable lead comprising a lead length extending axially from a proximal lead end to a distal lead portion having a distal lead end, wherein the proximal lead end is configured to be permanently or removably connectable to electronic circuits of an active implantable medical device, the implantable lead comprising:
a) at least a first electrode contactable with biological cells, wherein the first electrode is disposed axially along the lead length at or near the distal lead end;
b) at least a first conductor extending from an electrical connection at the first electrode to or adjacent to the proximal lead end;
c) at least a second electrode contactable with biological cells, wherein the second electrode is disposed axially along the lead length at or near the distal lead portion and axially proximal the first electrode;
d) at least a second conductor electrically insulated from the first conductor and extending from an electrical connection at the second electrode to adjacent to the proximal lead end;
e) a first composite filter circuit comprising at least two coiled portions of the first conductor, the at least two coiled portions comprising a first spacing portion having a larger spacing between adjacent turns as compared to a second spacing portion;
f) wherein the first spacing portion comprises a first non-resonant inductance of at least 100 nanohenries and the second spacing portion provides a second self-resonant inductor, and wherein the first inductance is non-resonant at or near an MRI RF pulsed frequency; and
g) a first dielectric material coating the first composite filter, wherein the second self-resonant inductor has a parasitic capacitance formed between the adjacent turns of the coiled conductor to thereby provide a resonant impedance of at least 500 ohms centered at the MRI RF pulsed frequency or across a range of frequencies about the center frequency; and
h) a second composite filter circuit comprising at least two portions of the second conductor, the at least two coiled portions comprising a third spacing portion having a larger spacing between adjacent turns as compared to a fourth spacing portion;
i) wherein the third spacing portion comprises a third non-resonant inductance of at least 100 nanohenries and the fourth spacing portion provides a fourth self-resonant inductor, and wherein the third inductance is non-resonant at or near the MRI RF pulsed frequency; and
j) a second dielectric material coating the second composite filter, wherein the fourth self-resonant inductor has a parasitic capacitance formed between the adjacent turns of the second coiled conductor along the fourth spacing portion to thereby provide fourth resonant impedance of at least 500 ohms centered at the MRI RF pulsed frequency or across a range of frequencies about the center frequency,
k) wherein at least the first and second dielectric materials adhesively attach together adjacent coils forming the second and fourth self-resonant inductors so that the second and fourth resonant impedances remain stable.

28. An implantable lead comprising a lead length extending axially from a proximal lead end to a distal lead portion having a distal lead end, wherein proximal the end lead is configured to be permanently or removably connectable to electronic circuits of an active implantable medical device (AIMD), the implantable lead comprising:
a) at least a first electrode contactable with biological cells, wherein the first electrode is disposed axially along the lead length at or near the distal lead end;
b) at least a first conductor extending from an electrical connection at the first electrode or adjacent to the proximal lead end;
c) at least a second electrode contactable with biological cells, wherein the second electrode is disposed axially along the lead length at the distal lead portion and axially proximal the first electrode;
d) at least a second conductor electrically insulated from the first conductor and extending from an electrical connection at the second electrode to or adjacent to the proximal lead end;
e) a first self-resonant inductor comprising a portion of the first conductor formed as a first coiled inductor;
f) a first dielectric material coating the first lead conductor forming the first self-resonant inductor, wherein a first inductance is formed by the first coiled inductor, and wherein a first capacitance comprises a first parasitic capacitance between adjacent turns of the first coiled inductor so that the first self-resonant inductor has a first resonant impedance of at least 500 ohms centered at an MRI RF pulsed frequency or across a range of frequencies about the center frequency, wherein the first self-resonant inductor is disposed axially along the lead length between the first and second electrodes;
g) a second self-resonant inductor comprising a portion of the second conductor formed as a second coiled inductor;

h) a second dielectric material coating the second lead conductor forming the second self-resonant inductor, wherein a second inductance is formed by the second coiled inductor, and wherein a second capacitance comprises a second parasitic capacitance between adjacent turns of the second coiled inductor so that the second self-resonant inductor has a second resonant impedance of at least 500 ohms centered at the MRI RF pulsed frequency or across a range of frequencies about the center frequency, wherein the second self-resonant inductor is disposed axially along the lead length between the second electrode and the proximal end of the implantable lead;

i) a first plurality of non-resonant inductors, each of at least 100 nanohenries and electrically coupled in series along the first conductor, wherein the first plurality of inductors are non-resonant at or near the MRI RF pulsed frequency; and j) a second plurality of non-resonant inductors, each of at least 100 nanohenries and electrically coupled in series along the second conductor, wherein the second plurality of inductors are non-resonant at or near the MRI RF pulsed frequency;

k) wherein the first and second plurality of inductors are staggered in linear relation along the respective first and second conductors so that the first and second plurality of inductors are disposed between each other along the axial lead length so that the staggering prevents the first plurality of inductors from electrically interfering with the second plurality of inductors, l) wherein the first and second dielectric materials adhesively attach together adjacent coils forming the first and second self-resonant inductors so that the first and second resonant impedances remain stable.

29. The implantable lead of claim 28, wherein the first and second self-resonant inductors are staggered in linear relation to each other along the axial lead length so that they are not adjacently disposed.

30. An implantable lead comprising a lead length extending axially from a proximal lead end to a distal lead portion having a distal lead end, wherein the proximal lead end is configured to be permanently or removably connectable to electronic circuits of an active implantable medical device, the implantable lead comprising:

a) at least a first electrode contactable with biological cells, wherein the first electrode is disposed along the axial lead length at or near the distal lead end;

b) at least a first conductor extending from an electrical connection at the first electrode to or adjacent to the proximal lead end;

c) at least a second electrode contactable with biological cells, wherein the second electrode is disposed axially along the lead length at or near the distal lead portion and axially proximal the first electrode;

d) at least a second conductor electrically insulated from the first conductor and extending from an electrical connection at the second electrode to or adjacent to the proximal lead end;

e) a first set of non-resonant inductors comprising at least two inductors, each of at least 100 nanohenries and being electrically coupled in series along the first conductor, wherein the first set of inductors are non-resonant at or near an MRI RF pulsed frequency; and f) a first self-resonant inductor comprising a portion of the first conductor formed as a first coiled inductor;

g) a first dielectric material coating the lead conductor forming the first self-resonant inductor, wherein a first inductance is formed by the first coiled inductor, and wherein a first capacitance comprises a first parasitic capacitance between adjacent turns of the first coiled inductor so that the first self-resonant inductor has a first resonant impedance of at least 500 ohms centered at the MRI RF pulsed frequency or across a range of frequencies about the center frequency, wherein the first self-resonant inductor is disposed axially along the lead length between the first and second electrodes;

h) a second self-resonant inductor comprising a portion of the second conductor formed as a second coiled inductor;

i) a second dielectric material coati the lead conductor forming the second self-resonant inductor, wherein a second inductance is formed by the second coiled inductor, and wherein a second capacitance comprises a second parasitic capacitance between adjacent turns of the second coiled inductor so that the second self-resonant inductor has a second resonant impedance of at least 500 ohms centered at the MRI RF pulsed frequency or across a range of frequencies about the center frequency, wherein the second self-resonant. inductor is disposed axially along the lead length between the second electrode and the proximal end of the implantable lead;

j) a second set of non-resonant inductors comprising at least two inductors, each of at least 100 nanohenries and being electrically coupled in series along the second conductor, wherein the second set of inductors are non-resonant at or near an MRI RF pulsed frequency;

k) wherein any inductor of the at least two inductors of the first set of inductors are never adjacently disposed along the axial lead length next to any inductor of the at least two inductors of the second set of inductors so that the first and second sets of inductors are prevented from electrically interfering with each other, l) wherein the first and second dielectric materials adhesively attach together adjacent coils forming the first and second self-resonant inductors so that the first and second resonant impedances remain stable.

31. The implantable lead of claim 30, wherein the at least two inductors of the first set of inductors and the at least two inductors of the second set of inductors are non-resonant at or near an MRI RF pulsed frequency.

32. The implantable lead of claim 30, wherein the at least two inductors of the first set of inductors and the at least two inductors of the second set of inductors are wrapped around respective mandrels, each mandrel comprising a lumen extending from a proximal mandrel end to a distal mandrel end.

33. The implantable lead of claim 1, wherein the at least one second inductance is non-resonant at or near an MRI RF pulsed frequency.

34. The implantable lead of claim 1, wherein the at least one second inductance comprises a plurality of second inductances provided at spaced location along the at least one lead conductor.

35. The implantable lead of claim 1, wherein the at least one self-resonant inductor is wrapped around a mandrel comprising a lumen extending from a proximal mandrel end to distal mandrel end.

36. The implantable lead of claim 6, wherein the at least one inductor of the low pass filter is non-resonant at or near an MRI RF pulsed frequency.

37. The implantable lead of claim 11, wherein the third and fourth inductances are non-resonant at or near an MRI RF pulsed frequency.

38. The implantable lead of claim 11, wherein the first and second self-resonant inductors are wrapped around respective mandrels, each mandrel comprising a lumen extending from a proximal mandrel end to a distal mandrel end.

39. The implantable lead of claim 20, wherein the third and fourth inductances are non-resonant at or near an MRI RF pulsed frequency.

40. The implantable lead of claim 20, wherein the first and second self-resonant inductors are wrapped around respective mandrels, each mandrel comprising a lumen extending from a proximal mandrel end to a distal mandrel end.

41. The implantable lead of claim 27, wherein the first and third inductances are non-resonant at or near an MRI RF pulsed frequency.

42. The .implantable lead of claim 27, wherein the second and fourth self-resonant inductors are wrapped around respective mandrels, each mandrel comprising a lumen extending from a proximal mandrel end to a distal mandrel end.

43. The implantable lead of claim 28, wherein the first and second plurality of inductors are non-resonant at or near an MRI RF pulsed frequency.

44. An implantable lead, probe or catheter, comprising:
 a) at least one conductor extending from a proximal conductor end to a distal conductor portion having a distal conductor end;
 b) at least one self-resonant inductor comprising at least a portion of the lead conductor formed as a coiled inductor;
 c) a first dielectric material coating the lead conductor forming the at least one self-resonant inductor;
 d) at least one electrode electrically connected to the lead conductor at the distal conductor portion or the distal conductor end, wherein the electrode is configured for placement in contact with biological cells; and
 e) at least one second inductance of at least 100 nanohenries electrically connected in series along the length of the lead conductor, wherein the second inductance is non-resonant at or near an MRI RF pulsed frequency,
 f) wherein the self-resonant inductor has a parasitic capacitance between adjacent turns of the coiled inductor to thereby provide an equivalent circuit comprising an inductance in parallel with a capacitance so that the self-resonant inductor has a resonant impedance of at least 500 ohms centered at the MRI RF pulsed frequency or across a range of frequencies about the center frequency,
 g) wherein the parasitic capacitance provides a capacitor series resistance $R_c$ and the self-resonant inductor has an inductance and an inductor series resistance $R_L$, wherein at low frequencies of about 10 Hz to about 1 kHz an inductor reactance and the inductor series resistance permit passage of biological signals, and wherein at the low frequencies of about 10 Hz to about 1 kHz, a capacitor reactance and the capacitor series resistance substantially act as an open circuit to the same biological signals that the self-resonant inductor allows to pass, and
 h) wherein the self-resonant inductor has an overall circuit Q so that the resultant 3-dB bandwidth is at least 100 kHz, and
 i) wherein at least the first dielectric material adhesively attach together adjacent coils forming the first self-resonant inductor so that the first resonant impedance remains stable.

45. The implantable lead, probe or catheter of claim 44, wherein the at least one second inductance comprises a plurality of second inductances provided at spaced location along the at least one lead conductor.

46. The implantable lead, probe or catheter of claim 44, wherein the at least one second inductance is equal to or greater than 300 nanohenries.

47. The implantable lead, probe or catheter of claim 44, wherein the at least one electrode is selected from an active fixation tip electrode, a passive tip electrode including fixation tines, and a ring electrode.

48. The implantable lead, probe or catheter of claim 44, wherein the coiled inductor contacted with the dielectric material is wrapped around a mandrel.

49. The implantable lead, probe or catheter of claim 48, wherein the mandrel comprises a lumen extending from a proximal mandrel end to a distal mandrel end.

50. The implantable lead, probe or catheter of claim 49, wherein the proximal and distal mandrel ends are electrically conductive.

51. The implantable lead, probe or catheter of claim 44 wherein there are at least two electrodes, one comprising an ablation electrode and the other comprising a sensing electrode.

52. The implantable device of claim 1 wherein the first and second dielectric materials are the same or different.

53. The implantable device of claim 1 wherein the second dielectric material also adhesively attach together adjacent coils forming the second inductance.

54. The implantable device of claim 53, wherein the at least one second inductance is non-resonant at or near an MRI RF pulsed frequency.

55. The implantable device of claim 11 wherein the third and fourth dielectric materials also adhesively attach together adjacent coils forming the third and fourth inductances.

56. The implantable device of claim 27 wherein the first and second dielectric materials also adhesively attach together adjacent coils forming the first and second non-resonant inductances.

57. The implantable device of claim 28 wherein the first and second dielectric materials also adhesively attach together adjacent coils forming the first and second plurality of non-resonant inductances.

58. The implantable device of claim 30 wherein the first and second dielectric materials also adhesively attach together adjacent coils forming the first and second set of non-resonant inductors.

59. The implantable device of claim 44 wherein the first and second dielectric materials also adhesively attach together adjacent coils forming the first and second non-resonant inductances.

60. An implantable device, comprising:
 a) at least one lead conductor having a length extending from a proximal conductor end to a distal conductor portion having a distal conductor end, wherein the proximal conductor end is electrically connectable to an active implantable medical device;
 b) at least one electrode electrically connected to the distal conductor portion or the distal conductor end, wherein the electrode is contactable with biological cells; and
 c) at least one self-resonant inductor comprising at least a portion of the lead conductor formed as a coiled inductor;
 d) first dielectric material coating the lead conductor forming the self-resonant inductor having a parasitic capacitance between adjacent turns of the coiled inductor to thereby provide an equivalent circuit comprising a first inductance in parallel with a capacitance so that the self-resonant inductor is resonant at or near an MRI RF pulsed frequency; and e) at least one second inductance of at least 100 nanohenries electrically connected in series with the self-resonant inductor along the length of the lead conductor, wherein the second inductance is non-resonant at or near the MRI RF pulsed frequency; and f) a second dielectric material coating the second inductance, g) an adhesive contacting at least the first dielectric material to thereby adhesively attach together adjacent coils forming the self-resonant inductor so that the resonant impedance remains stable.

61. The implantable device of claim 60 wherein the adhesive contacts the second dielectric material to thereby adhesively attach together adjacent coils forming the second inductance so the second inductance remains stable.

* * * * *

UNITED STATES PATENT AND TRADEMARK OFFICE
CERTIFICATE OF CORRECTION

| | | |
|---|---|---|
| PATENT NO. | : 8,996,126 B2 | Page 1 of 1 |
| APPLICATION NO. | : 13/401608 | |
| DATED | : March 31, 2015 | |
| INVENTOR(S) | : Stevenson et al. | |

It is certified that error appears in the above-identified patent and that said Letters Patent is hereby corrected as shown below:

In the Specification

Column 13, line 44 delete "preventingress" and insert --prevent ingress--

Column 41, line 64 delete "preventingress" and insert --prevent ingress--

Column 43, line 13 delete "preventingress" and insert --prevent ingress--

In the Claims

Column 54, line 40 (Claim 6, line 24) delete "is" and insert --in--

Column 55, line 17 (Claim 11, line 21) after the word "least" insert the word --a--

Column 55, line 45 (Claim 11, line 47) delete "equency" and insert --frequency--

Column 56, line 11 (Claim 15, line 3) after the word "wherein" delete the ","

Column 57, line 58 (Claim 27, line 19) after the words "electrode to" insert --or--

Column 58, line 42 (Claim 28, line 11) after the word "electrode" insert --to--

Column 60, line 23 (Claim 30, line 51) after the word "self-resonant" delete the "."

Column 62, line 64 (Claim 60, line 13) before the word "first" insert --a--

Signed and Sealed this
Sixteenth Day of February, 2016

Michelle K. Lee
*Director of the United States Patent and Trademark Office*